United States Patent [19]

Benton et al.

[11] Patent Number: 4,822,608

[45] Date of Patent: Apr. 18, 1989

[54] METHODS AND COMPOSITIONS FOR THE TREATMENT OF MAMMALIAN INFECTIONS EMPLOYING MEDICAMENTS COMPRISING HYMENOPTERA VENOM OR PROTEINACEOUS OR POLYPEPTIDE COMPONENTS THEREOF

[75] Inventors: Allen W. Benton, Bozman, Md.; Lorraine Mulfinger, Belefonte, Pa.

[73] Assignee: Vespa Laboratories, Inc., Spring Mills, Pa.

[21] Appl. No.: 96,628

[22] Filed: Sep. 14, 1987

[51] Int. Cl.$^4$ .................. A61K 35/64; A61K 37/02
[52] U.S. Cl. .................. 424/98; 424/88; 424/91; 424/114; 514/21; 514/12
[58] Field of Search .................. 424/88, 91, 95, 114; 514/21, 12

[56] References Cited

U.S. PATENT DOCUMENTS

| 3,775,786 | 12/1973 | Reinert et al. |
| 3,856,936 | 12/1974 | Vick et al. ........................ 424/98 |
| 4,048,304 | 9/1977 | Celmer et al. |
| 4,163,049 | 7/1979 | Aubin. |
| 4,178,152 | 12/1979 | Nunogaki. |
| 4,338,297 | 7/1982 | Michael et al. |
| 4,370,316 | 1/1983 | Saikawa et al. |
| 4,444,753 | 4/1984 | Saikawa et al. |
| 4,469,677 | 9/1984 | Michael et al. |
| 4,473,495 | 9/1984 | Patterson ........................ 424/88 X |
| 4,629,706 | 12/1986 | Hammond et al. |

OTHER PUBLICATIONS

Proc. Soc. Exp. Biol. Med. 127: 707–710, Fennel et al.

Primary Examiner—Howard E. Schain
Attorney, Agent, or Firm—John F. A. Earley; John F. A. Earley, III; P. Michael Walker

[57] ABSTRACT

Methods and compositions are described for the treatment of mammalian infections, including bacterial, viral and cancerous infections, in which hymenoptera venom or proteinaceous or polypeptide components thereof are employed to enhance the activity of primary anti-bacterial, anti-viral, anti-carcinogenic or carcinostatic agents.

22 Claims, 20 Drawing Sheets

FIG.1
The Amino Acid Sequence of Melittin

X[1]-Gly-Ile-Gly-Ala-Val-Leu-Lys-Val-Leu-Thr
1                                          10

-Thr-Gly-Leu-Pro-Ala-Leu-Ile-Ser-Trp-Ile
11                                      20

Lys-Arg-Lys-Arg-Gln-Gln-NH$_2$
21                26

1 - "X" represents H or a formyl group.

Figure 2:
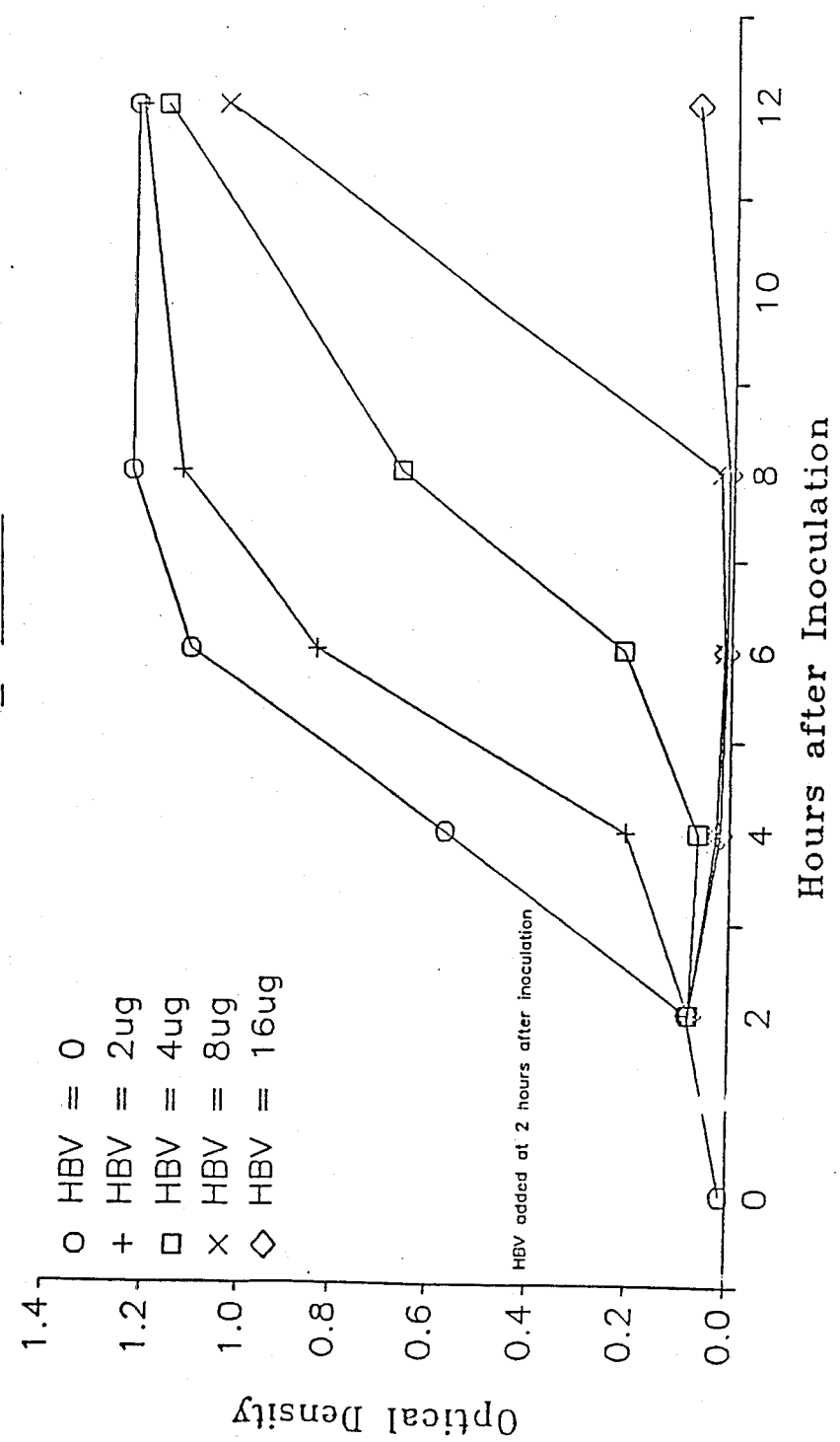

FIG. 2 Antibacterial Activity of Honeybee Venom on *S. aureus*

1  2  3  4  5

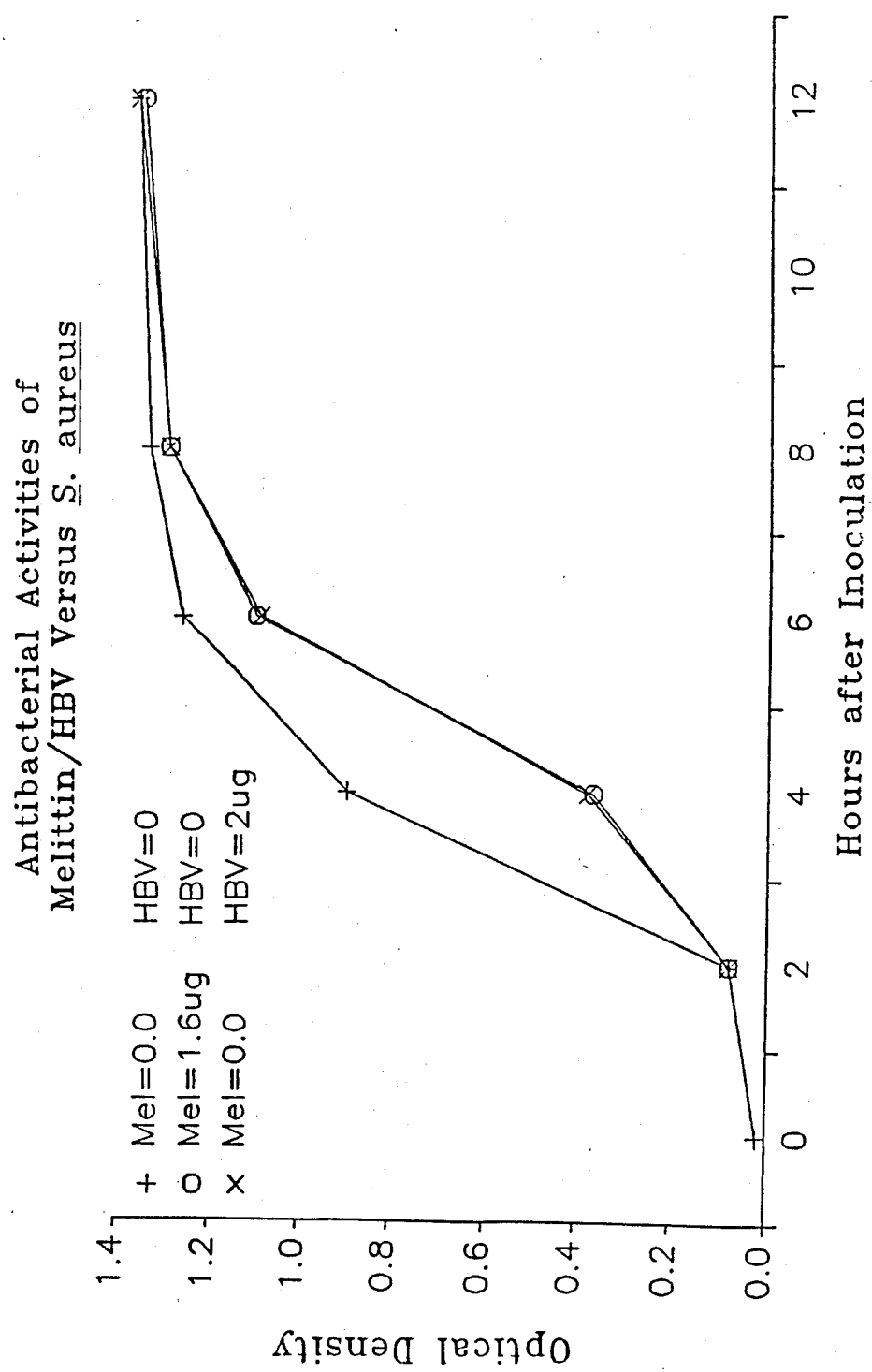

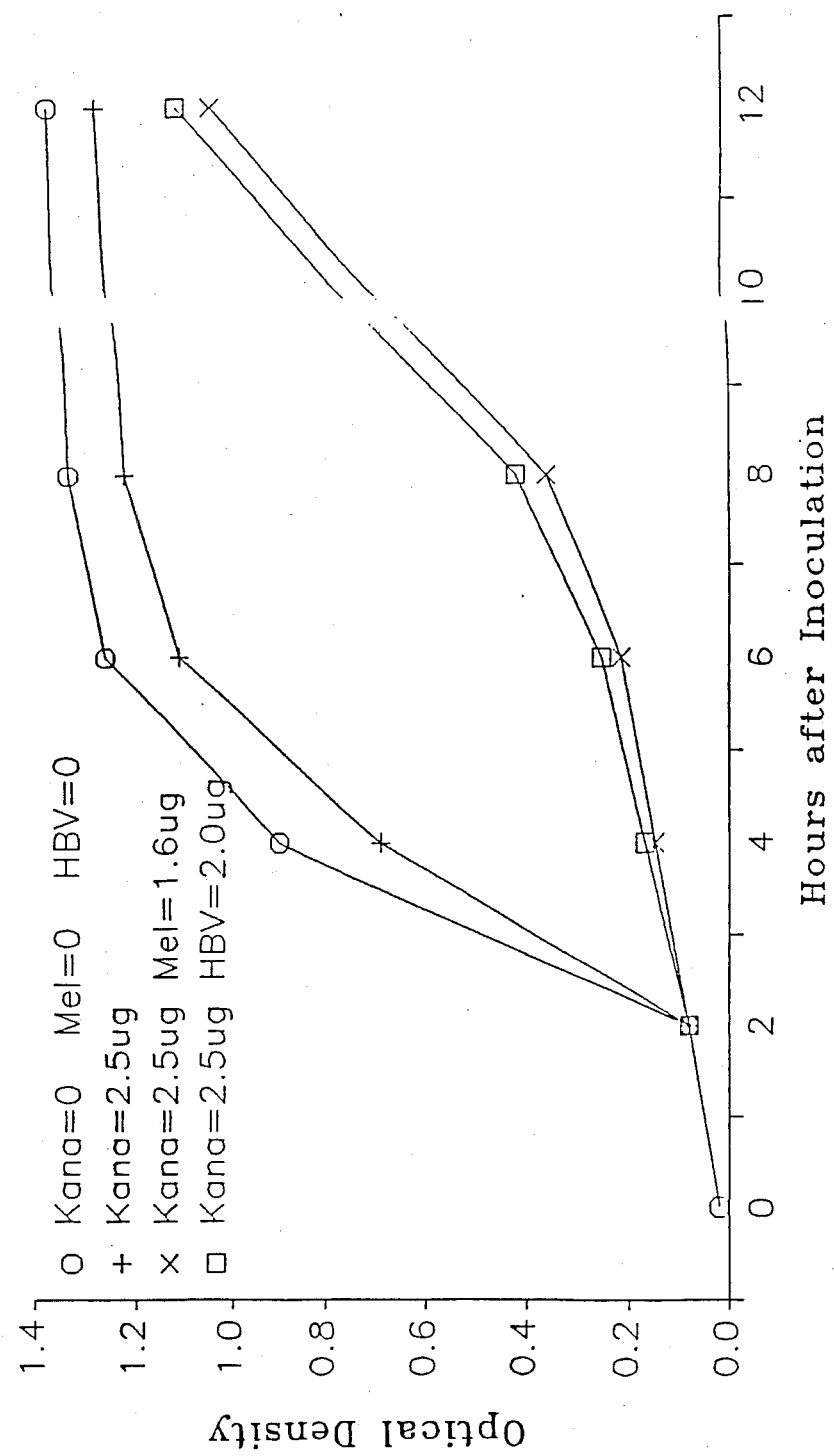

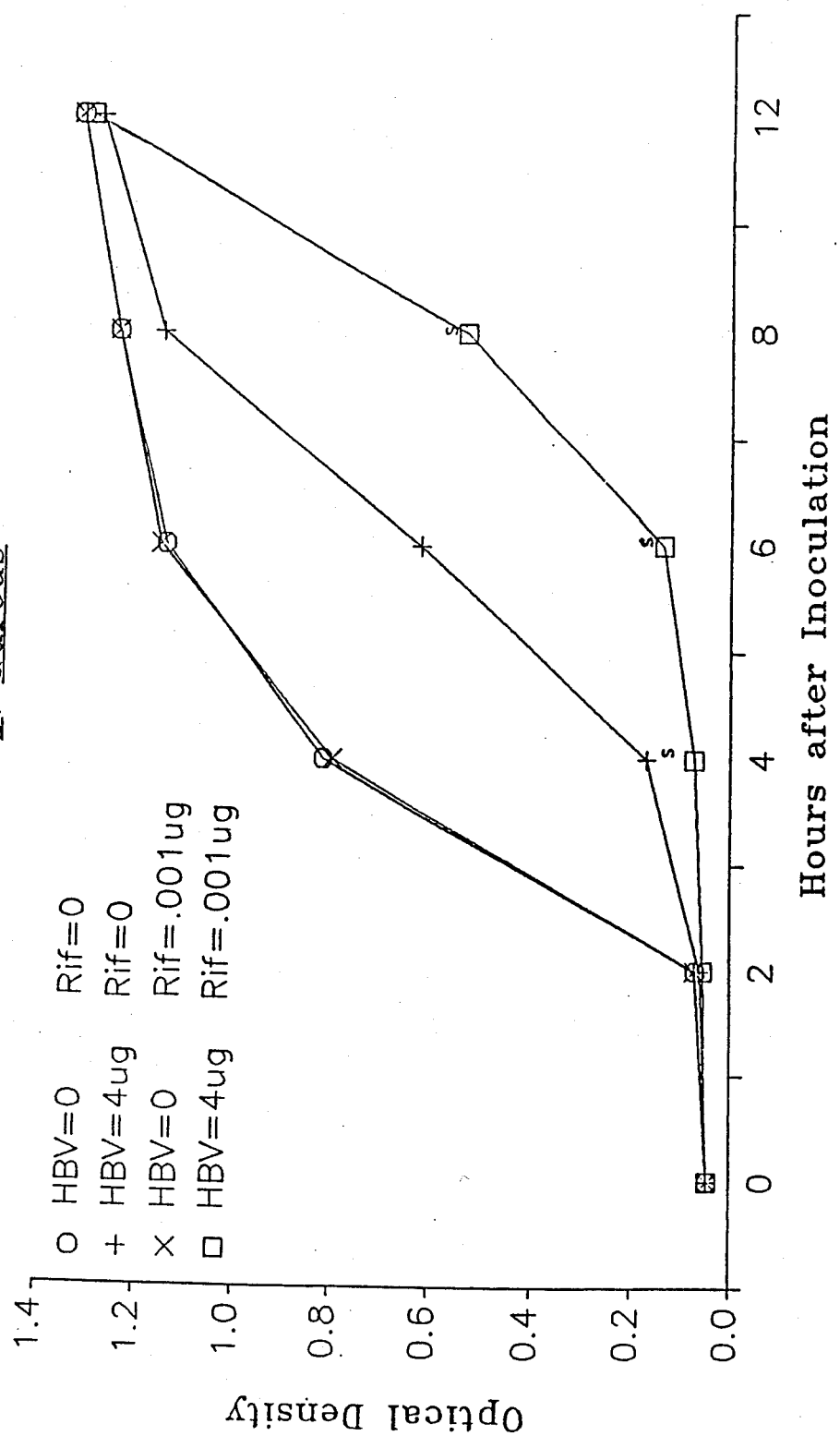

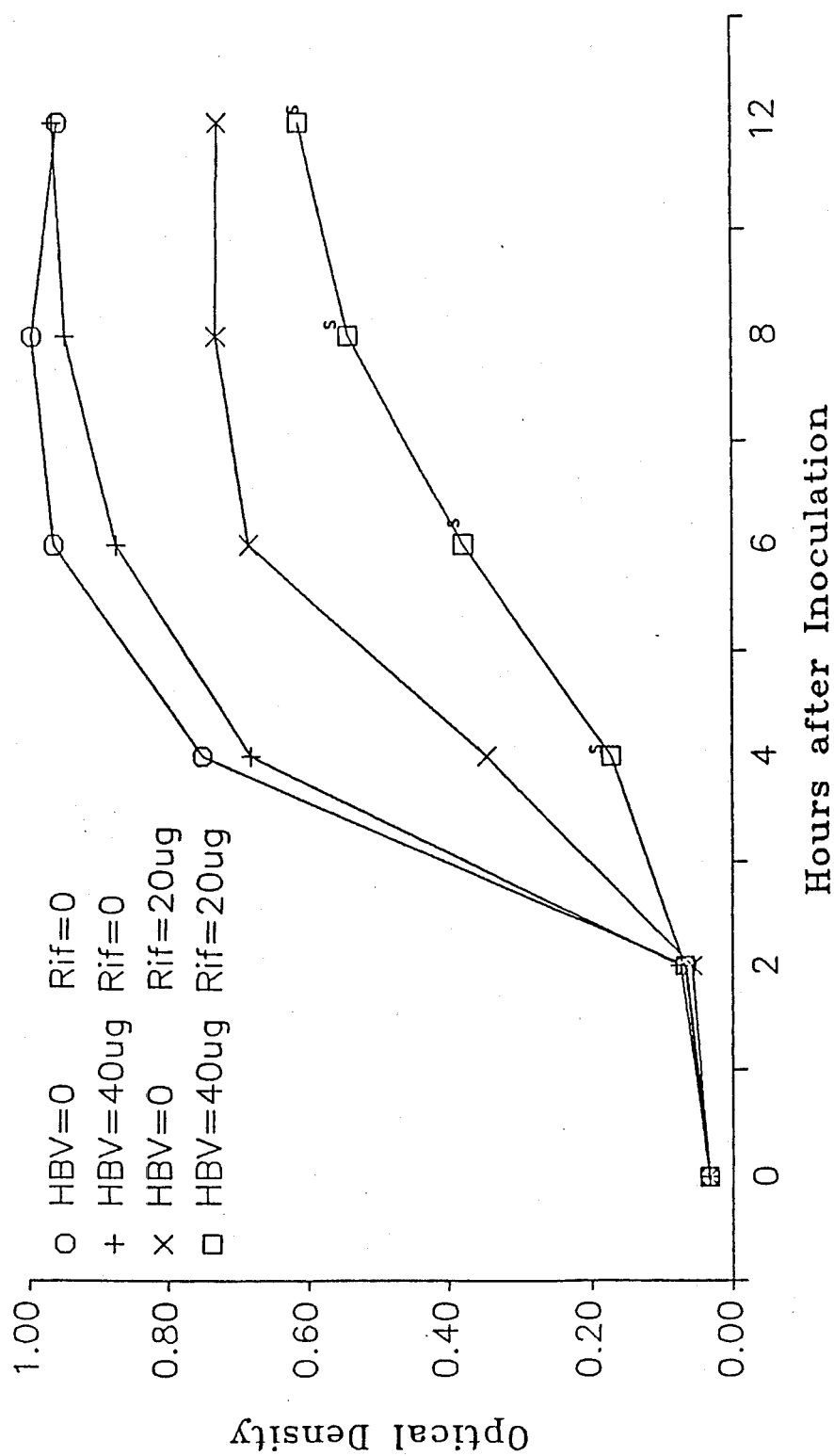

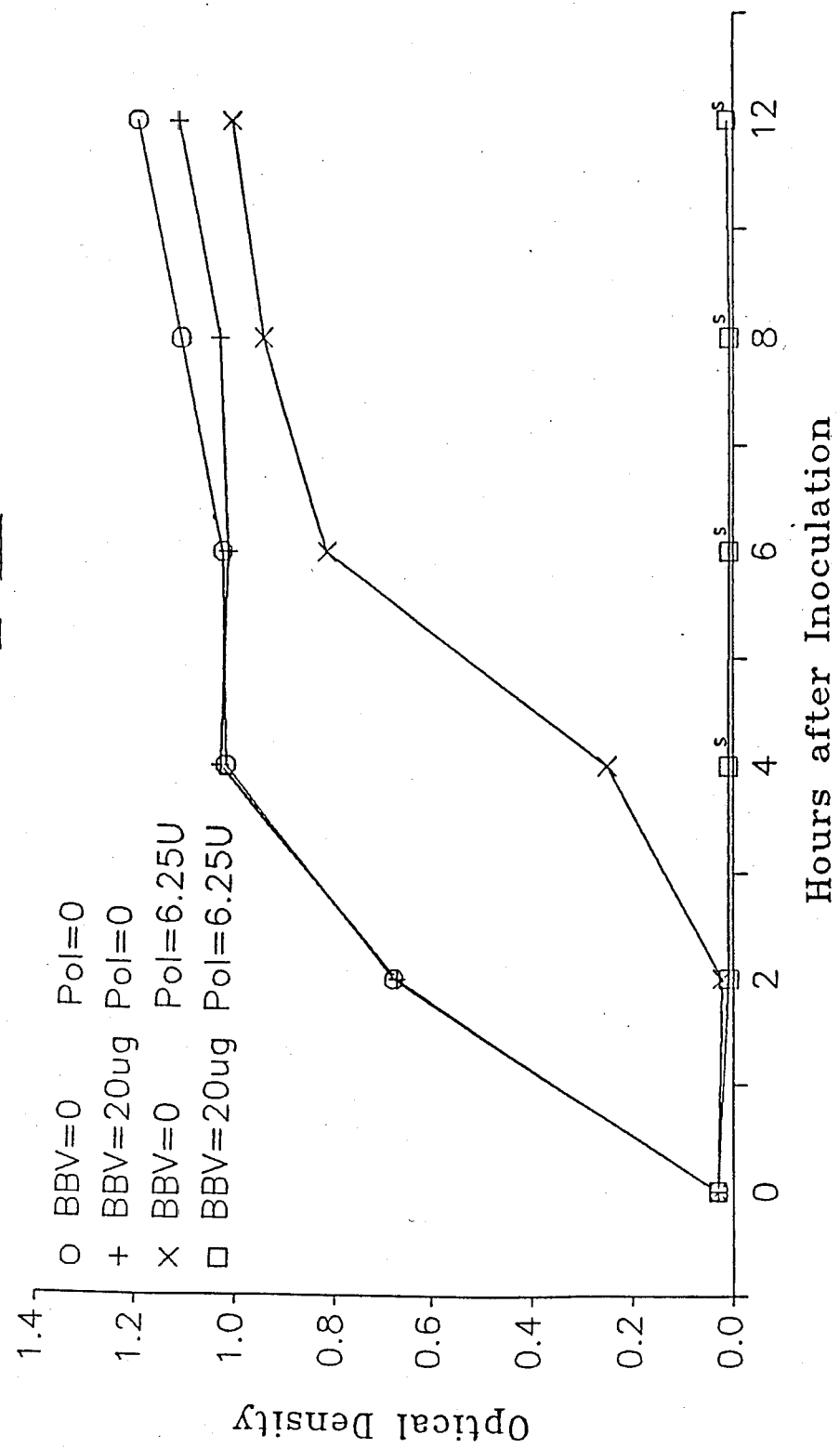

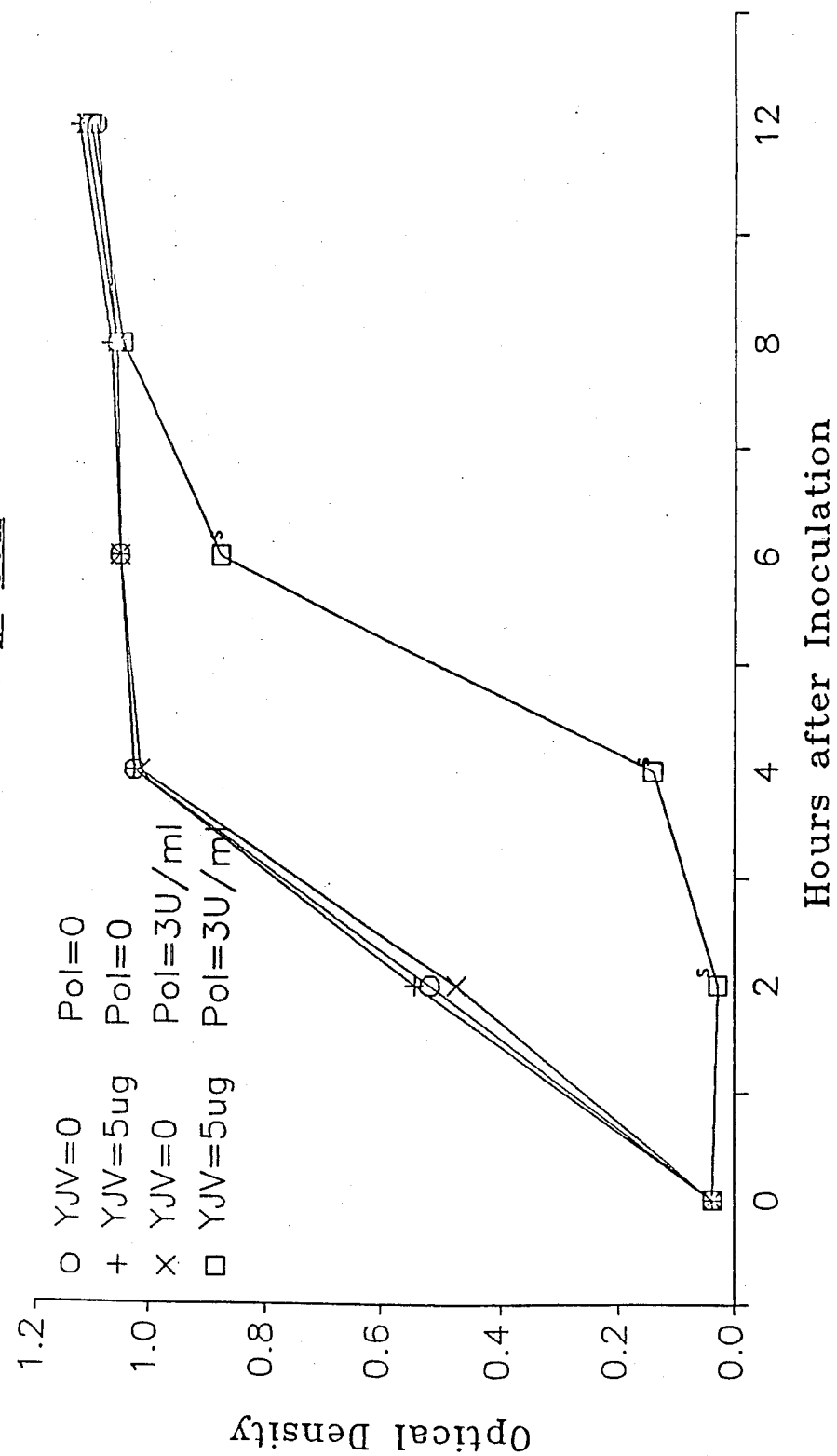

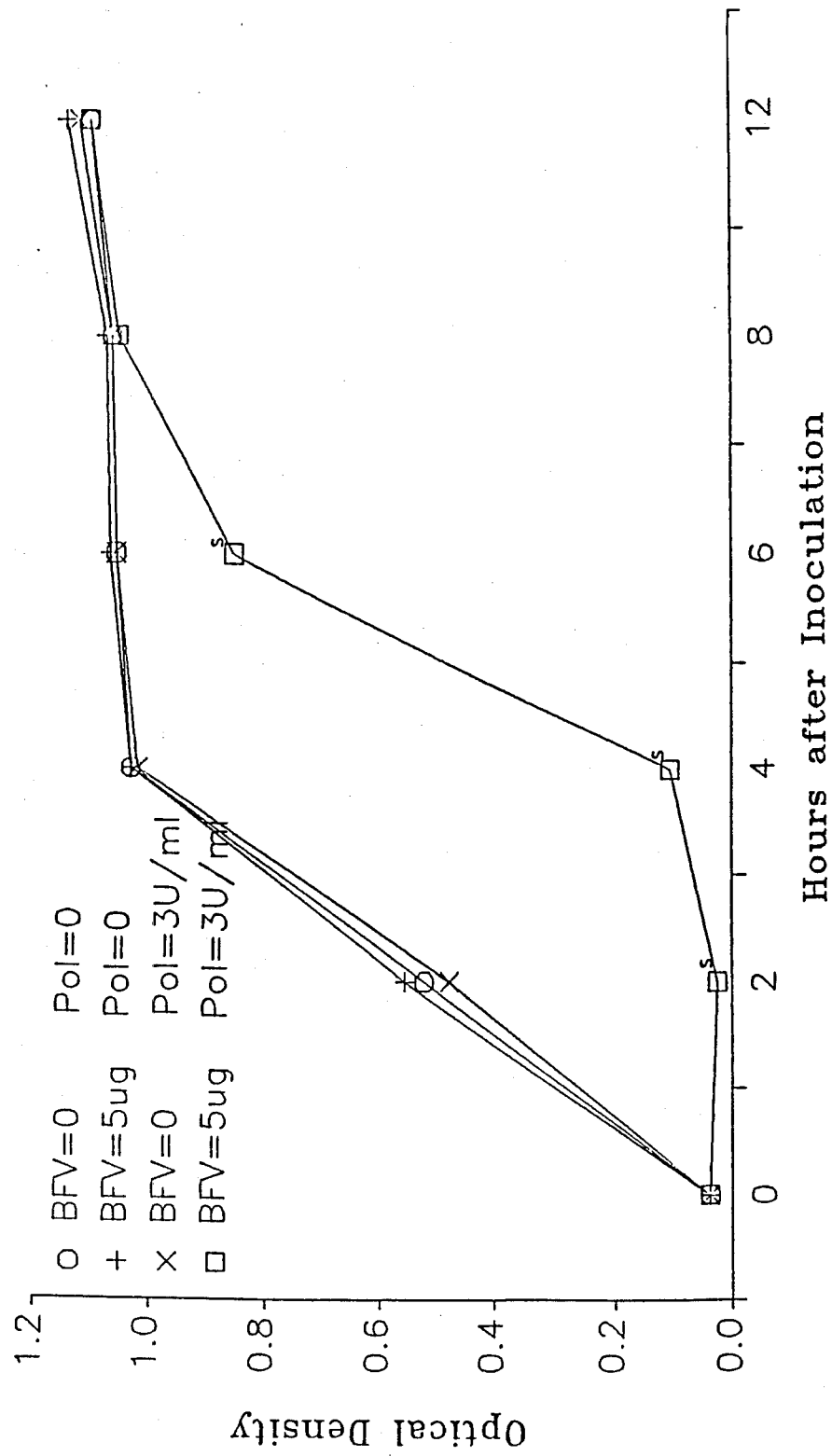

METHODS AND COMPOSITIONS FOR THE TREATMENT OF MAMMALIAN INFECTIONS EMPLOYING MEDICAMENTS COMPRISING HYMENOPTERA VENOM OR PROTEINACEOUS OR POLYPEPTIDE COMPONENTS THEREOF

INTRODUCTION

This invention relates to the use of certain secondary agents derived from nature in the enhancement of the activity of other primary chemotherapeutic agents useful against bacterial, viral and cancerous infections, and especially the activity of antibiotic agents. The identity of anti-bacterial, anti-viral and anti-carcinogenic agents, and in particular antibiotic agents, and the activities and therapeutic usage of these materials are well known. The secondary agents employed in the invention in the enhancement of the activity of these primary anti-infectious agents are also known per se and have, in some cases, been used in medicine, but their ability to enhance the activity of anti-bacterial, anti-viral and anti-carcinogenic agents and, particularly, antibiotic agents, has not been recognized previously. The secondary agents employed in the invention are obtained from the venom of species of the order hymenoptera, which includes, without limitation, and by way of example only, honeybees, bumblebees, yellow jackets, bald faced hornets, fire ants, and the like.

SUMMARY OF THE INVENTION

The invention resides in the discovery that hymenoptera venom, or isolated active proteinaceous or polypeptide components of such venoms, enhance or potentiate the activity of anti-bacterial, anti-viral and anti-carcinogenic agents and, especially, antibiotic agents.

The present invention grew out of the work described in a thesis in veterinary science by Lorraine Smith Mulfinger, entitled "Synergistic Activity Of Honeybee Venom With Antibiotics", which is to be submitted to the Graduate School Department of Veterinary Science of the Pennsylvania State University. The entire contents of that thesis is hereby made a part of the disclosure herein by reference. References to earlier work by others below have been abbreviated here since the full references are set forth in the bibliography of the Mulfinger thesis and at the end of this application.

BACKGROUND AND PRIOR ART

The use of anti-bacterial, anti-viral carcinostatic and anti-carcinogenic substances, while widely known in the art, is still the subject of massive continuing research, much of which, in addition to the discovery of new agents, is directed to the discovery of means for the enhancement of the activity of known active agents.

Indeed, certain substances derived from bee venom have been studied and have been found useful in certain specific pharmacologic applications. For example, U.S. Pat. No. 4,444,753 issued Apr. 24, 1984, describes a composition comprising a component obtained by de-proteinizing an extract from the poison pouch contents of bees. This product has an immuno-stimulating activity, a carcinostatic activity, an effect of enhancing the antibacterial activity of an anti-bacterial substance, and an effect of enhancing the carcinostatic activity of a carcinostatic substance. The invention disclosed in that patent is directed to carcinostatic, immuno-stimulating and antibacterial agents comprising the composition described. While that invention is similar in purpose to that of the present invention, it differs in that the bee extract is modified by deproteinizing it so that it is negative in biuret reaction and sulfosalicylic acid reaction.

U.S. Pat. No. 4,370,316, issued Jan. 25, 1983 to the same inventors as the patent described above, also claims a method of treating a host animal having decreased immunity by administering an effective amount of the deproteinized extract from the poison pouch of the bee.

Therefore, while anti-bacterial, anti-viral and anti-carcinogenic substances are well known, and it is also known that a deproteinized extract from the poison pouch of a bee has certain useful activities, including anti-bacterial activity, activity in stimulating anti-bacterial activity and immuno-stimulating activity, it has not been recognized previously that proteinaceous hymenoptera venoms or proteinaceous or polypeptide extracts thereof have an enhancing effect on virtually all anti-bacterial, anti-viral, carcinostatic and anti-carcinogenic agents. Such enhancement of the activity of such primary anti-infectious agents not only increases the effect of dosages of such agents which would be effective alone but can also render effective low dosages of such agents which would be ineffective if used alone.

As noted above, the present invention relates to the use of hymenoptera venom or proteinaceous or polypeptide components thereof to enhance the activity of anti-infectious therapeutic agents in general. To simplify the description of the invention, however, it will be discussed below for purposes of illustration, in the use of honeybee venom or its proteinaceous extract melittin, in the enhancement of the activity of antibiotics in the control of bacterial, viral, and cancerous infections. Honeybee venom (HBV has been selected since it is readily available. It is to be understood, however, that the venom of other hymenoptera and proteinaceous or polypeptide components thereof are also effective in the invention in varying degrees. Similarly, anti-infectious agents other than antibiotics may also be employed in the invention in the treatment of infections for which they have been used previously, but with enhanced effect when used in combination with the proteinaceous hymenoptera agents.

As further background, it is noted that honeybee venom is credited with a multitude of useful activities. Some of the activities are scientifically documented while others appear to be based on empirical data and folklore. The in vitro antibacterial activity of honeybee venom is well documented (Schmidt-Lange, 1951; Ortel and Markwardt, 1955; Fennel et alia, 1968), however, few efforts have been made to put this activity to practical use. In the present invention, the data from several empirical experiments indicated that the antibacterial activity of honeybee venom may have a significant effect in vivo, in the presence of antibiotics. Based upon these observations, an investigation was designed to study the interactions of honeybee venom and antibiotics using an in vitro assay where the two compounds could be evaluated without the contributing effects of the natural immune responses of the host animal.

In this study, three strains of bacteria were tested initially against three different antibiotics using separate checkerboard titrations of honeybee venom with each antibiotic. Representatives of three major groups of antibiotics (penicillins, aminoglycosides, and polymyxins) were selected and assayed to determine if honeybee venom could improve the antibacterial efficacy of selected antibiotics. An antibiotic from a fourth major group was studied later as described below.

Once synergy was demonstrated in the checkerboard assay, a broader survey was attempted using a simplified procedure. Two automated minimal inhibitory concentration (MIC) assay plates, which titrate susceptibility to eleven antibiotics simultaneously, were inoculated in parallel with bacterial cultures with and without non-inhibitory doses of honeybee venom (HBV). Eight gram-positive and four gram-negative organisms were tested using this system in an effort to find classes of antibiotics that routinely produce synergy with HBV, and to determine the spectrum of synergistic action of these combinations among different groups of bacteria.

In addition to testing whole honeybee venom, the venom was fractionated by size exclusion chromatography. Each of four fractions were tested to determine if a specific component was responsible for antibacterial activity and could also act synergistically in antibacterial assays. It was shown that the fraction containing melittin, which had been previously identified as the antibacterial element of the honeybee venom (Fennel et alia, 1968), is active in its purified form and will act synergistically in a magnitude equal to that of whole honeybee venom.

COMPOSITION OF VENOMS

Venoms are heterogeneous mixtures of biochemical compounds. Most venoms are more than 90% protein. Toxins and enzymes make up this protein portion and are the cause of direct cell damage. While many enzymes such a phospholipase A2, acid phosphatase, and hyaluronidase are common to most venoms, toxins and other biologically active peptides contained in venoms are highly species specific.

Venom producing insects all belong to the insect order Hymemoptera. Like snake venoms, enzymatic activities such as phospholipase A2, hyaluronidase, and acid phosphatase are common to all insect venoms. The toxin and peptide components, however, vary from species to species. (Tu, 1977b)

The venom of the Italian honeybee (*Apis mellifera*) is the most extensively studied insect venom. The major component of honeybee venom is melittin. This peptide has a molecular weight of 2,847 daltons and accounts for approximately 50% of the venom's dry weight. A second peptide, apamine, is present as approximately five percent of the venom and several other peptides are present in trace amounts. (Haberman, 1972)

ANTIBACTERIAL ACTIVITY OF HONEYBEE VENOM

The bactericidal activity of honeybee venom was first documented in 1941 by W. Schmidt-Lange (1941). He tested *E. Coli* and staphylococci and found both to be susceptible to the antibacterial activity of honeybee venom. Additionally, he noted that the minimal inhibitory dose of honeybee venom for *E. coli* was much higher than for staphylococci.

It wasn't until ten years later that Brangi and Pavan (1951) evaluated various extraction procedures to isolate the antibacterial activity of honeybee venom. They found the activity to be present in both water and acetone extracts of venom. They also showed that the activity was stable when heated to 100 degrees centigrade for up to 15 minutes.

In 1955, Ortel and Markwardt (1955) published the results of an investigation of the variability in sensitivity among different bacteria to honeybee venom's antibacterial activity. Two hundred ninety-six strains of bacteria were tested. The results showed that tolerance to honeybee venom is much greater in gram-negative organisms than in gram-positive organisms. Ranges for bactericidal concentrations were reported to be 12.5 to 25 $\mu$g/ml for gram-positive bacteria and 1 to 10 mg/ml for gram-negative bacteria. The bactericidal activity co-purified with the red blood cell "direct hemolytic fraction". The name "melittin" had not yet been assigned to the active component of this fraction.

In 1963, Benton et alia published a bio-assay for honeybee venom. The bacteriostatic activity of venom was quantitated by a radial diffusion assay which measured zones of growth inhibition caused by serial venom dilutions in a lawn of bacterial growth. This assay was proposed to standardize the biological activity of honeybee venom intended for in vivo use. (Currently, allergy desensitization is the only in vivo honeybee venom treatment approved by the Food and Drug Administration of the United States). The article also tested the heat sensitivity of the honeybee venom activity and found it could withstand sterilization procedures (121 degrees centigrade for 15 minutes) (Benton et al. 1963).

MELITTIN ISOLATION AND ACTIVITIES

Honeybee venom has several pharmacologically active compounds. The compound appearing in the greatest proportion in venom is melittin, a polypeptide with a molecular weight of 2,847 daltons, that acts as a direct hemolysin of red blood cells. Other active components include phospholipase A2, histamine, dopamine, noradrenaline, apaamin, and hyaluronidase (Haberman, 1972).

Antibacterial Activity of Melittin

Fennel, Shipman, and Cole (1968), purified melittin with Sephadex G-50 chromatography and showed that the melittin fraction had "potent antibacterial activity". They tested 30 random strains of bacteria (including several streptococci, staphylococci, and enteric bacteria strains), comparing the activity of purified melittin to whole honeybee venom. They noted that one strain of *S. aureus*, a penicillin resistant isolate, showed no decrease in sensitivity to the melittin.

Although melittin had been reported to be the antibacterial factor of honeybee venom, no reports of its use in vivo have been found. It was noted by Mollay and Kreil (1974) that interactions between melittin and lecithin enhanced the activity of phospholipase A2 honeybee venom on lecithin. It has not previously been recognized, however, that melittin enhances the activity of antibiotics.

Haberman and Jentsch (1967) have purified melittin and published the amino acid sequence. They found that melittin exists in two natural forms, differing only by a formyl substitution at the N-terminces (FIG. 1).

Antibiotics

Antibiotics can be divided functionally into four groups based upon the active sites of the antibiotics (Volk, 1978a). Target structures of the four groups are the cell wall, the cell membrane, the protein synthesis machinery, and the nucleic acid replication machinery. Because of the complexity of the synergy assay, four antibiotics, one from each of the foregoing groups, were chosen for testing. The selected antibiotics were ampicillin, kanamycin, polymyxin B and refampicin. Each has a different mode of action on procaryotic cells.

Ampicillin

Ampicillin belongs to the group of antibiotics affecting cell wall structure. These antibiotics are all penicillin derivatives, each containing the functional beta-lactam ring. Collectively known as the beta-lactam group, these antibiotics block cell wall synthesis by inhibiting the transpeptidase enzyme which crosslinks the pentaglycine bridges of the peptidoglycan, therefore, only actively growing cells are affected by their presence.

Ampicillin is a semisynthetic derivative of penicillin. The synthetic step in ampicillin synthesis adds an amine group to the alpha carbon of penicillin G. This confers resistance to beta-lactamases (the predominant penicillin resistance factor of bacteria) giving ampicillin a much broader spectrum of efficacy among bacteria than penicillin (Volk, 1978b).

Kanamycin

Kanamycin is an aminoglycoside. This group of antibiotics block protein synthesis. Members of this group bind to the 30s ribosome of bacteria and sterically block the binding of aminoacyl-tRNA's or inhibit the translocation of the growing peptide chain at the ribosomal active site (Volk, 1979c). Since protein synthesis is required for many regulatory cell functions, aminoglycosides are effective on bacteria in either active or stationary growth phases.

Polymyxin B

Polymyxin B is a cyclic, amphiphatic peptide. Due to the combined hydrophilic and hydrophobic properties, polymyxin B has a detergent-like action that does not require cell growth to be effective. Like melittin, polymyxin B interacts with membranes to form small hydrophilic pores in the hydrophobic areas of membranes. In gram-negative organisms, which have a thick lipopolysaccharide layer acting as a selective permeability barrier, polymyxin B is effective in disturbing osmotic gradients. Therefore, polymyxin B is very effective on gram-negative organisms, while only minimally effective on gram-positive oganisms. (Sebek, 1979). While melittin can form membrane pores simularly to polymyxin B, melittin is more active on gram-positive organisms, therefore the action of melittin cannot be totally analogous to that of polymyxin B.

Rifampicin

Rifampicin is an antibiotic form the group which acts at the level of nucleic acid synthesis, which completes examples of antibiotics from the four main categories referred to above.

Synergy Studies

A review of articles studying synergy between antibiotics and other compounds in bacterial systems showed that all investigators used the same basic approach. Bacterial growth was monitored in broth cultures with and without each compound separately, and then with both compounds together. In order to prove synergistic action as opposed to an additive effect, in each case, at least one of the compounds was used at a level where alone it would demonstrate minimal growth inhibition. Thus, with one compound relatively inactive, any increased activity of the second compound in its presence would be the result of synergistic interactions (Moellering at alia, 1971; Carrizosa and Levison, 1981; and Cynamon and Palmer, 1983). It is upon this type of design that experiments in this invention were based.

MATERIALS AND METHODS

Materials

Honeybee (*Apis melifera*) venom was supplied by Vespa Laboratories, Spring Mills, Pa.

Bacteria strains were supplied by the Veterinary Science Department of the Pennsylvania State University. *S. aureus* #140A is a field isolate from a case of bovine mastitis. *E. coli* #G1880E was selected from the *E. coli* Reference Center systematic collection. A kanamycin resistant strain of *S. aureus* was isolated by a natural selection procedure described below.

Antibiotics were purchased from Sigma Chemical Company (St. Louis, Mo.) and activity units were based on their analyses.

Trypticase soy base (BBL Microbiology Systems, Cockeysville, Md.) was used to support all bacterial growth either as a broth or an agar.

Sephadex G-50 was obtained from Pharmacia Fine Chemicals, Uppsala, Sweden.

Minimal inhibitory concentration (MIC) assays of antibiotics with and without honeybee venom, were performed by the Microbiology Department of the Allegheny General Hospital, Pittsburgh, Pa., using the Sensititre TM assay system distributed by Gibco Laboratories, Lawrence, Mass.

Methods

Isolation of Kanamycin Resistant Mutant

*S. aureus* was grown in 5 ml of trypticase soy broth (TSB) overnight to an approximate density of $10^9$ colony forming units/ml. 0.1 ml of the overnight culture was plated on a plate of trypticase soy agar (TSA) containing 39 $\mu$g/ml kanamycin and incubated for 48 hours at 37 degrees centigrade. Colonies appearing within 48 hours were subcultured onto a second TSA plate supplemented with 39 $\mu$g/ml kanamycin.

Checkerboard Titration Assay for Synergy

Bacteria cultures were prepared for this assay by freezing each strain while in logarithmic growth in TSB. For this purpose, a 5 ml overnight culture was used to inoculate 200 ml of TSB in a 500 ml erlenmeyer flask. The culture was incubated at 37 degrees centigrade with constant stirring and the optical density (OD) at 660 nm was read hourly. When the culture reached mid-log phase (approximately 0.500 OD units), 5 ml aliquots were transferred to 16×100 mm screw cap tubes. All cultures were frozen and stored at −20 degrees centigrade. *E. coli* required glycerol to be added to the medium to a final concentration of 20% to survive freezing. This was accomplished by mixing 1 ml of sterile glycerol with 4 ml of log-phase culture immediately before freezing.

To begin an assay, one tube of a frozen culture was thawed in a beaker of water at room temperature. The thawed culture was added to 175 ml of TSB in a 500 ml erlenmeyer flask, stirred, and the $OD_{660}$ immediately measured and recorded as the "time zero" reading. The flask was then incubated at 37 degrees centigrade with constant stirring for two hours at which time the $OD_{660}$ was again read and recorded, the culture was split into 16×100 mm screw-cap test tubes prefilled with the specified aliquots of honeybee venom (HBV) and antibiotic described below.

Stock solutions of HBV and antibiotics were made in distilled water, filter sterilized, and stored at −20 degrees centigrade in 5 ml aliquots at concentrations twice the concentration needed for the checkerboard titration system. The frozen stock concentrations required for each bacterial species are given in Table 1. The concentration used for each bacterium was based on preliminary experiments using the antibiotics alone to determine the minimal inhibitory ranges of each antibiotic for each microorganism.

For each assay, one vial of antibiotic and one vial of HBV were thawed at room temperature and diluted with an equal volume of 2X TSB and then serially diluted twofold into normal strength TSB to obtain four concentrations of venom and four concentrations of antibiotic. Seventy-five screw capped test tubes were numbered and arranged to correspond to the checkerboard pattern shown in Table 2. TSB, antibiotic, and HBV were then dispensed according to the design shown in Table 3. Tubes labeled as OO and O contained 2.5 ml of TSB and served as OD blanks and sterility control tubes. Tubes 1–75, each containing a total volume of 500 $\mu$l, was inoculated with 2 ml of the two hour culture described above. [Note: the final concentration of HBV and/or antibiotic in each tube was one tenth of the concentration added in the 250 $\mu$l aliquot (refer to Table 3).] Each tube was immediately sealed and inverted. After all tubes were inoculated, they were placed in horizontal racks on a rocker platform at 37 degrees centigrade. The growth in each tube was individually monitored at four, six, eight, 12, and 24 hours by determining the optical density of each tube at 660 nm.

Minimal Inhibitory Concentration Assays with HBV

The microbiology laboratory of the Allegheny General Hospital, having the capacity to perform automated MIC assays, was contracted to perform a trial survey on 12 clinical bacterial isolates. The adaptation of the automated MIC assay had the following restrictions: (1) each assay could only test one dose level of HBV, and (2) the effect of the HBV alone could be evaluated only as completely inhibitory or non-inhibitory. Synergy of HBV with the 11 antibiotics in this system was evaluated by comparing two assays run simultaneously with and without HBV present. The dose of HBV used for each species was estimated to be a non-inhibitory dose, based on the checkerboard titration assays.

Melittin Purification

Sephadex®G-50 gel filtration bedding was swollen for 24 hours at room temperature in beta alanine-acetic acid buffer (BAAB), pH 4.3 (Guralnick et alia, 1986), and then equilibrated at five degrees centigrade overnight. A 2.5×60 cm column was poured and equilibrated at a flow rate of 1.0 ml/hour. One hundred mg of HBV was reconstituted in 5 ml of BAAB buf containing 20% sucrose. The HBV was layered on the column and eluted at a flow rate of 1 ml/hour. The effluent was monitored for absorbence at 280 nm. Fractions containing the main peak were pooled, an aliquot was assayed by the Lowry Protein Assay (Lowry, 1951), and the remainder was lyophilized.

Identification of the melittin fraction was based on the relative mobility and quantitation of bands appearing in polyacrylamide gel separations of each fraction (Benton, 1965). The melittin was also checked for purity by polyacrylamide gel electrophoresis. Electrophoresis was performed as described by Guralnick et alia, (1986). Lyophilized fractions were reconstituted to 2 mg/ml in the electrophoresis sample buffer and 50 ul samples were applied per sample well on the gels.

Whole Venom Equivalence of Melittin

The amount of the melittin fraction equivalent to its proportion in whole honeybee venom was determined by quantification of individual bands in electrophoresed samples of whole venom and the melittin fraction. Twenty, 40, 60, 80, and 100 ug samples of whole honeybee venom were separated by electrophoresis, stained with Coomassie® brilliant blue-perchloric acid stain, and scanned with a densitometer. A standard curve was established relating the peak area of the melittin band of the whole venom samples to the quantity of protein in the sample when it was applied. Six 40 ug samples of the purified melittin were assayed simultaneously and their equivalence in honeybee venom was determined from the standard curve. This procedure is described in detail by Mulfinger et alia. (1986).

Testing the Melittin Fraction for Synergistic Activity

To compare the antibacterial activity of whole honeybee venom and the melittin fraction, earlier checkerboard titration results were reviewed and the test system was selected where HBV dose effects could be easily seen alone and in combination with an antibiotic. Since staphylococci were susceptible to the HBV alone at concentrations used in the above checkerboard assays, and since kanamycin showed good synergistic action with the HBV, this system was chosen to compare the antibacterial activities of whole HBV and melittin. The doses of each component used in this analysis were 2 ug/ml HBV and 2.5 ug/ml kanamycin. These doses were in a range of bacterial reactivity where the effects of small dose changes were reproducible and easily measured. The equivalent dose of the melittin fraction for 2.0 ug/ml HBV was 1.6 ug/ml. Each experiment compared in parallel, triplicate samples of the melittin fraction and whole honeybee venom with and without kanamycin present to check for equivalent activity.

Statistical Analysis

Each checkerboard experiment was repeated five times. The averages of the five repetitions for each bacteria-antibiotic combination were tested at each time point for significant differences using a Waller-Duncan K-ratio T Test and families of curves were selected for synergy testing. A curve family consisted of an experiment control curve (bacterial growth with no antibiotic or HBV present), an antibiotic control curve (bacterial growth with antibiotic but no HBV present), a venom control curve (bacterial growth with HBV but no antibiotic present) and an interaction curve (growth with antibiotic and HBV present). Families in which the antibiotic control curve and the venom control curve showed small average OD decreases relative to the experiment control curve, and which also demonstrated large OD decreases in the interaction curve relative to the experiment control curve were tested for synergy.

A synergistic effect between compounds can be differentiated from an additive effect of the compounds since an additive effect is predictable. Additive effects can be predicted by summing the effects of the two compounds individually, thus, any greater effect would indicate synergistic interaction. An equation predicting OD readings for an additive interaction between HBV and an antibiotic was derived. See the Mulfinger thesis (1987) referred to above, pages 23–25.

RESULTS

Checkerboard Titration Assays

Three bacterial strains were tested against each of three antibiotics combined with honeybee venom. These nine combinations of bacteria, antibiotic, and HVB were analyzed using the checkerboard assay which provide for 25 treatments (antibiotic and HBV combinations) for each bacterium-antibiotic combination. Each checkerboard experiment included triplicate samples for each treatment and was repeated five times. The data from triplicate samples repeated in five experiments were averaged and the mean and standard deviation for each time point of each treatment appear in the appendix. For each bacterium-antibiotic combination, the mean OD values for each antibiotic/HBV treatment at each time point were arranged in descending order, and grouped according to significant differences using the Waller-Duncan K-ratio T test. From the Waller-Duncan profiles, families of four curves, as described in "Statistical Analysis" above were compared for evidence of synergy. The family of curves showing the greatest OD difference between the interaction curve and the lowest of the experiment curve, antibiotic control curve and venom control curve, was plotted and each time point was tested for synergy using the equation derived in the section "Statistical Analysis" above. For each family of curves, if the estimate of $(-X+A+V-AV)$ for a time point is significantly greater than zero at 95% confidence level (i.e., synergy is indicated), the time point is noted on the interaction curve by a superscript "s" at the square representing that time point (FIGS. 2-11).

S. aureus

S. aureus is sensitive to honeybee venom alone at low concentrations. It was important, therefore, to find the maximum dose of honeybee venom for which no effects were demonstrated. This concentration was approximately 2 ug/ml. Therefore, for all antibiotic/HBV combinations with S. aureus, the venom doses for the checkerboard titration system were 0, 2, 4, 8, and 16 ug/ml (Tables A-1 through A-3). FIG. 2 demonstrates the effects of these dosages of honeybee venom when used alone as an antibacterial compound.

Figure 3:
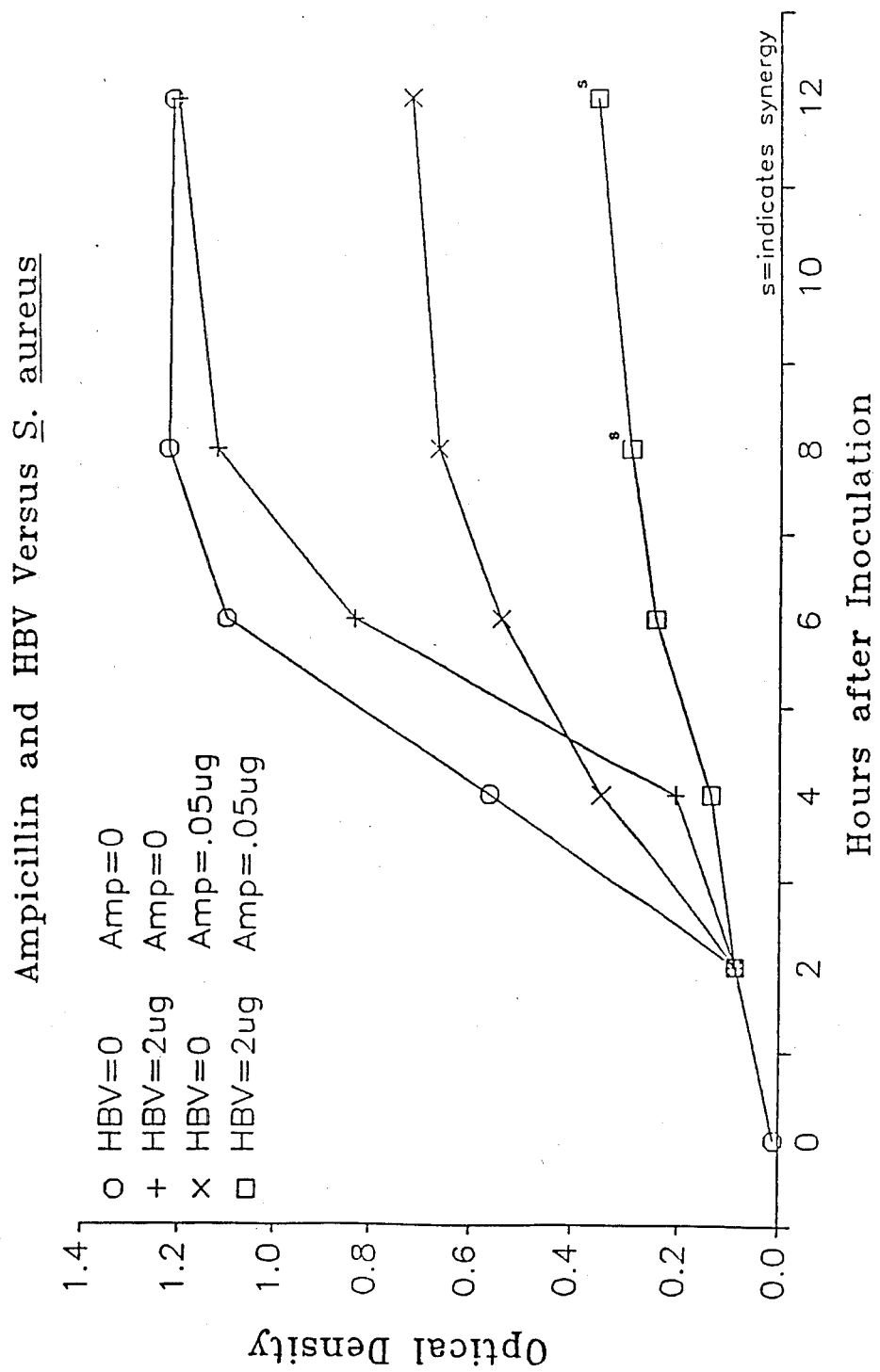

S. aureus versus Ampicillin/HBV. The final concentrations of ampicillin in tubes of the checkerboard system were 0, 0.05, 0.1, 0.2, and 0.4 ug/ml. FIG. 3 shows the results of the ampicillin/HBV combination using 2 ug/ml HBV and 0.05 ug/ml ampicillin. No synergy is seen at the 4 or 6 hour points; however, at both the 8 and 12 hour time points, it is evident that the interaction curve is much lower than would be predicted from the sum of the effects caused by ampicillin and HBV alone. Statistical analysis shows that at both time points, the summation $(-X+A+V-AV)$ is significantly greater than zero.

Figure 4:
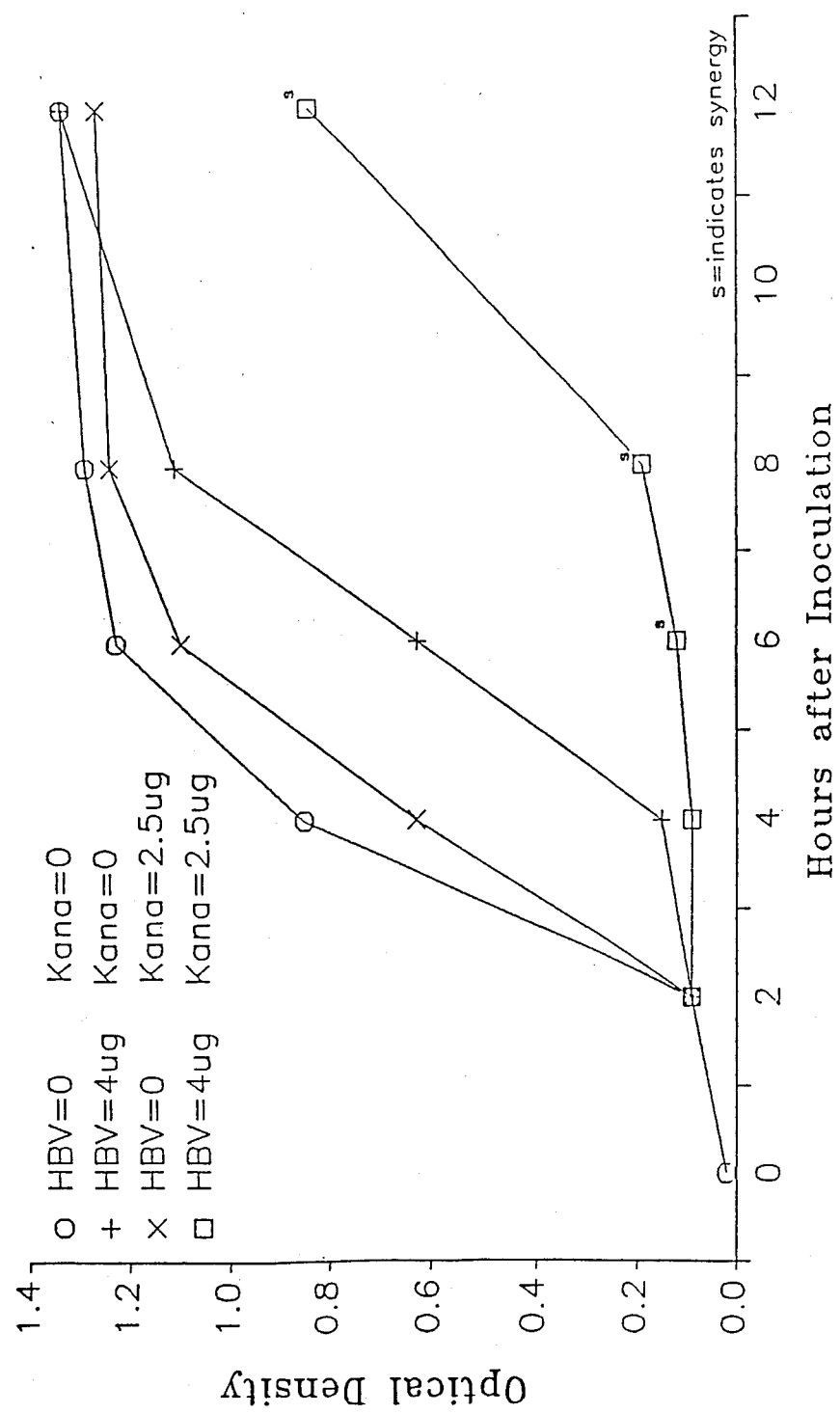

S. aureus versus Kanamycin/HBV. The final concentrations of kanamycin selected for testing S. aureus in the checkerboard system were 0, 1.25, 2.50, 5.0, and 10.0 ug/ml (Table A-2). FIG. 4 depicts the family of curves demonstrating the greatest contrast between control and interaction curves. In the experiment, synergy first becomes demonstrable near the 6 hour time point and is clearly seen by the 8 hours of incubation. At 12 hours, the cultures appear to have escaped the effects of the combined dose and the synergistic effect is lost since growth becomes limited by other (nutritional) factors in the medium. (This growth limitation is demonstrated by the control curve.) Despite the 12 hour growth restriction, statistical analysis of the data at 6, 8, and 12 hours suggest synergistic interaction between kanamycin and HBV in this assay.

Figure 5:
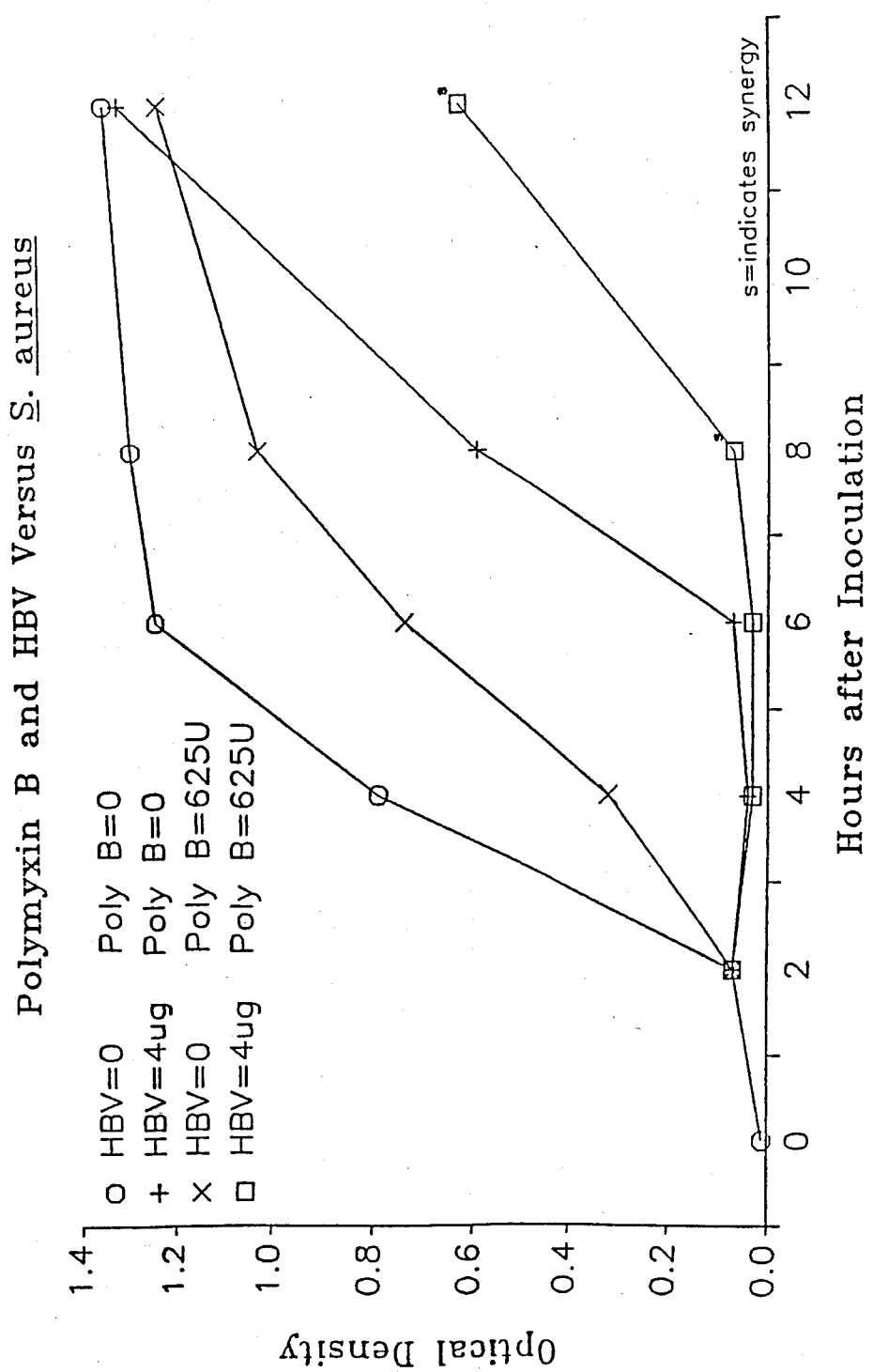

S. aureus versus Polymyxin B/HBV. The final concentrations of polymyxin B in these experiments were 0, 312, 624, 1250, and 2500 U/ml (Table A-3). Synergy was observed with 4 ug/ml HBV and 625 U/ml polymyxin B (FIG. 5). At both 8 and 12 hours of incubation, synergy is demonstrated by the interaction curve.

E. coli

Honeybee venom was not inhibitory alone to E. coli at the levels required to demonstrate synergy (Tables A-4 through A-6), thus, toxicity was not the limiting factor for HBV in the checkerboard assay with E. coli. However, experimental conditions limited the upper concentration of HBV at approximately 40 ug/ml; concentrations greater than this caused precipitation of medium components. Therefore, the final concentrations of HBV used in the checkerboard assays with E. coli were 0, 5, 10, 20, and 40 ug/ml.

Figure 6:
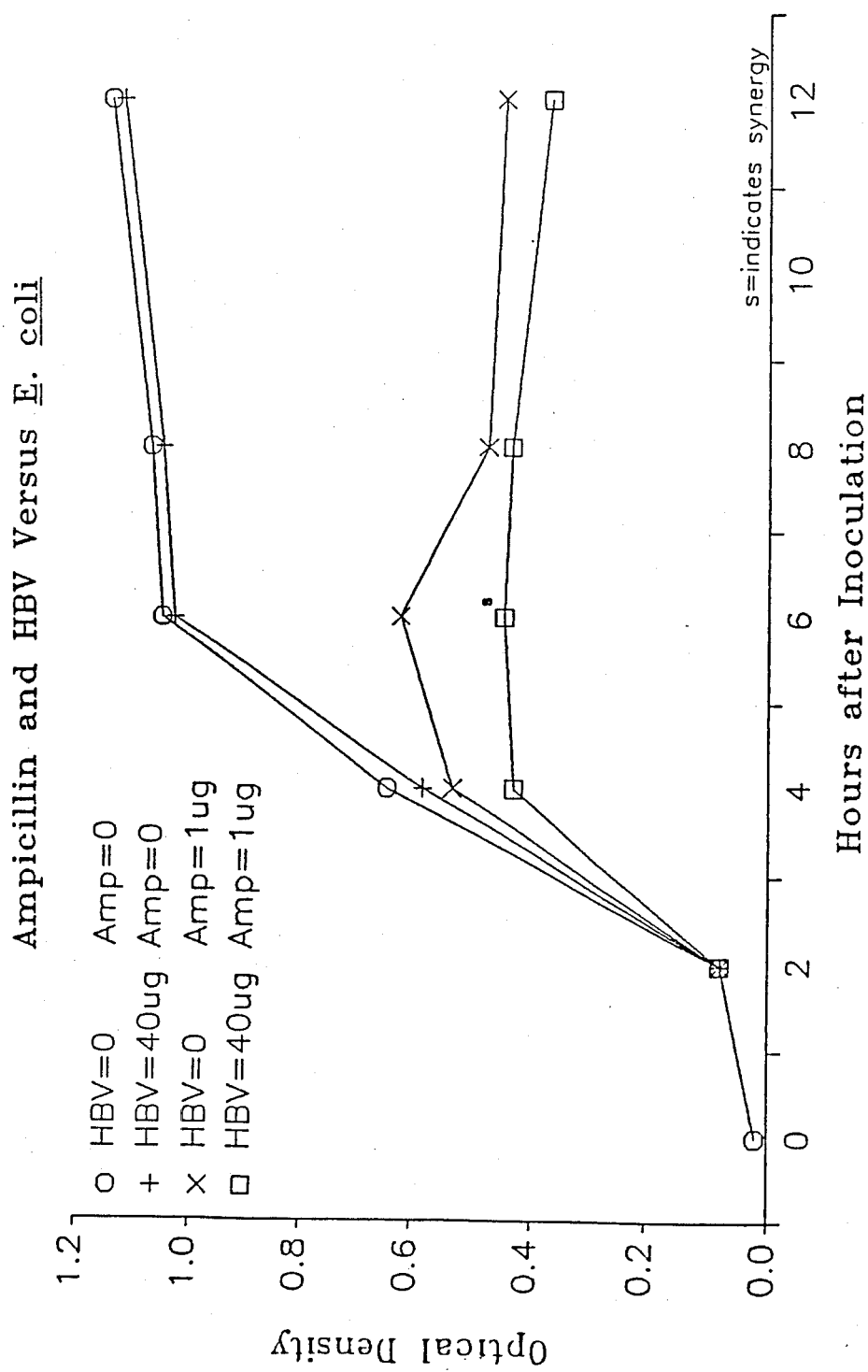

E. coli versus Ampicillin/HBV. The final concentrations of ampicillin selected for use in the E. coli checkerboard titration were 0.5, 1, 2, and 4 ug/ml (Table A-4). Synergy was less dramatic in all families of curves evaluated than for any of the above experiments. There was evidence of synergy only in the 40 ug/ml HVV-1 ug/ml ampicillin combination and only at the 6 hour time point (FIG. 6).

Figure 7:
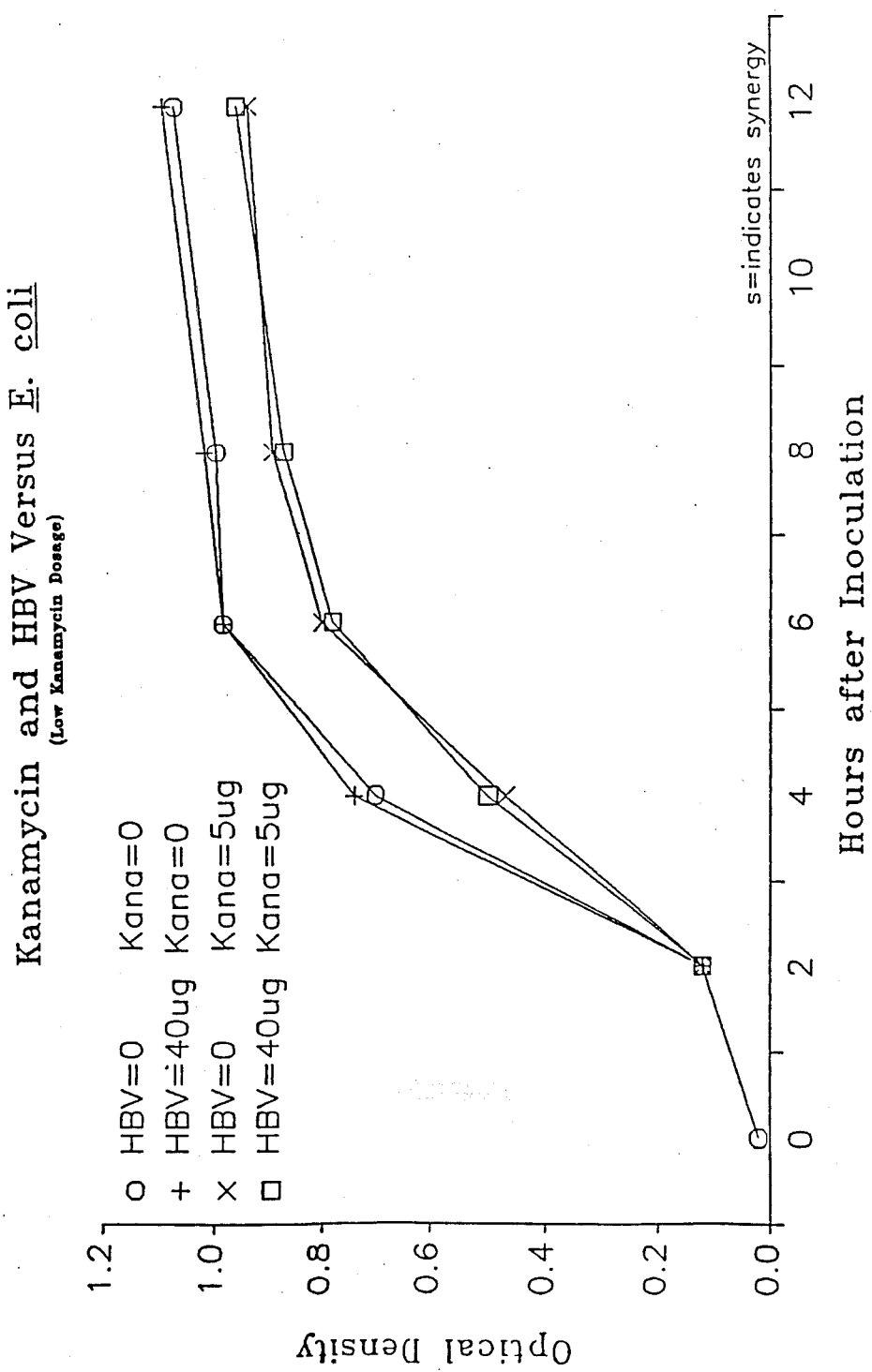

E. coli versus Kanamycin/HBV. The final concentrations of kanamycin selected for the checkerboard assay were 0, 5, 10, 20, and 40 ug/ml (Table A-5). FIG. 7 shows the effects of honeybee venom with a minimally effective dose of kanamycin. In this situation, only the 8 hour time point shows synergy. Regardless of the HBV dose, no synergy was seen in any of the other combinations of HBV with low doses of kanamycin.

Figure 8:
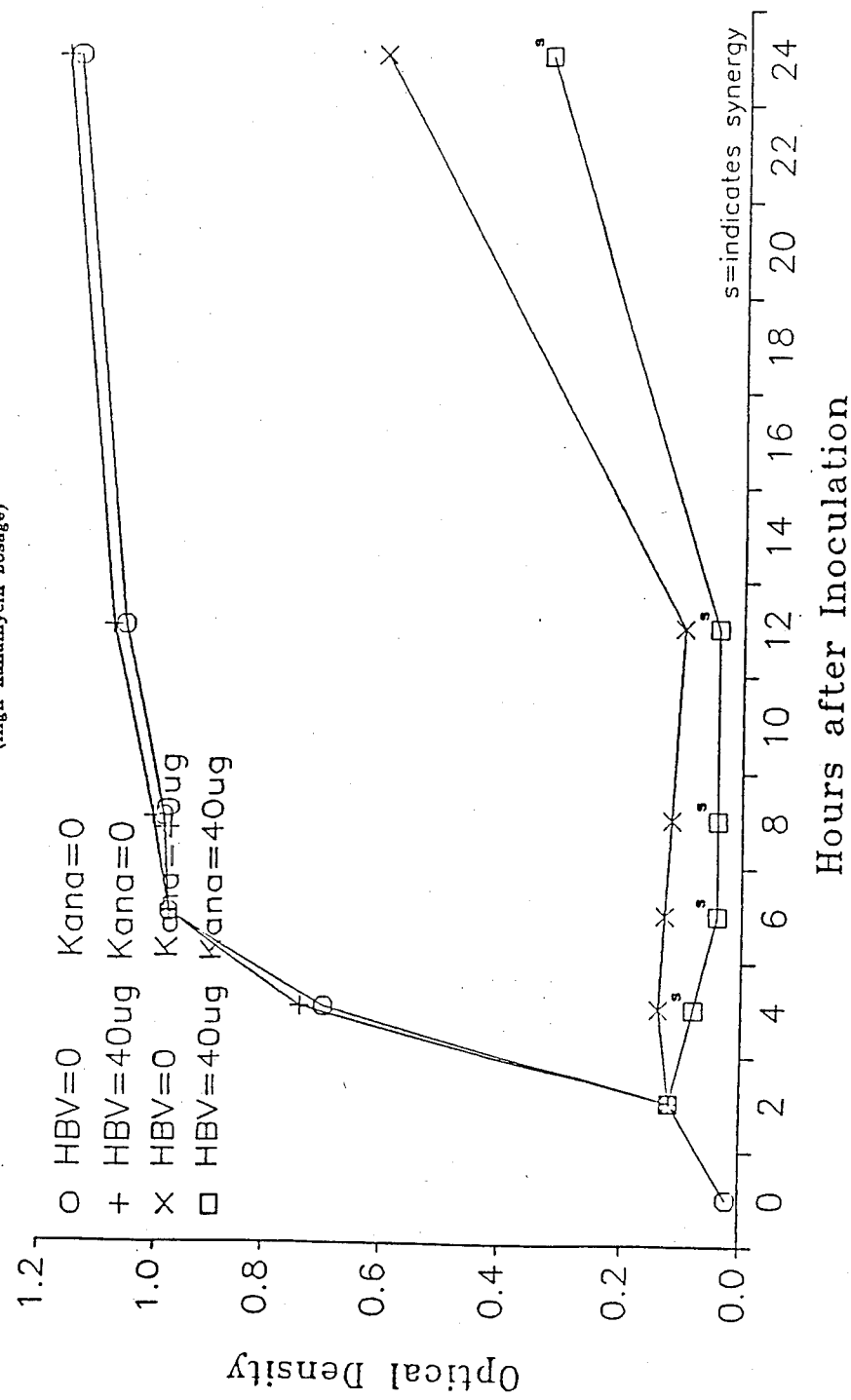

FIG. 8 shows a higher dose of kanamycin with HBV on E. coli. Here, synergism is statistically proven at all time points after 2 hours.

Figure 9:
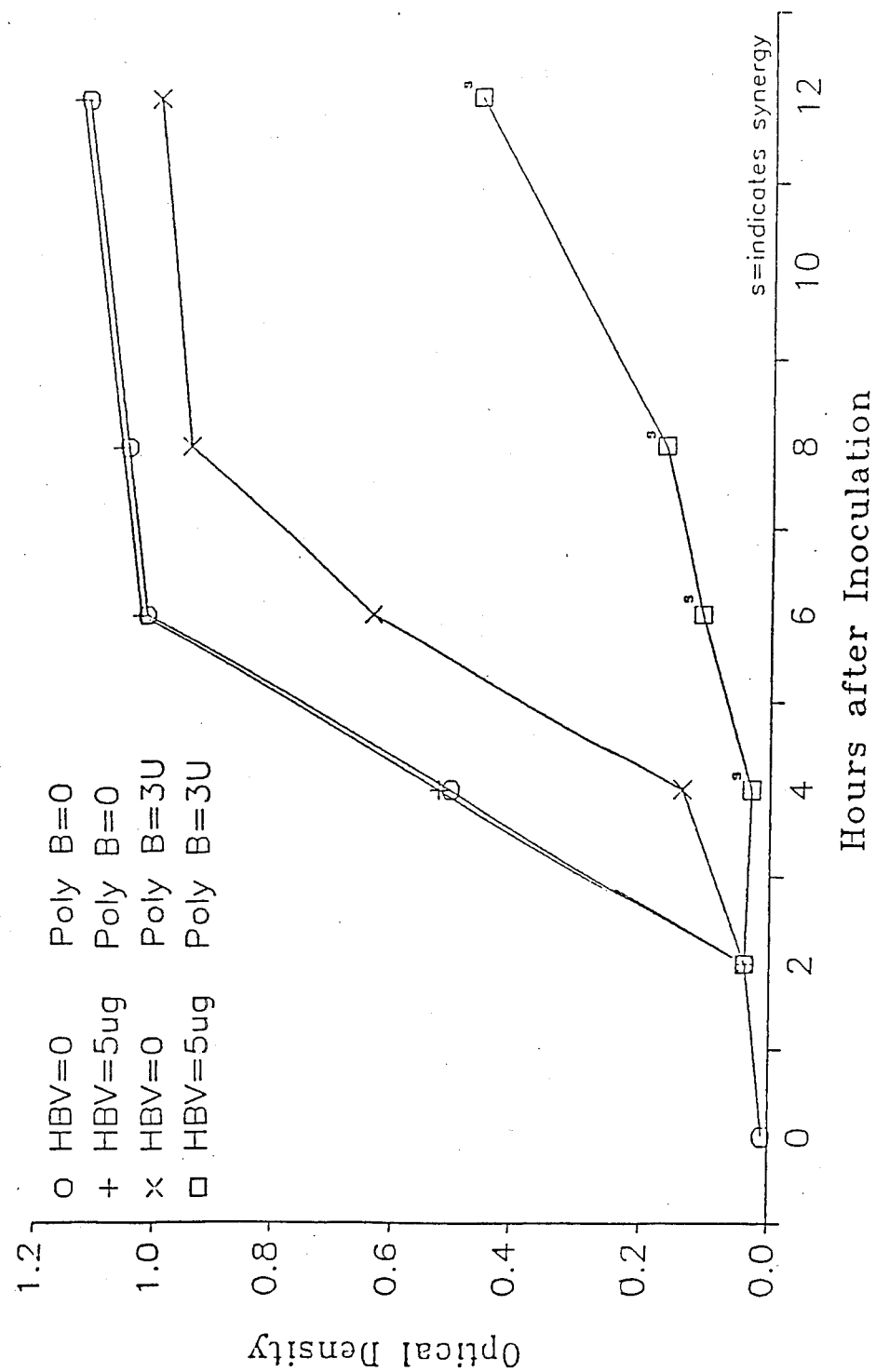

E. coli versus Polymyxin B/HBV. The final concentrations of polymyxin B in the checkerboard titrations were 0, 1.5, 3, 6, and 12 U/ml (Table A-6). The combination of 3 U/ml polymyxin B and 5 ug/ml HBV gave the most dramatic illustration of synergism (FIG. 9). Synergy is evident at all time points during the treatment and the differences between the observed and the predicted values are large.

Kanamycin Resistant S. aureus

A Kanamycin resistant S. aureus, obtained by the selection of spontaneous mutants, was assayed to evaluate the effect of HBV on drug resistant bacteria. A kanamycin resistant S. aureus was desirable because some synergy was seen for all antibiotics with this organism, and because synergistic effects were most easily seen with kanamycin.

No difference was found in the resistant strain's susceptibility to HBV, thus the venom concentrations in the checkerboard assays were the same as for the parent strain, 0, 2, 4, 8, and 16 ug/ml (Tables A-7 through A-9). It was noted that under identical conditions, the resistant strain had a slower growth rate than the parent strain, therefore, comparing optical density readings between experiments on the two different strains is not meaningful.

Kanamycin Resistant *S. aureus* versus Ampicillan/HBV

Figure 10:
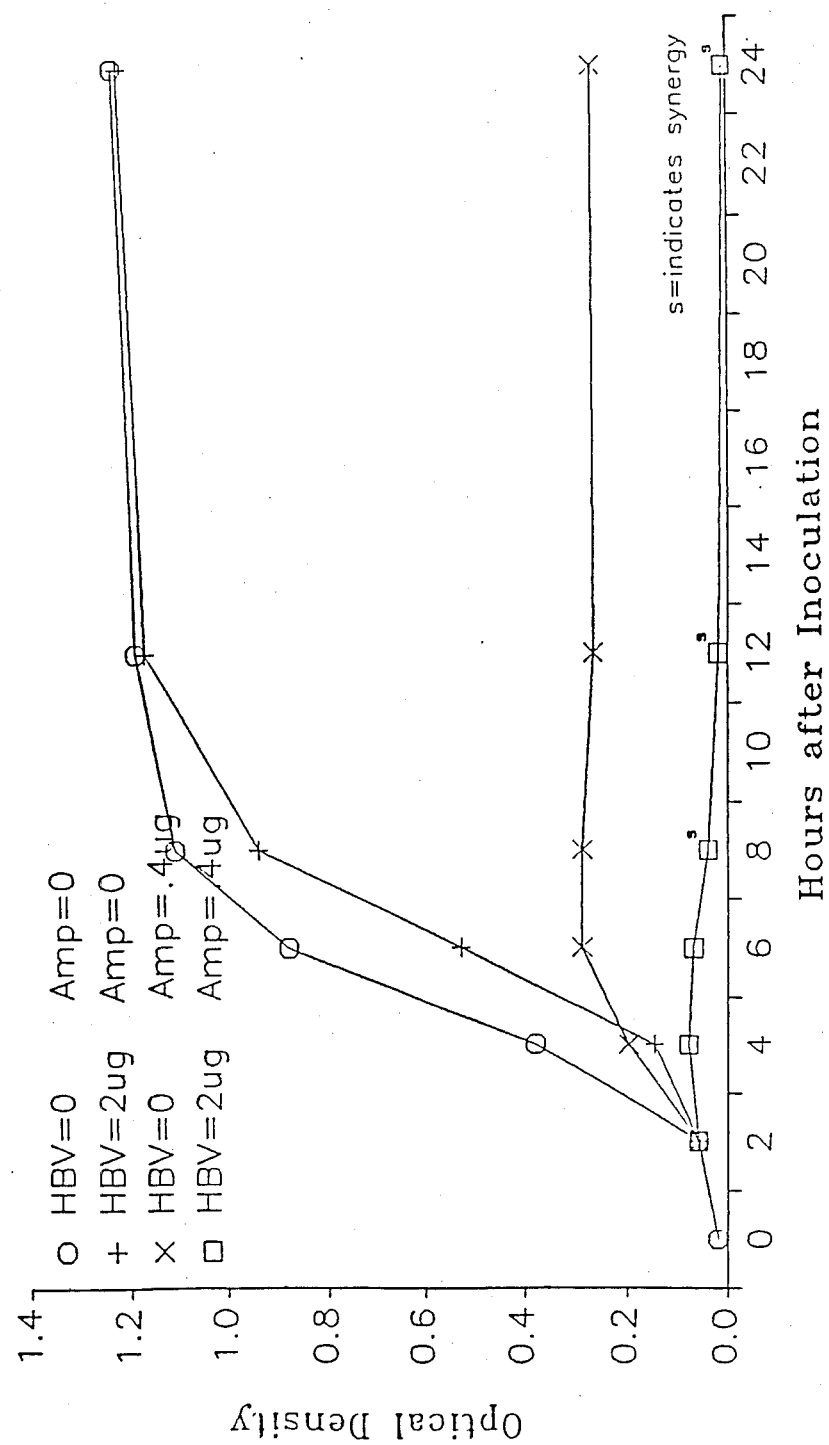

The final concentrations of ampicillin used in this checkerboard assay were the same as for the parent *S. aureus*, 0, 0.05, 0.1, 0.2, and 0.4 ug/ml (Table A-7). Whether due to the slower growth rate or the resistance factor, the effects seen with this strain were not completely analogous to the parent strain. The best evidence of synergy was seen at a higher ampicillin concentration than for the parent. Due to the slower growth rate, a longer growth period was considered. FIG. 10 shows the interaction of 2 ug/ml HBV and 0.4 ug/ml ampicillin. Statistical evaluation of the data shows synergy at the 8, 12, and 24 hour time points.

Kanamycin Resistant *S. aureus* versus Kanamycin/HBV

Figure 11:
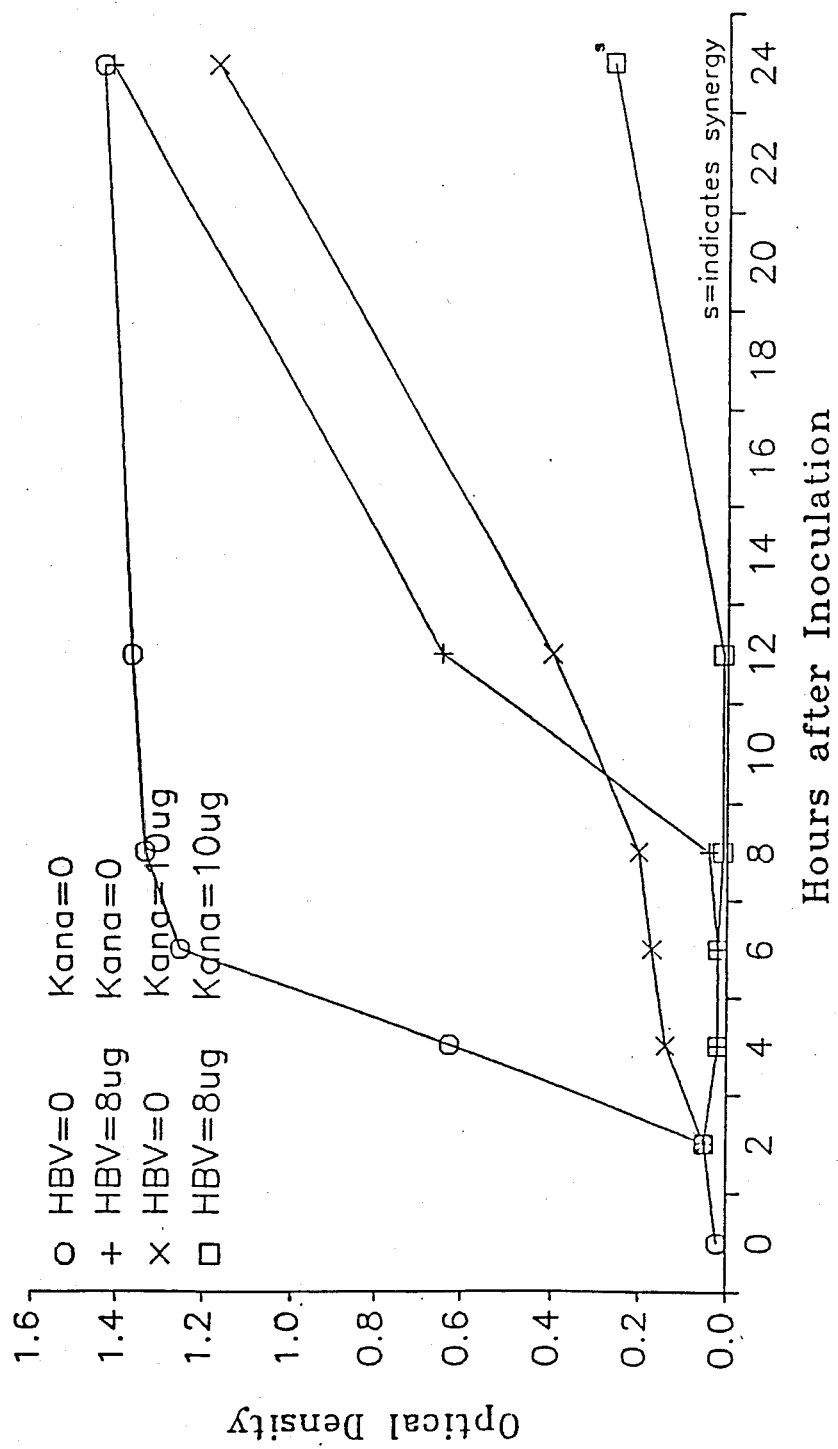

The dosage of kanamycin required to reduce the growth rate of the kanamycin resistant strain of *S. aureus* was approximately four times higher than the dose required by the parent strain. The checkerboard assay range for the kanamycin resistant *S. aureus* was 0, 5, 10, 20, and 40 ug/ml of kanamycin (Table A-8). Again, the slow growth rate made it necessary to consider a longer growth period. The combination of 8 ug/ml honeybee venom and 10 ug/ml kanamycin is shown in FIG. 11. Although the dose of kanamycin used is twice as high as the dose needed for the parent *S. aureus*, it remains effective twice as long in the presence of honeybee venom. Synergy was observed only after 12 hours and was proven to be significant only at the 24 hour time point.

Kanamycin Resistant *S. aureus* versus polymyxin B/HBV

Figure 12:
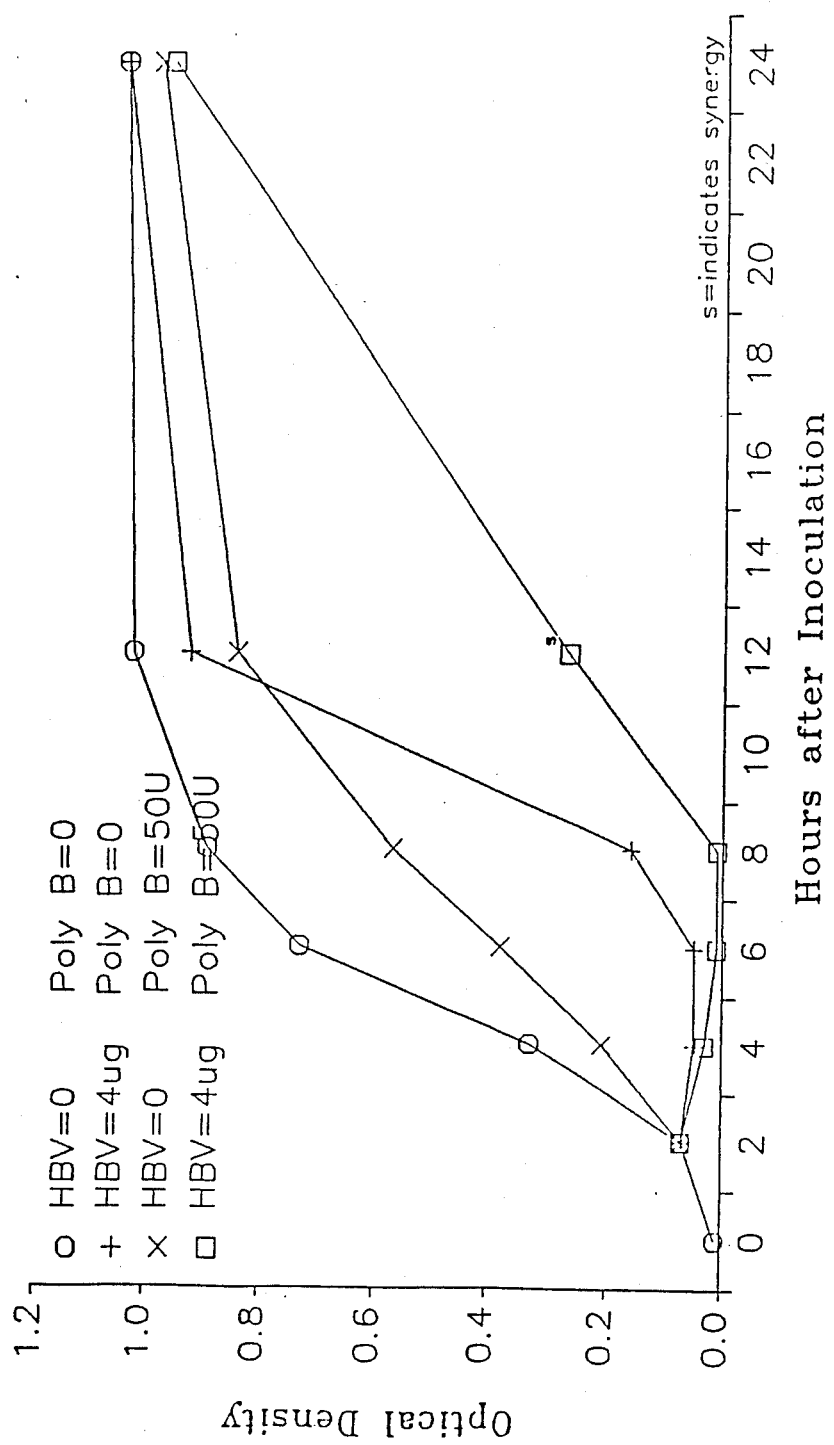

It was interesting to note that this mutant, selected for increased resistance to kanamycin, became more susceptible to polymyxin B than the parent strain. The polymyxin B doses used for the checkerboard assay was 0, 12.5, 25, 50, and 100 U/ml (Table A-9), wereas the polymyxin B dose range used for assaying the parent strain was between 312 and 2500 U/ml. FIG. 12 shows kanamycin resistant *S. aureus* versus 50 U/ml Polymyxin B and 4 ug/ml HBV. Synergy was shown at the 12 hour time point.

MIC Assays of Antibiotics With and Without HBV

The results of a preliminary survey of the effect of HBV on the MIC of antibiotics for eight gram-positive bacteria and four gram negative bacteria are shown in Table 4 and Table 5 respectively. Despite the apparent inadequacies of the assay system, definite trends were seen in the results of the survey. Synergy was strongly suggested where observations within a single MIC assay showed that identical doses of HBV affected some antibiotic MIC's while not affecting others. In Tables 4 and 5, a (+) was used to denote a decrease of more than one twofold dilution of the MIC of an antibiotic in the presence of HBV. A (−) indicates no difference or only a single dilution step variation (judged to be the variation of the assay) in the MIC of an antibiotic with HBV present.

Table 4 shows the results of several gram-positive organisms. The results indicate that trends exist within the species tested. For example, *S. aureus* appears to show synergy with all antibiotic/HBV combinations, while *S. epidermidis* shows consistent synergistic results only with the cephalothin/HBV combination and sporatic results with other antibiotic/HBV combinations. The one *Streptococcus faecalis* strain that was tested reflects none of the same synergistic trends shown by the two *staphylocuccus* organisms.

The data in Table 5 lists the results of four *E. coli* strains in the MIC assay system. Definite patterns of synergy are seen with each of the beta-lactam antibiotics (ampicillin, carbenicillin, and piperacillin) included in the MIC assay system. Also, the MIC of the aminoglycosides gentimicin and amikacin were lowered in every instance except one. The MIC of cefoxitin was also lowered by HBV in all *E. coli* assays.

MELITTIN PURIFICATION AND TESTING

Chromatography of Honeybee Venom

Figure 13:
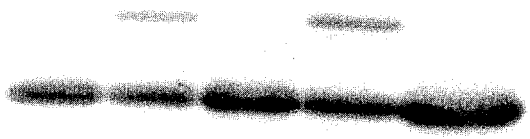

Purification of melittin on Sephadex G-50 gave well defined, base-line resolved peaks. The void volume was 100 ml and the melittin fraction eluted between 200 and 230 mls after the void volume. Approximately 65 ug of the initial 100 ug sample were recovered in fractions 200 to 230. These fractions were pooled and were checked for purity by polyacrylamide gel electrophoresis. FIG. 13 shows the electrophoresis results of 100 $\mu g$ of protein from the pooled fractions 200–230. Comparison of the relative mobility of this band to the relative mobilities of electrophoretically separated HBV components identified melittin as the only component of fractions 200–230 detectable in this separation.

Testing Melittin for Antibacterial Activity

Equivalent doses of melittin and whole honeybee venom were compared for antibacterial activity in combination with and without antibiotic (Table A-10). Since *S. aureus* was susceptible to HBV at levels used in the above assays, this organism was chosen to test the melittin fraction's activity. Kanamycin was chosen to evaluate the synergistic activity of the fraction, because the interaction curve seen in the above testing of *S. aureus* versus this antibiotic with HBV reflected synergy at all time points.

The Antibacterial Activity of Melittin. The results melittin versus whole HBV are shown in FIG. 14. No significant differences were observed in the antibacterial activity of whole HBV and the melittin fraction. For each time point represented in FIG. 14, the optical densities of the HBV curve and the melittin curve are statistically equal.

The Synergistic Activity of Mellitin with Kanamycin. FIG. 15 compares the antibacterial activities of equivalent doses of the melittin fraction and whole HBV venom in combination with equal doses of Kanamycin. None of the optical densities at any time point on the two curves are significantly different. Moreover, ignoring statistical evaluations, the interaction curve representing the melittin fraction is actually slightly lower at all time points than the interaction curve representing whole HBV. Thus, if the time points on both curves were accepted as the true means, the final conclusion would be that the melittin fraction is actually more active than whole HBV.

Interpretation of Checkerboard of Assay Results

The results of the checkerboard assays clearly demonstrate synergism between antibiotics and honeybee venom. FIG. 2 illustrated the effects of various doses of honeybee venom on *S. aureus* without antibiotics. It can be seen in this Figure that the addition of high doses of venom, such as 8 or 16 ug/ml, to the growing cultures actually lowered the optical density of the culture. This indication of cell lysis is evidence that honeybee venom is actually bactericidal. The mechanism of this bactericidal activity and its contribution to the synergy seen with antibiotics is not known. The varied results of the checkerboard titration assays suggest that several different synergistic mechanism may be functioning in these experiments.

Questions may arise on the large standard deviations seen at some time points in the data tables. This variability in general is due to the sharp slope of the growth rate when the bacteria are in log phase. Time points taken in mid-log phase will have a much larger difference in optical density with time than will time points taken during a slower growth period. Thus, uncontrollable, small variations in sampling intervals could cause larger variations in optical density readings at time points during logarithmic growth. Since cultures are split during log phase into the various treatment groups, variations are even more noticeable between experiments. This type of error is taken into consideration, however, in the statistical evaluation procedure. By using a large sample number (15), estimation ranges for the means of the time points were made narrow enough to statistically evaluate the differences in these means.

Although melittin was only tested initially as the synergistic component of HBV in combination with one antibiotic with one bacterial strain, for the purpose of discussing possible mechanisms it has been assumed that melittin is the synergistic honeybee venom component in each of the bacterial-antibiotic-HBV combinations tested.

Apparent Increased Dosage

In most cases, honeybee venom seems to boost the initial effectiveness of the antibiotic, which is indicated by an increased ability to lower the bacterial growth rate immediately upon addition of the two compounds. This type of cooperativeness was most demonstrable with *E. coli* versus HBV and polymyxin V (FIG. 9). At the first time point after addition of the two compounds, synergism is apparent and it continues as the culture progresses through log phase. These results suggest that low, noneffective doses of antibiotics may be made effective with the addition of HBV.

The boosted dosage effect described above is the type of synergy seen in most of the experimental combinations that were tested. This type of effect could be explained by the action of melittin through several different mechanisms: (1) altering the solubility properties of the antibiotic molecules, (2) increasing the permeability of the bacterial membrane, and (3) increasing the effectiveness of the antibiotic molecules at their active sites.

Altered Solubility Properties of the Antibiotics. The melittin could increase antibiotic efficacy by allowing it to be more easily transported into the bacterial cell. The direct interaction of melittin with antibiotics molecules, making the molecules less polar or more hydrophobic might allow passive transport through the bacterial membranes. The amphipatic nature and basicity of melittin makes it a likely candidate for such a function and adds to the plausibility of this mechanism. This type of mechanism would be similar to the facilitated diffusion of potassium ions with valinomycin.

Increased Membrane Permeability. The apparent dosage of an antibiotic could also be increased by reducing penetration barriers of the bacterium.

Although this role as a channel-forming peptide is easily supported, it cannot be the only function of melittin that is involved in the antibacterial synergy. Increased transport across membranes fails to explain why melittin alone is more effective on gram positive organisms which have less of a membrane barrier.

Increased Antibiotic Specific Activity. A third possible mechanism for synergistic interactions proposes the direct interaction of melittin and the antibiotic to make the antibiotic more effective once it reaches the active site. A more specific example is the possible interaction with kanamycin. Once kanamycin reaches the 30S ribosome, a melittin-kanamycin complex may have a greater affinity for the active site than unbound kanamycin (after all, melittin is a basic molecule, like nucleic acids), or the melittin-kanamycin complex may be more effective in sterically blocking transfer-RNA's from the ribosome due simply to the size of the complex.

Increased Active Life of Antibiotics

In several cases, it was difficult to detect an increase in effectiveness of the antibiotics with the addition of honeybee venom (melittin) until late in the growth period. In these cases it appeared that the melittin caused an increase in the duration of the antibiotic's effect. This effect was seen that the kanamycin resistant *S. aureus* treated with kanamycin/HBV. Shown in FIG. 9 is a relatively high dose of HBV, the reason being that no synergism was seen with lower doses. Thus, although it is difficult in FIG. 9 to rule out synergy at the early time points due to the effectiveness of the HBV alone, lower doses of HBV showed no synergy with kanamycin at these early time points. A synergistic effect is noted, however, at the 24 hour time point. Two explanations for this type of delayed effect are suggested: (1) elimination of resistant mutants or (2) extension of the antibiotic's half-life.

Decreased Probability for the Selection of Resistant Strains. If both the honeybee venom and antibiotic are present in a bacterial culture at bacteristatic doses, the probability that a resistant bacterium will survive the combined treatment is equal to the product of the probabilities that one would exist and survive either treatment. This would appear as a delayed synergistic effect, as it would take many generations for the mutants to multiply to a level detectable by increased OD readings. Mutant selection would be characterized as a sporadic occurrence of a drastically higher OD reading among replicate samples which would be reflected in the standard deviation of the treatment. For example, when the effects of HBV treatment alone on the kanamycin resistant *S. aureus* with kanamycin was evaluated, the mean OD of the 12 hour time point on the venom control curve was 0.65 with one standard deviation of 0.51 (Table A-8), indicating highly varied readings at this time point. Thus, it could be very possible that the synergistic effect seen here at the 24 hour time point is the result of suppression of HBV venom resistant mutants.

Increased Antibiotic Stability. Not to be excluded from possible mechanism is protection of the antibiotic from decomposition. A common technique in increasing antibiotic efficacy is to structurally alter the antibiotic to make it more stable in solution or resistant to enzymatic attack. These types of modifications account for many of the derivatives of the penicillin family of antibiotics. For example, penicillin V has a phenoxymethyl substitution which provides steric hinderance, protecting the antibiotic's beta-lactam ring from enzymatic attack (Volk, 1978c). Such substitutions may also prevent this end of the molecule from cyclization with the beta-lactam ring making the molecule more resistant to acid hydrolysis. These types of modifications would also produce a synergic effect demonstrable only at bacteristatic doses, since the antibiotic would not be any more effective initially and the prolonged life span of the antibiotic would be evident only if the bacterial culture had not reached a nutritionally limiting OD at that time. If, however, HBV could cause such a modification, more consistent results among replicate samples would be expected.

Evaluation of M

TABLE 4-continued

The effect of 4 ug/ml HBV on the MIC's of eleven antibiotics on eight gram-positive organisms.

| | A[1] | B[2] | | | | | | C[3] |
|---|---|---|---|---|---|---|---|---|
| | QC[4] | 51072 | 39817 | 5905 | 5907 | 7905 | 7908 | Sf |
| Methicillin | + | + | + | − | − | + | + | − |
| Ampicillin | + | + | + | − | − | + | + | − |
| Cephalothin | + | + | + | + | + | + | + | − |
| Gentamicin | + | + | + | − | − | − | + | − |
| Kanamycin | + | + | − | − | − | + | + | − |
| Erythromycin | + | + | − | − | − | − | + | − |
| Chloramphenicol | + | + | − | − | − | − | + | + |
| Clindamycin | + | + | − | − | − | − | + | − |
| Tetracycline | + | + | − | − | − | − | + | − |
| Vancomycin | + | + | − | − | − | − | + | − |

[1] Group "A" = two strains of *S. aureus*
[2] Group "B" = five strains of *S. epidermidis*
[3] "C" = a strain of *Streptococcus faecalis*
[4] QC = a *S. aureus* strain used for routine quality control testing of this assay system.
[5] A (−) indicates a MIC decrease of less than two dilution steps.
[6] A (+) indicates a MIC decrease greater than or equal to two dilution steps.

TABLE 5

The effect of 4 ug/ml HBV on the MIC's of eleven antibiotics on four strains of *E. coli*.

| | E. coli strain | | | |
|---|---|---|---|---|
| | QC[1] | 1173 | 4302 | 19033 |
| Ampicillin | +[2] | + | + | + |
| Carbenicillin | + | + | + | + |
| Piperacillin | + | + | + | + |
| Cephalothin | −[3] | − | − | − |
| Cefoxitin | + | + | + | + |
| Cefamandole | − | − | − | − |
| Moxalactam | − | + | − | − |
| Amikacin | + | + | + | + |
| Gentimicin | + | − | + | + |
| Chloramphenicol | − | − | − | + |
| Tobramycin | − | − | − | − |

[1] QC is a strain of *E. coli* used for routine quality control testing of this assay system.
[2] A (+) indicates a MIC decrease greater than or equal to two dilution steps.
[3] A (−) indicates a MIC decrease of less than two dilution steps.

TABLE 6

*Staphylococcus aureus*
Rifampin = .01 ug/ml or .001 ug/ml
Honey Bee Venom = 4 ug/ml
hours after innoculation

| | 0 | 2 | 4 | 6 | 8 | 12 |
|---|---|---|---|---|---|---|
| Control | .046 | .080 | .850 | 1.17 | 1.26 | 1.34 |
| | .046 | .073 | .815 | 1.16 | 1.26 | 1.32 |
| | .046 | .073 | .815 | 1.16 | 1.26 | 1.35 |
| AVERAGE | .046 | .075 | .827 | 1.16 | 1.26 | 1.34 |
| Rifampicin .01 ug/ml | .046 | .056 | .140 | .372 | 1.07 | 1.32 |
| | .046 | .054 | .068 | .156 | .625 | 1.34 |
| | .046 | .058 | .112 | .304 | 1.00 | 1.30 |
| AVERAGE | .046 | .056 | .107 | .277 | .898 | 1.32 |
| Rifampicin .001 ug/ml | .046 | .081 | .855 | 1.18 | 1.27 | 1.34 |
| | .046 | .064 | .765 | 1.16 | 1.26 | 1.34 |
| | .046 | .072 | .800 | 1.17 | 1.26 | 1.34 |
| AVERAGE | .046 | .072 | .807 | 1.17 | 1.26 | 1.34 |
| Venom 4 ug/ml | .046 | .062 | .158 | .705 | 1.20 | 1.29 |
| | .046 | .063 | .284 | .875 | 1.22 | 1.31 |
| | .046 | .059 | .068 | .312 | 1.09 | 1.29 |
| AVERAGE | .046 | .061 | .170 | .631 | 1.17 | 1.30 |
| Rifampicin .01 ug/ml + Venom 4 ug/ml | .046 | .053 | .078 | .156 | .665 | 1.33 |
| | .046 | .055 | .078 | .162 | .640 | 1.32 |
| | .046 | .056 | .062 | .092 | .332 | 1.32 |
| AVERAGE | .046 | .055 | .073 | .137 | .546 | 1.32 |
| Rifampicin .001 ug/ml + Venom 4 ug/ml | .046 | .066 | .068 | .242 | 1.08 | 1.32 |
| | .046 | .063 | .109 | .485 | 1.19 | 1.34 |
| | .046 | .067 | .087 | .381 | 1.16 | 1.33 |

TABLE 6-continued

*Staphylococcus aureus*
Rifampin = .01 ug/ml or .001 ug/ml
Honey Bee Venom = 4 ug/ml
hours after innoculation

| | 0 | 2 | 4 | 6 | 8 | 12 |
|---|---|---|---|---|---|---|
| AVERAGE | .046 | 0.65 | .088 | .369 | 1.14 | 1.33 |

TABLE 7

*Pseudomonas aeruginosa*
Rifampicin = 10 ug/ml or 20 ug/ml
Honey Bee Venom = 40 ug/ml
hours after innoculation

| | 0 | 2 | 4 | 6 | 8 | 12 |
|---|---|---|---|---|---|---|
| Control | .033 | .062 | .735 | 1.00 | 1.02 | 1.00 |
| | .033 | .069 | .755 | .955 | 1.00 | .990 |
| | .033 | .068 | .775 | .950 | .990 | .900 |
| AVERAGE | .033 | .066 | .755 | .968 | 1.00 | .963 |
| Venom 40 ug/ml | .033 | .078 | .690 | .890 | .960 | .980 |
| | .033 | .087 | .687 | .870 | .960 | .980 |
| | .033 | .058 | .685 | .880 | .953 | .950 |
| AVERAGE | .033 | .074 | .685 | .880 | .953 | .970 |
| Rifampicin 10 ug/ml | .033 | .074 | .630 | .830 | .885 | .842 |
| | .033 | .084 | .672 | .850 | .895 | .850 |
| | .033 | .082 | .640 | .830 | .865 | .832 |
| AVERAGE | .033 | .080 | .647 | .837 | .882 | .841 |
| Rifampicin 20 ug/ml | .033 | .053 | .375 | .660 | .730 | .730 |
| | .033 | .056 | .326 | .645 | .720 | .730 |
| | .033 | .063 | .380 | .700 | .760 | .745 |
| AVERAGE | .033 | .057 | .351 | .688 | .737 | .735 |
| Rifampicin 10 ug/ml + Venom 40 ug/ml | .033 | .084 | .452 | .805 | .860 | .861 |
| | .033 | .079 | .475 | .795 | .820 | .839 |
| | .033 | .078 | .490 | .820 | .860 | .880 |
| AVERAGE | .033 | .080 | .466 | .807 | .847 | .860 |
| Rifampicin 20 ug/ml + Venom 40 ug/nl | .033 | .065 | .180 | .410 | .580 | .620 |
| | .033 | .082 | .168 | .375 | .535 | .620 |
| | .033 | .058 | .168 | .373 | .525 | .612 |
| AVERAGE | .033 | .068 | .172 | .386 | .547 | .617 |

TABLE 8

*Escherichia coli*
Polymyxin B = 6.25 Units/ml and 3.125 Units/ml
Bumblebee Venom = 5 ug/ml and 20 ug/ml
(*Megabombus pennsylvanicus*)
hours after innoculation

| | 0 | 2 | 4 | 6 | 8 | 12 |
|---|---|---|---|---|---|---|
| Control | .030 | .688 | 1.04 | 1.05 | 1.14 | 1.23 |
| | .030 | .680 | 1.03 | 1.04 | 1.13 | 1.22 |
| | .030 | .683 | 1.02 | 1.04 | 1.13 | 1.22 |
| AVERAGE | .030 | .684 | 1.03 | 1.04 | 1.13 | 1.22 |
| BB Venom | .030 | .715 | 1.03 | 1.02 | 1.04 | 1.12 |
| | .030 | .712 | 1.03 | 1.04 | 1.04 | 1.14 |
| 5 ug/ml | .030 | .730 | 1.03 | 1.03 | 1.04 | 1.13 |
| AVERAGE BB Venom | .030 | .719 | 1.03 | 1.03 | 1.04 | 1.13 |
| | .030 | .672 | 1.03 | 1.03 | 1.04 | 1.13 |
| | .030 | .673 | 1.04 | 1.03 | 1.05 | 1.16 |
| 20 ug/ml | .030 | .688 | 1.04 | 1.03 | 1.06 | 1.13 |
| AVERAGE Pol B | .030 | .678 | 1.04 | 1.03 | 1.05 | 1.14 |
| | .030 | .654 | 1.03 | 1.03 | 1.04 | 1.12 |
| | .030 | .642 | 1.02 | 1.03 | 1.04 | 1.14 |
| 3.125 Units/ml | .030 | .652 | 1.02 | 1.03 | 1.04 | 1.14 |
| AVERAGE Pol B | .030 | .649 | 1.02 | 1.03 | 1.04 | 1.13 |
| | .030 | .022 | .102 | .710 | .960 | 1.03 |
| | .030 | .024 | .472 | .940 | .950 | 1.03 |
| 6.25 Units/ml | .030 | .022 | .180 | .830 | .970 | 1.04 |
| AVERAGE Pol B = | .030 | .023 | .251 | .827 | .960 | 1.03 |
| | .030 | .008 | .168 | .820 | 1.00 | 1.06 |
| 3.125 Units/ml BBV = 5 ug/ml | .030 | .008 | .250 | .910 | 1.02 | 1.06 |
| | .030 | .009 | .333 | .950 | 1.02 | 1.07 |
| AVERAGE Pol B = | .030 | .008 | .250 | .893 | 1.01 | 1.06 |
| 6.25 Units/ml | .030 | .008 | .012 | .008 | .009 | .013 |
| | .030 | .009 | .009 | .008 | .008 | .012 |
| BBV = 20 ug/ml | .030 | 011 | .009 | .008 | .008 | .013 |
| AVERAGE | .030 | .009 | .010 | .008 | .008 | .013 |

TABLE 9

*Escherichia coli*

Polymyxin B = 3.125 Units/ml
Yellowjacket Venom = 5 ug/ml
(*Vespula germanica*)
Baldfaced Hornet Venom = 5 ug/ml
(*Dolichovespula maculata*)
hours after innoculation

|  | 0 | 2 | 4 | 6 | 8 | 12 |
|---|---|---|---|---|---|---|
| Control | .038 | .526 | 1.03 | 1.07 | 1.08 | 1.12 |
|  | .038 | .522 | 1.04 | 1.07 | 1.08 | 1.12 |
| AVERAGE | .038 | .524 | 1.04 | 1.07 | 1.08 | 1.12 |
| Pol B | .038 | .477 | 1.03 | 1.07 | 1.08 | 1.14 |
| 3.125 U/ml | .038 | .482 | 1.03 | 1.07 | 1.08 | 1.14 |
| AVERAGE | .038 | .480 | 1.03 | 1.07 | 1.08 | 1.14 |
| YJ | .038 | .547 | 1.04 | 1.07 | 1.09 | 1.16 |
| 5 ug/ml | .038 | .550 | 1.04 | 1.07 | 1.08 | 1.14 |
| AVERAGE | .038 | .549 | 1.04 | 1.07 | 1.09 | 1.15 |
| BF | .038 | .552 | 1.04 | 1.08 | 1.08 | 1.16 |
| 5 ug/ml | .038 | .565 | 1.04 | 1.07 | 1.09 | 1.15 |
| AVERAGE | .038 | .559 | 1.04 | 1.08 | 1.09 | 1.16 |
| YJ 5 ug/ml | .038 | .028 | .183 | .945 | 1.08 | 1.14 |
| Pol B 5 U/ml | .038 | .029 | .098 | .850 | 1.06 | 1.12 |
| AVERAGE | .038 | .029 | .141 | .893 | 1.07 | 1.13 |
| BF 5 ug/ml | .038 | .027 | .118 | .890 | 1.08 | 1.13 |
| Pol B 5 U/ml | .038 | .023 | .096 | .840 | 1.06 | 1.10 |
| AVERAGE | .038 | .025 | .107 | .865 | 1.07 | 1.12 |

TABLE A-1

The checkerboard assay results of ampicillin and honeybee venom verus *S. aureus*.

| TIME | MEAN $A_{660}$ | S.D. | TIME | MEAN $A_{660}$ | S.D. |
|---|---|---|---|---|---|
| AMP = 0, HBV = 0 | | | AMP = 0, HBV = 2 | | |
| T0 | 0.013 | 0.002 | T0 | 0.013 | 0.002 |
| T2 | 0.085 | 0.018 | T2 | 0.085 | 0.018 |
| T4 | 0.573 | 0.178 | T4 | 0.213 | 0.135 |
| T6 | 1.102 | 0.159 | T6 | 0.844 | 0.311 |
| T8 | 1.223 | 0.101 | T8 | 1.119 | 0.193 |
| T12 | 1.213 | 0.307 | T12 | 1.198 | 0.306 |
| T24 | 1.329 | 0.069 | T24 | 1.295 | 0.208 |
| AMP = 0, HBV = 4 | | | AMP = 0, HBV = 8 | | |
| T0 | 0.013 | 0.002 | T0 | 0.013 | 0.002 |
| T2 | 0.086 | 0.018 | T2 | 0.085 | 0.018 |
| T4 | 0.065 | 0.040 | T4 | 0.026 | 0.019 |
| T6 | 0.217 | 0.181 | T6 | 0.014 | 0.012 |
| T8 | 0.671 | 0.412 | T8 | 0.027 | 0.036 |
| T12 | 1.147 | 0.317 | T12 | 1.028 | 0.273 |
| T24 | 1.278 | 0.165 | T24 | 1.291 | 0.119 |
| AMP = 0, HBV = 16 | | | AMP = 0.05, HBV = 0 | | |
| T0 | 0.013 | 0.002 | T0 | 0.013 | 0.002 |
| T2 | 0.085 | 0.018 | T2 | 0.085 | 0.018 |
| T4 | 0.025 | 0.011 | T4 | 0.355 | 0.073 |
| T6 | 0.007 | 0.004 | T6 | 0.552 | 0.195 |
| T8 | 0.006 | 0.004 | T8 | 0.689 | 0.146 |
| T12 | 0.077 | 0.173 | T12 | 0.736 | 0.135 |
| T24 | 0.857 | 0.576 | T24 | 0.760 | 0.114 |
| AMP = 0.05, HBV = 2 | | | AMP = 0.05, HBV = 4 | | |
| T0 | 0.013 | 0.003 | T0 | 0.013 | 0.002 |
| T2 | 0.085 | 0.004 | T2 | 0.083 | 0.017 |
| T4 | 0.142 | 0.039 | T4 | 0.045 | 0.025 |
| T6 | 0.260 | 0.142 | T6 | 0.041 | 0.033 |
| T8 | 0.296 | 0.196 | T8 | 0.035 | 0.032 |
| T12 | 1.372 | 0.093 | T12 | 0.131 | 0.307 |
| T24 | 1.647 | 0.063 | T24 | 0.840 | 0.251 |
| AMP = 0.05, HBV = 8 | | | AMP = 0.05, HBV = 16 | | |
| T0 | 0.013 | 0.002 | T0 | 0.013 | 0.002 |
| T2 | 0.085 | 0.018 | T2 | 0.085 | 0.018 |
| T4 | 0.026 | 0.021 | T4 | 0.025 | 0.009 |
| T6 | 0.012 | 0.012 | T6 | 0.006 | 0.004 |
| T8 | 0.008 | 0.007 | T8 | 0.007 | 0.004 |
| T12 | 0.009 | 0.004 | T12 | 0.008 | 0.005 |
| T24 | 0.331 | 0.395 | T24 | 0.013 | 0.004 |
| AMP = 0.1, HBV = 0 | | | AMP = 0.1, HBV = 2 | | |
| T0 | 0.013 | 0.002 | T0 | 0.013 | 0.002 |
| T2 | 0.085 | 0.018 | T2 | 0.083 | 0.017 |
| T4 | 0.257 | 0.043 | T4 | 0.124 | 0.068 |
| T6 | 0.248 | 0.061 | T6 | 0.109 | 0.057 |
| T8 | 0.155 | 0.059 | T8 | 0.056 | 0.025 |

TABLE A-1-continued

The checkerboard assay results of ampicillin and honeybee venom verus *S. aureus*.

| TIME | MEAN $A_{660}$ | S.D. | TIME | MEAN $A_{660}$ | S.D. |
|---|---|---|---|---|---|
| T12 | 0.095 | 0.033 | T12 | 0.034 | 0.015 |
| T24 | 0.347 | 0.178 | T24 | 0.259 | 0.229 |
| AMP = 0.1, HBV = 4 | | | AMP = 0.1, HBV = 8 | | |
| T0 | 0.013 | 0.002 | T0 | 0.013 | 0.002 |
| T2 | 0.085 | 0.018 | T2 | 0.085 | 0.018 |
| T4 | 0.042 | 0.026 | T4 | 0.022 | 0.016 |
| T6 | 0.031 | 0.030 | T6 | 0.007 | 0.006 |
| T8 | 0.026 | 0.021 | T8 | 0.005 | 0.004 |
| T12 | 0.272 | 0.534 | T12 | 0.011 | 0.013 |
| T24 | 0.511 | 0.552 | T24 | 0.246 | 0.497 |
| AMP = 0.1, HBV = 16 | | | AMP = 0.2, HBV = 0 | | |
| T0 | 0.013 | 0.002 | T0 | 0.013 | 0.002 |
| T2 | 0.085 | 0.018 | T2 | 0.085 | 0.018 |
| T4 | 0.026 | 0.013 | T4 | 0.202 | 0.038 |
| T6 | 0.007 | 0.005 | T6 | 0.112 | 0.026 |
| T8 | 0.006 | 0.004 | T8 | 0.052 | 0.016 |
| T12 | 0.007 | 0.004 | T12 | 0.037 | 0.009 |
| T24 | 0.011 | 0.004 | T24 | 0.042 | 0.008 |
| AMP = 0.2, HBV = 2 | | | AMP = 0.2, HBV = 4 | | |
| T0 | 0.013 | 0.002 | T0 | 0.013 | 0.002 |
| T2 | 0.086 | 0.018 | T2 | 0.085 | 0.018 |
| T4 | 0.103 | 0.065 | T4 | 0.045 | 0.024 |
| T6 | 0.079 | 0.050 | T6 | 0.029 | 0.022 |
| T8 | 0.036 | 0.027 | T8 | 0.021 | 0.015 |
| T12 | 0.026 | 0.021 | T12 | 0.013 | 0.006 |
| T24 | 0.069 | 0.179 | T24 | 0.011 | 0.008 |
| AMP = 0.2, HBV = 8 | | | AMP = 0.2, HBV = 16 | | |
| T0 | 0.013 | 0.002 | T0 | 0.013 | 0.002 |
| T2 | 0.085 | 0.018 | T2 | 0.085 | 0.018 |
| T4 | 0.023 | 0.019 | T4 | 0.024 | 0.012 |
| T6 | 0.011 | 0.010 | T6 | 0.009 | 0.008 |
| T8 | 0.007 | 0.007 | T8 | 0.006 | 0.003 |
| T12 | 0.008 | 0.002 | T12 | 0.009 | 0.006 |
| T24 | 0.009 | 0.005 | T24 | 0.011 | 0.003 |
| AMP = 0.4, HBV = 0 | | | AMP = 0.4, HBV = 2 | | |
| T0 | 0.013 | 0.002 | T0 | 0.013 | 0.002 |
| T2 | 0.085 | 0.018 | T2 | 0.085 | 0.018 |
| T4 | 0.191 | 0.042 | T4 | 0.098 | 0.054 |
| T6 | 0.110 | 0.027 | T6 | 0.061 | 0.041 |
| T8 | 0.048 | 0.019 | T8 | 0.034 | 0.027 |
| T12 | 0.027 | 0.009 | T12 | 0.020 | 0.011 |
| T24 | 0.027 | 0.005 | T24 | 0.018 | 0.008 |
| AMP = 0.4, HBV = 4 | | | AMP = 0.4, HBV = 8 | | |
| T0 | 0.013 | 0.002 | T0 | 0.013 | 0.002 |
| T2 | 0.085 | 0.018 | T2 | 0.085 | 0.018 |
| T4 | 0.040 | 0.028 | T4 | 0.023 | 0.015 |
| T6 | 0.028 | 0.023 | T6 | 0.010 | 0.006 |
| T8 | 0.019 | 0.017 | T8 | 0.006 | 0.004 |
| T12 | 0.012 | 0.004 | T12 | 0.008 | 0.005 |
| T24 | 0.009 | 0.007 | T24 | 0.010 | 0.006 |
| AMP = 0.4, HBV = 16 | | | | | |
| T0 | 0.013 | 0.002 | | | |
| T2 | 0.085 | 0.018 | | | |
| T4 | 0.027 | 0.013 | | | |
| T6 | 0.008 | 0.004 | | | |
| T8 | 0.006 | 0.004 | | | |
| T12 | 0.008 | 0.005 | | | |
| T24 | 0.010 | 0.004 | | | |

TABLE A-2

The checkerboard assay results of kanamycin and honeybee venom verus *S. aureus*.

| TIME | MEAN $A_{660}$ | S.D. | TIME | MEAN $A_{660}$ | S.D. |
|---|---|---|---|---|---|
| KANA = 0, HBV = 0 | | | KANA = 0, HBV = 2 | | |
| T0 | 0.024 | 0.005 | T0 | 0.024 | 0.005 |
| T2 | 0.094 | 0.012 | T2 | 0.095 | 0.011 |
| T4 | 0.854 | 0.157 | T4 | 0.542 | 0.183 |
| T6 | 1.219 | 0.052 | T6 | 1.132 | 0.146 |
| T8 | 1.275 | 0.032 | T8 | 1.275 | 0.042 |
| T12 | 1.320 | 0.044 | T12 | 1.333 | 0.041 |
| T24 | 1.358 | 0.031 | T24 | 1.402 | 0.040 |
| KANA = 0, HBV = 4 | | | KANA = 0, HBV = 8 | | |
| T0 | 0.024 | 0.005 | T0 | 0.024 | 0.005 |

TABLE A-2-continued

The checkerboard assay results of kanamycin and honeybee venom verus *S. aureus*.

| TIME | MEAN A$_{660}$ | S.D. | TIME | MEAN A$_{660}$ | S.D. |
|---|---|---|---|---|---|
| T2 | 0.094 | 0.012 | T2 | 0.094 | 0.012 |
| T4 | 0.154 | 0.131 | T4 | 0.036 | 0.017 |
| T6 | 0.630 | 0.391 | T6 | 0.062 | 0.048 |
| T8 | 1.100 | 0.233 | T8 | 0.571 | 0.403 |
| T12 | 1.322 | 0.048 | T12 | 1.275 | 0.062 |
| T24 | 1.405 | 0.040 | T24 | 1.389 | 0.057 |
| KANA = 0, HBV = 16 | | | KANA = 1.25, HBV = 0 | | |
| T0 | 0.024 | 0.005 | T0 | 0.024 | 0.005 |
| T2 | 0.094 | 0.012 | T2 | 0.094 | 0.012 |
| T4 | 0.029 | 0.014 | T4 | 0.747 | 0.125 |
| T6 | 0.020 | 0.008 | T6 | 1.199 | 0.060 |
| T8 | 0.066 | 0.078 | T8 | 1.269 | 0.043 |
| T12 | 0.666 | 0.556 | T12 | 1.315 | 0.046 |
| T24 | 1.336 | 0.195 | T24 | 1.355 | 0.042 |
| KANA = 1.25, HBV = 2 | | | KANA = 1.25, HBV = 4 | | |
| T0 | 0.024 | 0.005 | T0 | 0.024 | 0.005 |
| T2 | 0.094 | 0.012 | T2 | 0.094 | 0.012 |
| T4 | 0.428 | 0.197 | T4 | 0.107 | 0.060 |
| T6 | 0.929 | 0.369 | T6 | 0.310 | 0.289 |
| T8 | 1.174 | 0.116 | T8 | 0.694 | 0.422 |
| T12 | 1.290 | 0.048 | T12 | 1.231 | 0.107 |
| T24 | 1.373 | 0.035 | T24 | 1.350 | 0.077 |
| KANA = 1.25, HBV = 8 | | | KANA = 1.25, HBV = 16 | | |
| T0 | 0.024 | 0.005 | T0 | 0.024 | 0.005 |
| T2 | 0.094 | 0.012 | T2 | 0.094 | 0.012 |
| T4 | 0.039 | 0.014 | T4 | 0.030 | 0.014 |
| T6 | 0.031 | 0.011 | T6 | 0.017 | 0.009 |
| T8 | 0.095 | 0.129 | T8 | 0.018 | 0.012 |
| T12 | 0.712 | 0.487 | T12 | 0.179 | 0.344 |
| T24 | 1.343 | 0.096 | T24 | 1.124 | 0.357 |
| KANA = 2.5, HBV = 0 | | | KANA = 2.5, HBV = 2 | | |
| T0 | 0.024 | 0.005 | T0 | 0.024 | 0.005 |
| T2 | 0.094 | 0.012 | T2 | 0.094 | 0.012 |
| T4 | 0.630 | 0.081 | T4 | 0.358 | 0.203 |
| T6 | 1.090 | 0.093 | T6 | 0.747 | 0.438 |
| T8 | 1.227 | 0.042 | T8 | 0.925 | 0.462 |
| T12 | 1.248 | 0.046 | T12 | 1.229 | 0.079 |
| T24 | 1.315 | 0.056 | T24 | 1.320 | 0.073 |
| KANA = 2.5, HBV = 4 | | | KANA = 2.5, HBV = 8 | | |
| T0 | 0.024 | 0.005 | T0 | 0.025 | 0.005 |
| T2 | 0.994 | 0.012 | T2 | 0.094 | 0.012 |
| T4 | 0.089 | 0.070 | T4 | 0.037 | 0.015 |
| T6 | 0.124 | 0.191 | T6 | 0.026 | 0.010 |
| T8 | 0.186 | 0.279 | T8 | 0.021 | 0.010 |
| T12 | 0.842 | 0.381 | T12 | 0.187 | 0.224 |
| T24 | 1.284 | 0.062 | T24 | 1.287 | 0.100 |
| KANA = 2.5, HBV = 16 | | | KANA = 5, HBV = 0 | | |
| T0 | 0.024 | 0.005 | T0 | 0.024 | 0.005 |
| T2 | 0.094 | 0.012 | T2 | 0.094 | 0.012 |
| T4 | 0.028 | 0.014 | T4 | 0.448 | 0.076 |
| T6 | 0.017 | 0.009 | T6 | 0.696 | 0.159 |
| T8 | 0.026 | 0.041 | T8 | 0.888 | 0.193 |
| T12 | 0.246 | 0.481 | T12 | 1.008 | 0.195 |
| T24 | 0.950 | 0.589 | T24 | 1.085 | 0.093 |
| KANA = 5, HBV = 2 | | | KANA = 5, HBV = 4 | | |
| T0 | 0.024 | 0.005 | T0 | 0.024 | 0.005 |
| T2 | 0.094 | 0.012 | T2 | 0.094 | 0.012 |
| T4 | 0.265 | 0.152 | T4 | 0.065 | 0.026 |
| T6 | 0.371 | 0.260 | T6 | 0.057 | 0.029 |
| T8 | 0.483 | 0.329 | T8 | 0.065 | 0.047 |
| T12 | 0.915 | 0.189 | T12 | 0.653 | 0.380 |
| T24 | 1.119 | 0.098 | T24 | 1.242 | 0.068 |
| KANA = 5, HBV = 8 | | | KANA = 5, HBV = 16 | | |
| T0 | 0.024 | 0.005 | T0 | 0.024 | 0.005 |
| T2 | 0.094 | 0.012 | T2 | 0.094 | 0.012 |
| T4 | 0.035 | 0.015 | T4 | 0.030 | 0.015 |
| T6 | 0.023 | 0.011 | T6 | 0.019 | 0.009 |
| T8 | 0.018 | 0.012 | T8 | 0.015 | 0.010 |
| T12 | 0.054 | 0.048 | T12 | 0.012 | 0.015 |
| T24 | 1.245 | 0.096 | T24 | 0.484 | 0.544 |
| KANA = 10, HBV = 0 | | | KANA = 10, HBV = 2 | | |
| T0 | 0.024 | 0.005 | T0 | 0.024 | 0.005 |
| T2 | 0.094 | 0.012 | T2 | 0.094 | 0.012 |
| T4 | 0.279 | 0.054 | T4 | 0.167 | 0.089 |
| T6 | 0.359 | 0.063 | T6 | 0.183 | 0.112 |
| T8 | 0.416 | 0.082 | T8 | 0.205 | 0.128 |
| T12 | 0.667 | 0.175 | T12 | 0.666 | 0.168 |
| T24 | 0.995 | 0.074 | T24 | 1.153 | 0.070 |
| KANA = 10, HBV = 4 | | | KANA = 10, HBV = 8 | | |
| T0 | 0.024 | 0.005 | T0 | 0.024 | 0.005 |
| T2 | 0.094 | 0.012 | T2 | 0.094 | 0.012 |
| T4 | 0.064 | 0.023 | T4 | 0.041 | 0.023 |
| T6 | 0.054 | 0.021 | T6 | 0.027 | 0.019 |
| T8 | 0.052 | 0.024 | T8 | 0.023 | 0.019 |
| T12 | 0.314 | 0.299 | T12 | 0.022 | 0.018 |
| T24 | 1.193 | 0.080 | T24 | 0.836 | 0.412 |
| KANA = 10, HBV = 16 | | | | | |
| T0 | 0.024 | 0.005 | | | |
| T2 | 0.094 | 0.012 | | | |
| T4 | 0.031 | 0.014 | | | |
| T6 | 0.020 | 0.009 | | | |
| T8 | 0.014 | 0.010 | | | |
| T12 | 0.015 | 0.013 | | | |
| T24 | 0.614 | 0.567 | | | |

TABLE A-3

The checkboard assay results of polymyxin B and honeybee venom verus *E. coli*.

| TIME | MEAN A$_{660}$ | S.D. | TIME | MEAN A$_{660}$ | S.D. |
|---|---|---|---|---|---|
| POLY B = 0, HBV = 0 | | | POLY B = 0, HBV = 2 | | |
| T0 | 0.006 | 0.002 | T0 | 0.006 | 0.002 |
| T2 | 0.074 | 0.004 | T2 | 0.074 | 0.004 |
| T4 | 0.785 | 0.061 | T4 | 0.195 | 0.116 |
| T6 | 1.243 | 0.011 | T6 | 0.886 | 0.304 |
| T8 | 1.295 | 0.024 | T8 | 1.264 | 0.027 |
| T12 | 1.343 | 0.018 | T12 | 1.316 | 0.026 |
| T24 | 1.396 | 0.023 | T24 | 1.405 | 0.020 |
| POLY B = 0, HBV = 4 | | | POLY B = 0, HBV = 8 | | |
| T0 | 0.006 | 0.002 | T0 | 0.006 | 0.002 |
| T2 | 0.074 | 0.004 | T2 | 0.074 | 0.004 |
| T4 | 0.038 | 0.013 | T4 | 0.018 | 0.008 |
| T6 | 0.070 | 0.046 | T6 | 0.012 | 0.014 |
| T8 | 0.589 | 0.235 | T8 | 0.022 | 0.012 |
| T12 | 1.315 | 0.081 | T12 | 0.769 | 0.503 |
| T24 | 1.415 | 0.024 | T24 | 1.405 | 0.028 |
| POLY B = 0, HBVOM = 16 | | | POLY B = 312, HBV = 0 | | |
| T0 | 0.006 | 0.002 | T0 | 0.006 | 0.022 |
| T2 | 0.074 | 0.004 | T2 | 0.074 | 0.004 |
| T4 | 0.015 | 0.007 | T4 | 0.526 | 0.138 |
| T6 | 0.006 | 0.003 | T6 | 1.046 | 0.269 |
| T8 | 0.007 | 0.004 | T8 | 1.244 | 0.057 |
| T12 | 0.012 | 0.005 | T12 | 1.305 | 0.051 |
| T24 | 0.457 | 0.566 | T24 | 1.429 | 0.053 |
| POLY B = 312, HBV = 2 | | | POLY B = 312, HBV = 4 | | |
| T0 | 0.006 | 0.002 | T0 | 0.006 | 0.002 |
| T2 | 0.074 | 0.004 | T2 | 0.074 | 0.004 |
| T4 | 0.167 | 0.071 | T4 | 0.023 | 0.013 |
| T6 | 0.795 | 0.231 | T6 | 0.064 | 0.132 |
| T8 | 1.195 | 0.117 | T8 | 0.216 | 0.357 |
| T12 | 1.303 | 0.041 | T12 | 0.812 | 0.513 |
| T24 | 1.422 | 0.066 | T24 | 1.415 | 0.040 |
| POLY B = 312, HBV = 8 | | | POLY B = 312, HBV = 16 | | |
| T0 | 0.006 | 0.002 | T0 | 0.006 | 0.002 |
| T2 | 0.074 | 0.004 | T2 | 0.074 | 0.004 |
| T4 | 0.014 | 0.005 | T4 | 0.023 | 0.008 |
| T6 | 0.007 | 0.005 | T6 | 0.013 | 0.004 |
| T8 | 0.011 | 0.005 | T8 | 0.013 | 0.004 |
| T12 | 0.384 | 0.383 | T12 | 0.031 | 0.048 |
| T24 | 1.294 | 0.393 | T24 | 0.334 | 0.579 |
| POLY B = 625, HBV = 0 | | | POLY B = 625, HBV = 2 | | |
| T0 | 0.006 | 0.002 | T0 | 0.006 | 0.002 |
| T2 | 0.074 | 0.004 | T2 | 0.074 | 0.004 |
| T4 | 0.330 | 0.117 | T4 | 0.165 | 0.076 |
| T6 | 0.766 | 0.386 | T6 | 0.553 | 0.267 |
| T8 | 1.048 | 0.314 | T8 | 1.037 | 0.260 |
| T12 | 1.238 | 0.125 | T12 | 1.261 | 0.067 |
| T24 | 1.401 | 0.123 | T24 | 1.405 | 0.075 |
| POLY B = 625, HBV = 4 | | | POLY B = 625, HBV = 8 | | |
| T0 | 0.006 | 0.002 | T0 | 0.007 | 0.002 |

TABLE A-3-continued

The checkboard assay results of polymyxin B and honeybee venom verus E. coli.

| TIME | MEAN $A_{660}$ | S.D. | TIME | MEAN $A_{660}$ | S.D. |
|---|---|---|---|---|---|
| T2 | 0.074 | 0.004 | T2 | 0.074 | 0.004 |
| T4 | 0.025 | 0.011 | T4 | 0.015 | 0.005 |
| T6 | 0.030 | 0.034 | T6 | 0.009 | 0.004 |
| T8 | 0.073 | 0.128 | T8 | 0.011 | 0.005 |
| T12 | 0.627 | 0.428 | T12 | 0.051 | 0.062 |
| T24 | 1.405 | 0.050 | T24 | 1.323 | 0.307 |
| POLY B = 625, HBV = 16 | | | POLY B = 1250, HBV = 0 | | |
| T0 | 0.006 | 0.002 | T0 | 0.006 | 0.002 |
| T2 | 0.074 | 0.004 | T2 | 0.074 | 0.004 |
| T4 | 0.039 | 0.013 | T4 | 0.159 | 0.032 |
| T6 | 0.023 | 0.008 | T6 | 0.172 | 0.093 |
| T8 | 0.022 | 0.007 | T8 | 0.259 | 0.261 |
| T12 | 0.022 | 0.007 | T12 | 0.778 | 0.437 |
| T24 | 0.294 | 0.538 | T24 | 1.362 | 0.094 |
| POLY B = 1250, HBV = 2 | | | POLY B = 1250, HBV = 4 | | |
| T0 | 0.006 | 0.002 | T0 | 0.006 | 0.002 |
| T2 | 0.074 | 0.004 | T2 | 0.074 | 0.004 |
| T4 | 0.110 | 0.043 | T4 | 0.038 | 0.012 |
| T6 | 0.115 | 0.085 | T6 | 0.020 | 0.009 |
| T8 | 0.203 | 0.237 | T8 | 0.018 | 0.006 |
| T12 | 0.552 | 0.557 | T12 | 0.033 | 0.042 |
| T24 | 1.207 | 0.487 | T24 | 1.150 | 0.449 |
| POLY B = 1250, HBV = 8 | | | POLY B = 1250, HBV = 16 | | |
| T0 | 0.006 | 0.002 | T0 | 0.006 | 0.002 |
| T2 | 0.074 | 0.004 | T2 | 0.074 | 0.004 |
| T4 | 0.028 | 0.010 | T4 | 0.071 | 0.014 |
| T6 | 0.019 | 0.007 | T6 | 0.054 | 0.012 |
| T8 | 0.019 | 0.006 | T8 | 0.046 | 0.009 |
| T12 | 0.021 | 0.010 | T12 | 0.036 | 0.006 |
| T24 | 1.013 | 0.556 | T24 | 0.223 | 0.440 |
| POLY B = 2500, HBV = 0 | | | POLY B = 2500, HBV = 2 | | |
| T0 | 0.006 | 0.002 | T0 | 0.006 | 0.002 |
| T2 | 0.074 | 0.004 | T2 | 0.074 | 0.004 |
| T4 | 0.123 | 0.013 | T4 | 0.107 | 0.022 |
| T6 | 0.109 | 0.019 | T6 | 0.085 | 0.021 |
| T8 | 0.167 | 0.276 | T8 | 0.072 | 0.020 |
| T12 | 0.075 | 0.010 | T12 | 0.056 | 0.013 |
| T24 | 1.037 | 0.423 | T24 | 0.879 | 0.530 |
| POLY B = 2500, HBV = 4 | | | POLY B = 2500, HBV = 8 | | |
| T0 | 0.006 | 0.002 | T0 | 0.006 | 0.002 |
| T2 | 0.074 | 0.004 | T2 | 0.074 | 0.004 |
| T4 | 0.080 | 0.013 | T4 | 0.070 | 0.020 |
| T6 | 0.065 | 0.013 | T6 | 0.067 | 0.010 |
| T8 | 0.057 | 0.008 | T8 | 0.058 | 0.015 |
| T12 | 0.049 | 0.011 | T12 | 0.052 | 0.007 |
| T24 | 0.416 | 0.491 | T24 | 0.301 | 0.524 |
| POLY B = 2500, HBV = 16 | | | | | |
| T0 | 0.006 | 0.002 | | | |
| T2 | 0.074 | 0.004 | | | |
| T4 | 0.110 | 0.009 | | | |
| T6 | 0.091 | 0.008 | | | |
| T8 | 0.078 | 0.009 | | | |
| T12 | 0.061 | 0.006 | | | |
| T24 | 0.210 | 0.425 | | | |

TABLE A-4

The checkerboard assay results of ampicillin and honeybee venom verus E. coli.

| TIME | MEAN $A_{660}$ | S.D. | TIME | MEAN $A_{660}$ | S.D. |
|---|---|---|---|---|---|
| AMP = 0, HBV = 0 | | | AMP = 0, HBV = 5 | | |
| T0 | 0.015 | 0.015 | T0 | 0.015 | 0.015 |
| T2 | 0.084 | 0.032 | T2 | 0.084 | 0.032 |
| T4 | 0.644 | 0.098 | T4 | 0.624 | 0.102 |
| T6 | 1.053 | 0.067 | T6 | 1.049 | 0.081 |
| T8 | 1.071 | 0.071 | T8 | 1.070 | 0.078 |
| T12 | 1.144 | 0.075 | T12 | 1.146 | 0.098 |
| T24 | 1.244 | 0.101 | T24 | 1.258 | 0.128 |
| AMP = 0, HBV = 10 | | | AMP = 0, HBV = 20 | | |
| T0 | 0.015 | 0.015 | T0 | 0.015 | 0.015 |
| T2 | 0.084 | 0.032 | T2 | 0.084 | 0.032 |
| T4 | 0.646 | 0.103 | T4 | 0.643 | 0.132 |
| T6 | 1.056 | 0.085 | T6 | 1.031 | 0.088 |
| T8 | 1.066 | 0.091 | T8 | 1.052 | 0.097 |
| T12 | 1.154 | 0.110 | T12 | 1.127 | 0.113 |
| T24 | 1.260 | 0.139 | T24 | 1.244 | 0.155 |
| AMP = 0, HBV = 40 | | | AMP = 0.5, HBV = 0 | | |
| T0 | 0.015 | 0.015 | T0 | 0.015 | 0.015 |
| T2 | 0.084 | 0.032 | T2 | 0.084 | 0.032 |
| T4 | 0.587 | 0.204 | T4 | 0.600 | 0.099 |
| T6 | 1.026 | 0.092 | T6 | 1.001 | 0.078 |
| T8 | 1.050 | 0.094 | T8 | 0.999 | 0.101 |
| T12 | 1.119 | 0.111 | T12 | 1.085 | 0.111 |
| T24 | 1.210 | 0.167 | T24 | 1.156 | 0.222 |
| AMP = 0.5, HBV = 5 | | | AMP = 0.5, HBV = 10 | | |
| T0 | 0.015 | 0.015 | T0 | 0.015 | 0.015 |
| T2 | 0.084 | 0.032 | T2 | 0.084 | 0.032 |
| T4 | 0.603 | 0.099 | T4 | 0.624 | 0.111 |
| T6 | 0.998 | 0.095 | T6 | 1.001 | 0.097 |
| T8 | 1.011 | 0.097 | T8 | 1.013 | 0.100 |
| T12 | 1.099 | 0.120 | T12 | 1.100 | 0.136 |
| T24 | 1.215 | 0.159 | T24 | 1.219 | 0.176 |
| AMP = 0.5, HBV = 20 | | | AMP = 0.5, HBV = 40 | | |
| T0 | 0.015 | 0.015 | T0 | 0.015 | 0.015 |
| T2 | 0.084 | 0.032 | T2 | 0.084 | 0.032 |
| T4 | 0.614 | 0.148 | T4 | 0.508 | 0.205 |
| T6 | 0.980 | 0.094 | T6 | 0.961 | 0.097 |
| T8 | 0.993 | 0.093 | T8 | 0.991 | 0.098 |
| T12 | 1.073 | 0.123 | T12 | 1.063 | 0.138 |
| T24 | 1.182 | 0.155 | T24 | 1.162 | 0.172 |
| AMP = 1, HBV = 0 | | | AMP = 1, HBV = 5 | | |
| T0 | 0.015 | 0.015 | T0 | 0.015 | 0.015 |
| T2 | 0.084 | 0.032 | T2 | 0.084 | 0.032 |
| T4 | 0.538 | 0.094 | T4 | 0.545 | 0.095 |
| T6 | 0.628 | 0.175 | T6 | 0.621 | 0.126 |
| T8 | 0.493 | 0.157 | T8 | 0.470 | 0.147 |
| T12 | 0.475 | 0.230 | T12 | 0.407 | 0.125 |
| T24 | 0.504 | 0.228 | T24 | 0.447 | 0.028 |
| AMP = 1, HBV = 10 | | | AMP = 1, HBV = 20 | | |
| T0 | 0.015 | 0.016 | T0 | 0.015 | 0.015 |
| T2 | 0.083 | 0.033 | T2 | 0.084 | 0.032 |
| T4 | 0.561 | 0.116 | T4 | 0.543 | 0.122 |
| T6 | 0.506 | 0.077 | T6 | 0.513 | 0.080 |
| T8 | 0.453 | 0.120 | T8 | 0.432 | 0.132 |
| T12 | 0.396 | 0.106 | T12 | 0.367 | 0.104 |
| T24 | 0.414 | 0.028 | T24 | 0.395 | 0.047 |
| AMP = 1, HBV = 40 | | | AMP = 2, HBV = 0 | | |
| T0 | 0.015 | 0.016 | T0 | 0.015 | 0.015 |
| T2 | 0.084 | 0.031 | T2 | 0.084 | 0.032 |
| T4 | 0.439 | 0.183 | T4 | 0.428 | 0.112 |
| T6 | 0.456 | 0.125 | T6 | 0.125 | 0.042 |
| T8 | 0.435 | 0.191 | T8 | 0.133 | 0.055 |
| T12 | 0.385 | 0.163 | T12 | 0.136 | 0.090 |
| T24 | 0.484 | 0.082 | T24 | 0.647 | 0.194 |
| AMP = 2, HBV = 5 | | | AMP = 2, HBV = 10 | | |
| T0 | 0.015 | 0.015 | T0 | 0.015 | 0.015 |
| T2 | 0.084 | 0.032 | T2 | 0.084 | 0.032 |
| T4 | 0.440 | 0.130 | T4 | 0.432 | 0.122 |
| T6 | 0.134 | 0.052 | T6 | 0.127 | 0.052 |
| T8 | 0.148 | 0.073 | T8 | 0.133 | 0.070 |
| T12 | 0.192 | 0.147 | T12 | 0.182 | 0.137 |
| T24 | 0.685 | 0.175 | T24 | 0.654 | 0.253 |
| AMP = 2, HBV = 20 | | | AMP = 2, HBV = 40 | | |
| T0 | 0.015 | 0.015 | T0 | 0.015 | 0.015 |
| T2 | 0.084 | 0.032 | T2 | 0.084 | 0.032 |
| T4 | 0.406 | 0.151 | T4 | 0.300 | 0.173 |
| T6 | 0.114 | 0.054 | T6 | 0.086 | 0.058 |
| T8 | 0.123 | 0.073 | T8 | 0.096 | 0.071 |
| T12 | 0.209 | 0.193 | T12 | 0.098 | 0.055 |
| T24 | 0.687 | 0.205 | T24 | 0.618 | 0.241 |
| AMP = 4, HBV = 0 | | | AMP = 4, HBV = 5 | | |
| T0 | 0.015 | 0.015 | T0 | 0.015 | 0.015 |
| T2 | 0.084 | 0.032 | T2 | 0.084 | 0.032 |
| T4 | 0.158 | 0.118 | T4 | 0.154 | 0.108 |
| T6 | 0.063 | 0.019 | T6 | 0.076 | 0.037 |
| T8 | 0.126 | 0.230 | T8 | 0.084 | 0.044 |
| T12 | 0.055 | 0.023 | T12 | 0.057 | 0.022 |
| T24 | 0.056 | 0.015 | T24 | 0.076 | 0.071 |
| AMP = 4, HBV = 10 | | | AMP = 4, HBV = 20 | | |
| T0 | 0.015 | 0.015 | T0 | 0.015 | 0.015 |
| T2 | 0.084 | 0.032 | T2 | 0.084 | 0.032 |

TABLE A-4-continued

The checkerboard assay results of ampicillin and honeybee venom verus *E. coli.*

| TIME | MEAN A$_{660}$ | S.D. | TIME | MEAN A$_{660}$ | S.D. |
|---|---|---|---|---|---|
| T4 | 0.128 | 0.092 | T4 | 0.090 | 0.070 |
| T6 | 0.075 | 0.039 | T6 | 0.066 | 0.043 |
| T8 | 0.074 | 0.045 | T8 | 0.066 | 0.045 |
| T12 | 0.066 | 0.034 | T12 | 0.050 | 0.031 |
| T24 | 0.063 | 0.032 | T24 | 0.052 | 0.026 |
| AMP = 4, HBV = 40 | | | | | |
| T0 | 0.015 | 0.015 | | | |
| T2 | 0.084 | 0.032 | | | |
| T4 | 0.062 | 0.040 | | | |
| T6 | 0.055 | 0.040 | | | |
| T8 | 0.054 | 0.039 | | | |
| T12 | 0.051 | 0.028 | | | |
| T24 | 0.042 | 0.022 | | | |

TABLE A-5

The checkerboard assay results of kanamycin and honeybee venom verus *E. coli.*

| TIME | MEAN A$_{660}$ | S.D. | TIME | MEAN A$_{660}$ | S.D. |
|---|---|---|---|---|---|
| KANA = 0, HBV = 0 | | | KANA = 0, HBV = 5 | | |
| T0 | 0.025 | 0.009 | T0 | 0.025 | 0.009 |
| T2 | 0.119 | 0.028 | T2 | 0.118 | 0.028 |
| T4 | 0.701 | 0.136 | T4 | 0.726 | 0.108 |
| T6 | 0.980 | 0.075 | T6 | 1.002 | 0.065 |
| T8 | 0.988 | 0.068 | T8 | 1.028 | 0.063 |
| T12 | 1.062 | 0.090 | T12 | 1.104 | 0.084 |
| T24 | 1.144 | 0.119 | T24 | 1.191 | 0.101 |
| KANA = 0, HBV = 10 | | | KANA = 0, HBV = 20 | | |
| T0 | 0.025 | 0.009 | T0 | 0.025 | 0.009 |
| T2 | 0.119 | 0.028 | T2 | 0.119 | 0.028 |
| T4 | 0.747 | 0.108 | T4 | 0.764 | 0.087 |
| T6 | 1.005 | 0.073 | T6 | 1.001 | 0.060 |
| T8 | 1.028 | 0.065 | T8 | 1.026 | 0.063 |
| T12 | 1.099 | 0.094 | T12 | 1.094 | 0.090 |
| T24 | 1.188 | 0.114 | T24 | 1.198 | 0.102 |
| KANA = 0, HBV = 40 | | | KANA = 5, HBV = 0 | | |
| T0 | 0.025 | 0.009 | T0 | 0.025 | 0.009 |
| T2 | 0.119 | 0.028 | T2 | 0.124 | 0.033 |
| T4 | 0.736 | 0.075 | T4 | 0.473 | 0.120 |
| T6 | 0.984 | 0.064 | T6 | 0.800 | 0.132 |
| T8 | 1.005 | 0.062 | T8 | 0.889 | 0.081 |
| T12 | 1.080 | 0.080 | T12 | 0.930 | 0.091 |
| T24 | 1.163 | 0.103 | T24 | 1.019 | 0.119 |
| KANA = 5, HBV = 5 | | | KANA = 5, HBV = 10 | | |
| T0 | 0.025 | 0.009 | T0 | 0.025 | 0.009 |
| T2 | 0.119 | 0.028 | T2 | 0.119 | 0.028 |
| T4 | 0.484 | 0.128 | T4 | 0.480 | 0.146 |
| T6 | 0.827 | 0.129 | T6 | 0.805 | 0.141 |
| T8 | 0.908 | 0.080 | T8 | 0.893 | 0.093 |
| T12 | 0.955 | 0.101 | T12 | 0.939 | 0.108 |
| T24 | 1.050 | 0.122 | T24 | 1.044 | 0.127 |
| KANA = 5, HBV = 20 | | | KANA = 5, HBV = 40 | | |
| T0 | 0.025 | 0.009 | T0 | 0.025 | 0.009 |
| T2 | 0.119 | 0.028 | T2 | 0.119 | 0.028 |
| T4 | 0.493 | 0.169 | T4 | 0.503 | 0.177 |
| T6 | 0.765 | 0.192 | T6 | 0.783 | 0.181 |
| T8 | 0.862 | 0.108 | T8 | 0.873 | 0.096 |
| T12 | 0.942 | 0.116 | T12 | 0.950 | 0.107 |
| T24 | 1.046 | 0.126 | T24 | 1.041 | 0.118 |
| KANA = 10, HBV = 0 | | | KANA = 10, HBV = 5 | | |
| T0 | 0.025 | 0.009 | T0 | 0.025 | 0.009 |
| T2 | 0.119 | 0.028 | T2 | 0.119 | 0.028 |
| T4 | 0.263 | 0.114 | T4 | 0.267 | 0.135 |
| T6 | 0.417 | 0.209 | T6 | 0.414 | 0.242 |
| T8 | 0.576 | 0.222 | T8 | 0.563 | 0.248 |
| T12 | 0.814 | 0.084 | T12 | 0.807 | 0.098 |
| T24 | 0.878 | 0.095 | T24 | 0.894 | 0.095 |
| KANA = 10, HBV = 10 | | | KANA = 10, HBV = 20 | | |
| T0 | 0.025 | 0.009 | T0 | 0.025 | 0.009 |
| T2 | 0.119 | 0.028 | T2 | 0.119 | 0.028 |
| T4 | 0.258 | 0.142 | T4 | 0.257 | 0.153 |
| T6 | 0.364 | 0.243 | T6 | 0.361 | 0.262 |
| T8 | 0.511 | 0.242 | T8 | 0.520 | 0.259 |
| T12 | 0.738 | 0.180 | T12 | 0.754 | 0.171 |
| T24 | 0.873 | 0.078 | T24 | 0.881 | 0.071 |

TABLE A-5-continued

The checkerboard assay results of kanamycin and honeybee venom verus *E. coli.*

| TIME | MEAN A$_{660}$ | S.D. | TIME | MEAN A$_{660}$ | S.D. |
|---|---|---|---|---|---|
| KANA = 10, HBV = 40 | | | KANA = 20, HBV = 0 | | |
| T0 | 0.025 | 0.009 | T0 | 0.025 | 0.009 |
| T2 | 0.119 | 0.028 | T2 | 0.119 | 0.028 |
| T4 | 0.258 | 0.176 | T4 | 0.161 | 0.054 |
| T6 | 0.356 | 0.303 | T6 | 0.161 | 0.065 |
| T8 | 0.494 | 0.292 | T8 | 0.170 | 0.079 |
| T12 | 0.784 | 0.147 | T12 | 0.268 | 0.108 |
| T24 | 0.906 | 0.103 | T24 | 0.631 | 0.103 |
| KANA = 20, HBV = 5 | | | KANA = 20, HBV = 10 | | |
| T0 | 0.025 | 0.009 | T0 | 0.025 | 0.009 |
| T2 | 0.119 | 0.028 | T2 | 0.119 | 0.028 |
| T4 | 0.156 | 0.072 | T4 | 0.144 | 0.075 |
| T6 | 0.133 | 0.083 | T6 | 0.095 | 0.069 |
| T8 | 0.119 | 0.086 | T8 | 0.085 | 0.063 |
| T12 | 0.233 | 0.122 | T12 | 0.209 | 0.081 |
| T24 | 0.678 | 0.112 | T24 | 0.667 | 0.100 |
| KANA = 20, HBV = 20 | | | KANA = 20, HBV = 40 | | |
| T0 | 0.025 | 0.009 | T0 | 0.025 | 0.009 |
| T2 | 0.119 | 0.028 | T2 | 0.119 | 0.028 |
| T4 | 0.128 | 0.081 | T4 | 0.103 | 0.074 |
| T6 | 0.078 | 0.065 | T6 | 0.063 | 0.051 |
| T8 | 0.151 | 0.128 | T8 | 0.063 | 0.048 |
| T12 | 0.174 | 0.061 | T12 | 0.179 | 0.083 |
| T24 | 0.692 | 0.113 | T24 | 0.716 | 0.087 |
| KANA = 40, HBV = 0 | | | KANA = 40, HBV = 5 | | |
| T0 | 0.025 | 0.009 | T0 | 0.024 | 0.009 |
| T2 | 0.119 | 0.028 | T2 | 0.117 | 0.029 |
| T4 | 0.136 | 0.049 | T4 | 0.128 | 0.062 |
| T6 | 0.126 | 0.052 | T6 | 0.098 | 0.071 |
| T8 | 0.120 | 0.057 | T8 | 0.074 | 0.055 |
| T12 | 0.100 | 0.055 | T12 | 0.043 | 0.024 |
| T24 | 0.617 | 0.108 | T24 | 0.432 | 0.301 |
| KANA = 40, HBV = 10 | | | KANA = 40, HBV = 20 | | |
| T0 | 0.025 | 0.009 | T0 | 0.025 | 0.009 |
| T2 | 0.119 | 0.028 | T2 | 0.119 | 0.028 |
| T4 | 0.117 | 0.068 | T4 | 0.096 | 0.059 |
| T6 | 0.066 | 0.047 | T6 | 0.046 | 0.025 |
| T8 | 0.045 | 0.026 | T8 | 0.038 | 0.016 |
| T12 | 0.042 | 0.026 | T12 | 0.039 | 0.017 |
| T24 | 0.416 | 0.310 | T24 | 0.404 | 0.318 |
| KANA = 40, HBV = 40 | | | | | |
| T0 | 0.025 | 0.009 | | | |
| T2 | 0.119 | 0.028 | | | |
| T4 | 0.080 | 0.054 | | | |
| T6 | 0.041 | 0.020 | | | |
| T8 | 0.036 | 0.013 | | | |
| T12 | 0.040 | 0.019 | | | |
| T24 | 0.342 | 0.344 | | | |

TABLE A-6

The checkerboard assay results of polymyxin B and honeybee venom verus *E. coli.*

| TIME | MEAN A$_{660}$ | S.D. | TIME | MEAN A$_{660}$ | S.D. |
|---|---|---|---|---|---|
| POLY B = 0, HBV = 0 | | | POLY B = 0, HBV = 5 | | |
| T0 | 0.012 | 0.005 | T0 | 0.012 | 0.005 |
| T2 | 0.040 | 0.004 | T2 | 0.040 | 0.004 |
| T4 | 0.506 | 0.076 | T4 | 0.529 | 0.080 |
| T6 | 1.011 | 0.110 | T6 | 1.018 | 0.116 |
| T8 | 1.043 | 0.096 | T8 | 1.049 | 0.095 |
| T12 | 1.103 | 0.116 | T12 | 1.113 | 0.119 |
| T24 | 1.201 | 0.137 | T24 | 1.227 | 0.150 |
| POLY B = 0, HBV = 10 | | | POLY B = 0, HBV = 20 | | |
| T0 | 0.012 | 0.005 | T0 | 0.012 | 0.005 |
| T2 | 0.040 | 0.004 | T2 | 0.040 | 0.004 |
| T4 | 0.557 | 0.087 | T4 | 0.544 | 0.061 |
| T6 | 1.010 | 0.130 | T6 | 1.005 | 0.117 |
| T8 | 1.049 | 0.100 | T8 | 1.040 | 0.102 |
| T12 | 1.104 | 0.142 | T12 | 1.092 | 0.139 |
| T24 | 1.228 | 0.162 | T24 | 1.217 | 0.157 |
| POLY B = 0, HBV = 40 | | | POLY B = 1.5, HBV = 0 | | |
| T0 | 0.012 | 0.005 | T0 | 0.012 | 0.005 |
| T2 | 0.040 | 0.004 | T2 | 0.040 | 0.004 |
| T4 | 0.439 | 0.058 | T4 | 0.411 | 0.078 |

TABLE A-6-continued

The checkerboard assay results of polymyxin B
and honeybee venom verus *E. coli.*

| TIME | MEAN A$_{660}$ | S.D. | TIME | MEAN A$_{660}$ | S.D. |
|---|---|---|---|---|---|
| T6 | 0.992 | 0.129 | T6 | 0.984 | 0.105 |
| T8 | 1.036 | 0.116 | T8 | 1.020 | 0.091 |
| T12 | 1.082 | 0.139 | T12 | 1.075 | 0.107 |
| T24 | 1.188 | 0.157 | T24 | 1.200 | 0.141 |
| POLY B = 1.5, HBV = 5 | | | POLY B = 1.5, HBV = 10 | | |
| T0 | 0.012 | 0.003 | T0 | 0.012 | 0.005 |
| T2 | 0.040 | 0.004 | T2 | 0.040 | 0.004 |
| T4 | 0.176 | 0.039 | T4 | 0.160 | 0.078 |
| T6 | 0.851 | 0.142 | T6 | 0.837 | 0.133 |
| T8 | 1.012 | 0.196 | T8 | 1.015 | 0.091 |
| T12 | 1.068 | 0.093 | T12 | 1.073 | 0.134 |
| T24 | 1.200 | 0.063 | T24 | 1.203 | 0.145 |
| POLY B = 1.5, HBV = 20 | | | POLY B = 1.5, HBV = 40 | | |
| T0 | 0.012 | 0.005 | T0 | 0.012 | 0.005 |
| T2 | 0.040 | 0.004 | T2 | 0.040 | 0.004 |
| T4 | 0.058 | 0.026 | T4 | 0.024 | 0.010 |
| T6 | 0.507 | 0.196 | T6 | 0.147 | 0.262 |
| T8 | 0.948 | 0.128 | T8 | 0.438 | 0.390 |
| T12 | 1.046 | 0.120 | T12 | 1.016 | 0.102 |
| T24 | 1.201 | 0.129 | T24 | 1.153 | 0.143 |
| POLY B = 3, HBV = 0 | | | POLY B = 3, HBV = 5 | | |
| T0 | 0.012 | 0.005 | T0 | 0.012 | 0.005 |
| T2 | 0.040 | 0.004 | T2 | 0.040 | 0.004 |
| T4 | 0.138 | 0.094 | T4 | 0.029 | 0.018 |
| T6 | 0.642 | 0.139 | T6 | 0.105 | 0.188 |
| T8 | 0.943 | 0.117 | T8 | 0.174 | 0.339 |
| T12 | 0.985 | 0.147 | T12 | 0.471 | 0.390 |
| T24 | 1.116 | 0.184 | T24 | 1.117 | 0.132 |
| POLY B = 3, HBV = 10 | | | POLY B = 3, HBV = 20 | | |
| T0 | 0.012 | 0.005 | T0 | 0.012 | 0.005 |
| T2 | 0.040 | 0.004 | T2 | 0.040 | 0.004 |
| T4 | 0.030 | 0.019 | T4 | 0.023 | 0.007 |
| T6 | 0.092 | 0.169 | T6 | 0.013 | 0.004 |
| T8 | 0.200 | 0.339 | T8 | 0.016 | 0.013 |
| T12 | 0.442 | 0.414 | T12 | 0.445 | 0.351 |
| T24 | 1.105 | 0.111 | T24 | 1.126 | 0.111 |
| POLY B = 3, HBV = 40 | | | POLY B = 6, HBV = 0 | | |
| T0 | 0.012 | 0.005 | T0 | 0.012 | 0.005 |
| T2 | 0.040 | 0.004 | T2 | 0.040 | 0.004 |
| T4 | 0.033 | 0.014 | T4 | 0.022 | 0.007 |
| T6 | 0.018 | 0.006 | T6 | 0.014 | 0.006 |
| T8 | 0.054 | 0.101 | T8 | 0.011 | 0.004 |
| T12 | 0.444 | 0.357 | T12 | 0.109 | 0.188 |
| T24 | 1.123 | 0.123 | T24 | 0.975 | 0.140 |
| POLY B = 6, HBV = 5 | | | POLY B = 6, HBV = 10 | | |
| T0 | 0.012 | 0.005 | T0 | 0.012 | 0.005 |
| T2 | 0.040 | 0.004 | T2 | 0.040 | 0.004 |
| T4 | 0.024 | 0.006 | T4 | 0.029 | 0.006 |
| T6 | 0.016 | 0.007 | T6 | 0.017 | 0.005 |
| T8 | 0.011 | 0.004 | T8 | 0.012 | 0.004 |
| T12 | 0.056 | 0.115 | T12 | 0.065 | 0.111 |
| T24 | 0.733 | 0.398 | T24 | 0.701 | 0.441 |
| POLY B = 6, HBV = 20 | | | POLY B = 6, HBV = 40 | | |
| T0 | 0.012 | 0.005 | T0 | 0.012 | 0.005 |
| T2 | 0.040 | 0.004 | T2 | 0.042 | 0.009 |
| T4 | 0.030 | 0.007 | T4 | 0.041 | 0.008 |
| T6 | 0.016 | 0.004 | T6 | 0.019 | 0.006 |
| T8 | 0.012 | 0.004 | T8 | 0.014 | 0.006 |
| T12 | 0.066 | 0.116 | T12 | 0.016 | 0.006 |
| T24 | 0.486 | 0.448 | T24 | 0.270 | 0.374 |
| POLY B = 12, HBV = 0 | | | POLY B = 12, HBV = 5 | | |
| T0 | 0.012 | 0.005 | T0 | 0.012 | 0.005 |
| T2 | 0.040 | 0.004 | T2 | 0.040 | 0.004 |
| T4 | 0.018 | 0.005 | T4 | 0.025 | 0.005 |
| T6 | 0.011 | 0.005 | T6 | 0.016 | 0.006 |
| T8 | 0.009 | 0.003 | T8 | 0.011 | 0.005 |
| T12 | 0.075 | 0.150 | T12 | 0.010 | 0.005 |
| T24 | 0.472 | 0.498 | T24 | 0.196 | 0.361 |
| POLY B = 12, HBV = 10 | | | POLY B = 12, HBV = 20 | | |
| T0 | 0.012 | 0.005 | T0 | 0.012 | 0.005 |
| T2 | 0.040 | 0.004 | T2 | 0.040 | 0.004 |
| T4 | 0.029 | 0.004 | T4 | 0.330 | 0.006 |
| T6 | 0.017 | 0.005 | T6 | 0.017 | 0.006 |
| T8 | 0.012 | 0.003 | T8 | 0.013 | 0.003 |
| T12 | 0.024 | 0.051 | T12 | 0.012 | 0.004 |
| T24 | 0.201 | 0.352 | T24 | 0.073 | 0.184 |

TABLE A-6-continued

The checkerboard assay results of polymyxin B
and honeybee venom verus *E. coli.*

| TIME | MEAN A$_{660}$ | S.D. | TIME | MEAN A$_{660}$ | S.D. |
|---|---|---|---|---|---|
| POLY B = 12, HBV = 40 | | | | | |
| T0 | 0.012 | 0.005 | | | |
| T2 | 0.040 | 0.004 | | | |
| T4 | 0.048 | 0.007 | | | |
| T6 | 0.022 | 0.006 | | | |
| T8 | 0.016 | 0.005 | | | |
| T12 | 0.015 | 0.006 | | | |
| T24 | 0.047 | 0.085 | | | |

TABLE A-7

The checkerboard assay results of ampicillin
and honeybee venom verus kanamycin resistant
*S. aureus.*

| TIME | MEAN A$_{660}$ | S.D. | TIME | MEAN A$_{660}$ | S.D. |
|---|---|---|---|---|---|
| AMP = 0, HBV = 0 | | | AMP = 0, HBV = 2 | | |
| T0 | 0.020 | 0.016 | T0 | 0.020 | 0.016 |
| T2 | 0.064 | 0.020 | T2 | 0.064 | 0.020 |
| T4 | 0.382 | 0.155 | T4 | 0.150 | 0.134 |
| T6 | 0.885 | 0.173 | T6 | 0.533 | 0.286 |
| T8 | 1.108 | 0.041 | T8 | 0.937 | 0.207 |
| T12 | 1.191 | 0.035 | T12 | 1.167 | 0.038 |
| T24 | 1.233 | 0.049 | T24 | 1.217 | 0.041 |
| AMP = 0, HBV = 4 | | | AMP = 0, HBV = 8 | | |
| T0 | 0.020 | 0.016 | T0 | 0.020 | 0.016 |
| T2 | 0.064 | 0.020 | T2 | 0.064 | 0.020 |
| T4 | 0.038 | 0.021 | T4 | 0.032 | 0.019 |
| T6 | 0.040 | 0.029 | T6 | 0.015 | 0.010 |
| T8 | 0.155 | 0.184 | T8 | 0.011 | 0.007 |
| T12 | 0.903 | 0.263 | T12 | 0.234 | 0.326 |
| T24 | 1.181 | 0.050 | T24 | 0.894 | 0.441 |
| AMP = 0, HBV = 16 | | | AMP = 0.05, HBV = 0 | | |
| T0 | 0.020 | 0.016 | T0 | 0.020 | 0.016 |
| T2 | 0.064 | 0.020 | T2 | 0.064 | 0.020 |
| T4 | 0.033 | 0.016 | T4 | 0.230 | 0.054 |
| T6 | 0.013 | 0.005 | T6 | 0.338 | 0.076 |
| T8 | 0.007 | 0.004 | T8 | 0.372 | 0.144 |
| T12 | 0.008 | 0.004 | T12 | 0.352 | 0.220 |
| T24 | 0.126 | 0.305 | T24 | 0.461 | 0.139 |
| AMP = 0.05, HBV = 2 | | | AMP = 0.05, HBV = 4 | | |
| T0 | 0.020 | 0.016 | T0 | 0.020 | 0.016 |
| T2 | 0.064 | 0.020 | T2 | 0.064 | 0.020 |
| T4 | 0.112 | 0.099 | T4 | 0.044 | 0.025 |
| T6 | 0.175 | 0.144 | T6 | 0.031 | 0.021 |
| T8 | 0.190 | 0.153 | T8 | 0.025 | 0.018 |
| T12 | 0.130 | 0.131 | T12 | 0.018 | 0.012 |
| T24 | 0.440 | 0.260 | T24 | 0.581 | 0.239 |
| AMP = 0.05, HBV = 8 | | | AMP = 0.05, HBV = 16 | | |
| T0 | 0.020 | 0.016 | T0 | 0.020 | 0.016 |
| T2 | 0.064 | 0.020 | T2 | 0.064 | 0.020 |
| T4 | 0.025 | 0.013 | T4 | 0.035 | 0.016 |
| T6 | 0.013 | 0.009 | T6 | 0.013 | 0.004 |
| T8 | 0.008 | 0.005 | T8 | 0.008 | 0.004 |
| T12 | 0.010 | 0.007 | T12 | 0.008 | 0.004 |
| T24 | 0.150 | 0.295 | T24 | 0.011 | 0.002 |
| AMP = 0.1, HBV = 0 | | | AMP = 0.1, HBV = 2 | | |
| T0 | 0.020 | 0.016 | T0 | 0.020 | 0.016 |
| T2 | 0.064 | 0.020 | T2 | 0.064 | 0.020 |
| T4 | 0.379 | 0.430 | T4 | 0.109 | 0.079 |
| T6 | 0.156 | 0.045 | T6 | 0.108 | 0.063 |
| T8 | 0.112 | 0.038 | T8 | 0.075 | 0.037 |
| T12 | 0.050 | 0.011 | T12 | 0.037 | 0.023 |
| T24 | 0.053 | 0.009 | T24 | 0.052 | 0.034 |
| AMP = 0.1, HBV = 4 | | | AMP = 0.1, HBV = 8 | | |
| T0 | 0.020 | 0.016 | T0 | 0.020 | 0.016 |
| T2 | 0.064 | 0.020 | T2 | 0.064 | 0.020 |
| T4 | 0.045 | 0.029 | T4 | 0.030 | 0.018 |
| T6 | 0.030 | 0.022 | T6 | 0.015 | 0.008 |
| T8 | 0.023 | 0.016 | T8 | 0.010 | 0.004 |
| T12 | 0.018 | 0.012 | T12 | 0.008 | 0.004 |
| T24 | 0.044 | 0.102 | T24 | 0.011 | 0.004 |
| AMP = 0.1, HBV = 16 | | | AMP = 0.2, HBV = 0 | | |
| T0 | 0.020 | 0.016 | T0 | 0.020 | 0.016 |
| T2 | 0.064 | 0.020 | T2 | 0.064 | 0.020 |

TABLE A-7-continued

The checkerboard assay results of ampicillin and honeybee venom verus kanamycin resistant S. aureus.

| TIME | MEAN $A_{660}$ | S.D. | TIME | MEAN $A_{660}$ | S.D. |
|---|---|---|---|---|---|
| T4 | 0.031 | 0.017 | T4 | 0.131 | 0.026 |
| T6 | 0.014 | 0.004 | T6 | 0.110 | 0.024 |
| T8 | 0.007 | 0.005 | T8 | 0.073 | 0.018 |
| T12 | 0.009 | 0.005 | T12 | 0.030 | 0.009 |
| T24 | 0.012 | 0.004 | T24 | 0.037 | 0.051 |
| AMP = 0.2, HBV = 2 | | | AMP = 0.2, HBV = 4 | | |
| T0 | 0.020 | 0.016 | T0 | 0.020 | 0.016 |
| T2 | 0.064 | 0.020 | T2 | 0.064 | 0.020 |
| T4 | 0.071 | 0.052 | T4 | 0.047 | 0.029 |
| T6 | 0.062 | 0.047 | T6 | 0.033 | 0.026 |
| T8 | 0.039 | 0.026 | T8 | 0.024 | 0.018 |
| T12 | 0.018 | 0.011 | T12 | 0.017 | 0.010 |
| T24 | 0.017 | 0.010 | T24 | 0.068 | 0.212 |
| AMP = 0.2, HBV = 8 | | | AMP = 0.2, HBV = 16 | | |
| T0 | 0.020 | 0.016 | T0 | 0.020 | 0.016 |
| T2 | 0.064 | 0.020 | T2 | 0.064 | 0.020 |
| T4 | 0.031 | 0.019 | T4 | 0.036 | 0.015 |
| T6 | 0.016 | 0.010 | T6 | 0.015 | 0.005 |
| T8 | 0.010 | 0.007 | T8 | 0.008 | 0.005 |
| T12 | 0.007 | 0.006 | T12 | 0.008 | 0.005 |
| T24 | 0.010 | 0.004 | T24 | 0.012 | 0.003 |
| AMP = 0.4, HBV = 0 | | | AMP = 0.4, HBV = 2 | | |
| T0 | 0.020 | 0.016 | T0 | 0.020 | 0.016 |
| T2 | 0.064 | 0.020 | T2 | 0.064 | 0.020 |
| T4 | 0.202 | 0.184 | T4 | 0.080 | 0.055 |
| T6 | 0.290 | 0.415 | T6 | 0.073 | 0.044 |
| T8 | 0.285 | 0.472 | T8 | 0.043 | 0.023 |
| T12 | 0.271 | 0.514 | T12 | 0.021 | 0.012 |
| T24 | 0.277 | 0.530 | T24 | 0.020 | 0.012 |
| AMP = 0.4, HBV = 4 | | | AMP = 0.4, HBV = 8 | | |
| T0 | 0.020 | 0.016 | T0 | 0.020 | 0.016 |
| T2 | 0.064 | 0.020 | T2 | 0.064 | 0.020 |
| T4 | 0.044 | 0.026 | T4 | 0.030 | 0.019 |
| T6 | 0.028 | 0.016 | T6 | 0.015 | 0.008 |
| T8 | 0.021 | 0.011 | T8 | 0.008 | 0.005 |
| T12 | 0.014 | 0.006 | T12 | 0.008 | 0.005 |
| T24 | 0.011 | 0.003 | T24 | 0.011 | 0.003 |
| AMP = 0.4, HBV = 16 | | | | | |
| T0 | 0.020 | 0.016 | | | |
| T2 | 0.064 | 0.020 | | | |
| T4 | 0.033 | 0.014 | | | |
| T6 | 0.015 | 0.004 | | | |
| T8 | 0.008 | 0.005 | | | |
| T12 | 0.009 | 0.006 | | | |
| T24 | 0.012 | 0.003 | | | |

TABLE A-8

The checkerboard assay results of kanamycin and honeybee venom verus kanamycin resistant S. aureus.

| TIME | MEAN $A_{660}$ | S.D. | TIME | MEAN $A_{660}$ | S.D. |
|---|---|---|---|---|---|
| KANA = 0, HBV = 0 | | | KANA = 0, HBV = 2 | | |
| T0 | 0.016 | 0.005 | T0 | 0.015 | 0.005 |
| T2 | 0.047 | 0.009 | T2 | 0.047 | 0.009 |
| T4 | 0.636 | 0.151 | T4 | 0.187 | 0.116 |
| T6 | 1.246 | 0.026 | T6 | 0.980 | 0.205 |
| T8 | 1.331 | 0.015 | T8 | 1.056 | 0.481 |
| T12 | 1.356 | 0.025 | T12 | 1.100 | 0.498 |
| T24 | 1.417 | 0.039 | T24 | 1.418 | 0.020 |
| KANA = 0, HBV = 4 | | | KANA = 0, HBV = 8 | | |
| T0 | 0.015 | 0.004 | T0 | 0.015 | 0.004 |
| T2 | 0.047 | 0.009 | T2 | 0.047 | 0.009 |
| T4 | 0.030 | 0.016 | T4 | 0.021 | 0.013 |
| T6 | 0.065 | 0.075 | T6 | 0.016 | 0.009 |
| T8 | 0.373 | 0.354 | T8 | 0.043 | 0.056 |
| T12 | 1.306 | 0.062 | T12 | 0.655 | 0.507 |
| T24 | 1.437 | 0.016 | T24 | 1.402 | 0.034 |
| KANA = 0, HBV = 16 | | | KANA = 5, HBV = 0 | | |
| T0 | 0.015 | 0.004 | T0 | 0.016 | 0.005 |
| T2 | 0.047 | 0.009 | T2 | 0.047 | 0.009 |
| T4 | 0.025 | 0.012 | T4 | 0.204 | 0.103 |
| T6 | 0.014 | 0.007 | T6 | 0.282 | 0.140 |
| T8 | 0.013 | 0.008 | T8 | 0.351 | 0.176 |

TABLE A-8-continued

The checkerboard assay results of kanamycin and honeybee venom verus kanamycin resistant S. aureus.

| TIME | MEAN $A_{660}$ | S.D. | TIME | MEAN $A_{660}$ | S.D. |
|---|---|---|---|---|---|
| T12 | 0.117 | 0.263 | T12 | 0.751 | 0.288 |
| T24 | 0.454 | 0.582 | T24 | 1.152 | 0.121 |
| KANA = 5, HBV = 2 | | | KANA = 5, HBV = 4 | | |
| T0 | 0.015 | 0.004 | T0 | 0.015 | 0.004 |
| T2 | 0.047 | 0.009 | T2 | 0.047 | 0.009 |
| T4 | 0.057 | 0.034 | T4 | 0.031 | 0.017 |
| T6 | 0.059 | 0.038 | T6 | 0.024 | 0.012 |
| T8 | 0.068 | 0.044 | T8 | 0.022 | 0.011 |
| T12 | 0.660 | 0.271 | T12 | 0.147 | 0.223 |
| T24 | 1.299 | 0.046 | T24 | 1.279 | 0.063 |
| KANA = 5, HBV = 8 | | | KANA = 5, HBV = 16 | | |
| T0 | 0.015 | 0.004 | T0 | 0.015 | 0.004 |
| T2 | 0.047 | 0.009 | T2 | 0.047 | 0.009 |
| T4 | 0.022 | 0.013 | T4 | 0.024 | 0.010 |
| T6 | 0.016 | 0.008 | T6 | 0.016 | 0.008 |
| T8 | 0.012 | 0.007 | T8 | 0.014 | 0.008 |
| T12 | 0.015 | 0.008 | T12 | 0.016 | 0.005 |
| T24 | 0.876 | 0.403 | T24 | 0.237 | 0.378 |
| KANA = 10, HBV = 0 | | | KANA = 10, HBV = 2 | | |
| T0 | 0.016 | 0.005 | T0 | 0.015 | 0.004 |
| T2 | 0.047 | 0.009 | T2 | 0.047 | 0.009 |
| T4 | 0.135 | 0.065 | T4 | 0.045 | 0.026 |
| T6 | 0.172 | 0.080 | T6 | 0.044 | 0.029 |
| T8 | 0.200 | 0.086 | T8 | 0.043 | 0.031 |
| T12 | 0.397 | 0.186 | T12 | 0.185 | 0.182 |
| T24 | 1.164 | 0.145 | T24 | 1.056 | 0.412 |
| KANA = 10, HBV = 4 | | | KANA = 10, HBV = 8 | | |
| T0 | 0.015 | 0.004 | T0 | 0.015 | 0.004 |
| T2 | 0.047 | 0.009 | T2 | 0.047 | 0.009 |
| T4 | 0.030 | 0.016 | T4 | 0.022 | 0.012 |
| T6 | 0.023 | 0.010 | T6 | 0.016 | 0.008 |
| T8 | 0.020 | 0.008 | T8 | 0.014 | 0.011 |
| T12 | 0.061 | 0.070 | T12 | 0.015 | 0.006 |
| T24 | 1.135 | 0.305 | T24 | 0.264 | 0.385 |
| KANA = 10, HBV = 16 | | | KANA = 20, HBV = 0 | | |
| T0 | 0.015 | 0.004 | T0 | 0.016 | 0.005 |
| T2 | 0.047 | 0.009 | T2 | 0.047 | 0.009 |
| T4 | 0.022 | 0.011 | T4 | 0.123 | 0.061 |
| T6 | 0.016 | 0.007 | T6 | 0.145 | 0.073 |
| T8 | 0.014 | 0.009 | T8 | 0.166 | 0.079 |
| T12 | 0.017 | 0.006 | T12 | 0.220 | 0.081 |
| T24 | 0.028 | 0.024 | T24 | 0.975 | 0.266 |
| KANA = 20, HB = 2 | | | KANA = 20, HBV = 4 | | |
| T0 | 0.015 | 0.004 | T0 | 0.015 | 0.004 |
| T2 | 0.047 | 0.009 | T2 | 0.047 | 0.009 |
| T4 | 0.044 | 0.020 | T4 | 0.036 | 0.035 |
| T6 | 0.041 | 0.020 | T6 | 0.022 | 0.013 |
| T8 | 0.038 | 0.019 | T8 | 0.019 | 0.011 |
| T12 | 0.096 | 0.067 | T12 | 0.025 | 0.018 |
| T24 | 1.155 | 0.074 | T24 | 0.666 | 0.488 |
| KANA = 20, HBV = 8 | | | KANA = 20, HBV = 16 | | |
| T0 | 0.015 | 0.004 | T0 | 0.015 | 0.004 |
| T2 | 0.047 | 0.009 | T2 | 0.047 | 0.009 |
| T4 | 0.023 | 0.011 | T4 | 0.022 | 0.011 |
| T6 | 0.017 | 0.007 | T6 | 0.016 | 0.011 |
| T8 | 0.014 | 0.006 | T8 | 0.015 | 0.009 |
| T12 | 0.017 | 0.007 | T12 | 0.016 | 0.008 |
| T24 | 0.240 | 0.340 | T24 | 0.081 | 0.151 |
| KANA = 40, HBV = 0 | | | KANA = 40, HBV = 2 | | |
| T0 | 0.016 | 0.005 | T0 | 0.015 | 0.004 |
| T2 | 0.047 | 0.009 | T2 | 0.047 | 0.009 |
| T4 | 0.116 | 0.057 | T4 | 0.048 | 0.021 |
| T6 | 0.146 | 0.069 | T6 | 0.047 | 0.021 |
| T8 | 0.161 | 0.075 | T8 | 0.043 | 0.020 |
| T12 | 0.184 | 0.084 | T12 | 0.049 | 0.022 |
| T24 | 0.697 | 0.396 | T24 | 0.692 | 0.463 |
| KANA = 40, HBV = 4 | | | KANA = 40, HBV = 8 | | |
| T0 | 0.015 | 0.004 | T0 | 0.015 | 0.004 |
| T2 | 0.047 | 0.009 | T2 | 0.047 | 0.009 |
| T4 | 0.033 | 0.023 | T4 | 0.023 | 0.011 |
| T6 | 0.029 | 0.016 | T6 | 0.017 | 0.007 |
| T8 | 0.026 | 0.015 | T8 | 0.015 | 0.008 |
| T12 | 0.043 | 0.068 | T12 | 0.016 | 0.007 |
| T24 | 0.433 | 0.401 | T24 | 0.113 | 0.176 |
| KANA = 40, HBV = 16 | | | | | |

TABLE A-8-continued

The checkerboard assay results of kanamycin and honeybee venom verus kanamycin resistant *S. aurreus*.

| TIME | MEAN $A_{660}$ | S.D. | TIME | MEAN $A_{660}$ | S.D. |
|---|---|---|---|---|---|
| T0 | 0.015 | 0.004 | | | |
| T2 | 0.047 | 0.009 | | | |
| T4 | 0.023 | 0.011 | | | |
| T6 | 0.017 | 0.008 | | | |
| T8 | 0.016 | 0.008 | | | |
| T12 | 0.019 | 0.007 | | | |
| T24 | 0.023 | 0.009 | | | |

TABLE A-9

The checkerboard assay results of polymyxin B and honeybee venom verus kanamycin resistant *S. aureus*.

| TIME | MEAN $A_{660}$ | S.D. | TIME | MEAN $A_{660}$ | S.D. |
|---|---|---|---|---|---|
| POLY B = 0, HBV = 0 | | | POLY B = 0, HBV = 2 | | |
| T0 | 0.009 | 0.003 | T0 | 0.009 | 0.003 |
| T2 | 0.068 | 0.004 | T2 | 0.068 | 0.004 |
| T4 | 0.329 | 0.079 | T4 | 0.178 | 0.042 |
| T6 | 0.726 | 0.149 | T6 | 0.621 | 0.122 |
| T8 | 0.887 | 0.107 | T8 | 0.851 | 0.112 |
| T12 | 1.020 | 0.078 | T12 | 1.065 | 0.072 |
| T24 | 1.027 | 0.093 | T24 | 1.106 | 0.083 |
| POLY B = 0, HBV = 4 | | | POLY B = 0, HBV = 8 | | |
| T0 | 0.009 | 0.003 | T0 | 0.009 | 0.003 |
| T2 | 0.068 | 0.004 | T2 | 0.068 | 0.004 |
| T4 | 0.046 | 0.019 | T4 | 0.023 | 0.013 |
| T6 | 0.050 | 0.020 | T6 | 0.012 | 0.011 |
| T8 | 0.162 | 0.087 | T8 | 0.007 | 0.003 |
| T12 | 0.921 | 0.053 | T12 | 0.138 | 0.142 |
| T24 | 1.029 | 0.090 | T24 | 1.038 | 0.068 |
| POLY B = 0, HBV = 16 | | | POLY B = 12.5, HBV = 0 | | |
| T0 | 0.009 | 0.003 | T0 | 0.009 | 0.003 |
| T2 | 0.068 | 0.004 | T2 | 0.068 | 0.004 |
| T4 | 0.034 | 0.010 | T4 | 0.266 | 0.051 |
| T6 | 0.013 | 0.004 | T6 | 0.640 | 0.120 |
| T8 | 0.010 | 0.002 | T8 | 0.826 | 0.110 |
| T12 | 0.011 | 0.003 | T12 | 0.976 | 0.095 |
| T24 | 0.142 | 0.268 | T24 | 0.962 | 0.074 |
| POLY B = 12.5, HBV = 2 | | | POLY B = 12.5, HBV = 4 | | |
| T0 | 0.009 | 0.003 | T0 | 0.009 | 0.003 |
| T2 | 0.068 | 0.004 | T2 | 0.068 | 0.004 |
| T4 | 0.132 | 0.039 | T4 | 0.035 | 0.012 |
| T6 | 0.490 | 0.142 | T6 | 0.024 | 0.007 |
| T8 | 0.742 | 0.196 | T8 | 0.039 | 0.018 |
| T12 | 1.027 | 0.093 | T12 | 0.684 | 0.171 |
| T24 | 1.083 | 0.063 | T24 | 0.996 | 0.077 |
| POLY B = 12.5, HBV = 8 | | | POLY B = 12.5, HBV = 16 | | |
| T0 | 0.009 | 0.003 | T0 | 0.009 | 0.003 |
| T2 | 0.068 | 0.004 | T2 | 0.068 | 0.004 |
| T4 | 0.023 | 0.012 | T4 | 0.036 | 0.012 |
| T6 | 0.010 | 0.005 | T6 | 0.013 | 0.004 |
| T8 | 0.007 | 0.003 | T8 | 0.009 | 0.004 |
| T12 | 0.050 | 0.056 | T12 | 0.011 | 0.004 |
| T24 | 0.993 | 0.073 | T24 | 0.161 | 0.202 |
| POLY B = 25, HBV = 0 | | | POLY B = 25, HBV = 2 | | |
| T0 | 0.009 | 0.003 | T0 | 0.009 | 0.003 |
| T2 | 0.068 | 0.004 | T2 | 0.068 | 0.004 |
| T4 | 0.243 | 0.033 | T4 | 0.123 | 0.037 |
| T6 | 0.629 | 0.073 | T6 | 0.375 | 0.130 |
| T8 | 0.835 | 0.114 | T8 | 0.619 | 0.228 |
| T12 | 1.008 | 0.096 | T12 | 1.994 | 0.088 |
| T24 | 1.048 | 0.091 | T24 | 1.075 | 0.046 |
| POLY B = 25, HBV = 4 | | | POLY B = 25, HBV = 8 | | |
| T0 | 0.009 | 0.003 | T0 | 0.009 | 0.003 |
| T2 | 0.068 | 0.004 | T2 | 0.068 | 0.004 |
| T4 | 0.034 | 0.013 | T4 | 0.022 | 0.012 |
| T6 | 0.018 | 0.007 | T6 | 0.009 | 0.003 |
| T8 | 0.024 | 0.012 | T8 | 0.007 | 0.003 |
| T12 | 0.489 | 0.198 | T12 | 0.016 | 0.014 |
| T24 | 0.973 | 0.093 | T24 | 0.906 | 0.171 |
| POLY B = 25, HBV = 16 | | | POLY B = 50, HBV = 0 | | |
| T0 | 0.009 | 0.003 | T0 | 0.009 | 0.003 |
| T2 | 0.068 | 0.004 | T2 | 0.068 | 0.004 |
| T4 | 0.035 | 0.013 | T4 | 0.208 | 0.034 |
| T6 | 0.015 | 0.008 | T6 | 0.376 | 0.123 |
| T8 | 0.009 | 0.003 | T8 | 0.567 | 0.192 |
| T12 | 0.011 | 0.004 | T12 | 0.841 | 0.115 |
| T24 | 0.178 | 0.291 | T24 | 0.968 | 0.048 |
| POLY B = 50, HBV = 2 | | | POLY B = 50, HBV = 4 | | |
| T0 | 0.009 | 0.003 | T0 | 0.009 | 0.003 |
| T2 | 0.068 | 0.004 | T2 | 0.067 | 0.004 |
| T4 | 0.083 | 0.046 | T4 | 0.027 | 0.013 |
| T6 | 0.158 | 0.122 | T6 | 0.012 | 0.006 |
| T8 | 0.253 | 0.229 | T8 | 0.011 | 0.006 |
| T12 | 0.674 | 0.275 | T12 | 0.263 | 0.177 |
| T24 | 0.971 | 0.105 | T24 | 0.951 | 0.105 |
| POLY B = 50, HBV = 8 | | | POLY B = 50, HBV = 16 | | |
| T0 | 0.009 | 0.003 | T0 | 0.009 | 0.003 |
| T2 | 0.068 | 0.004 | T2 | 0.068 | 0.004 |
| T4 | 0.021 | 0.010 | T4 | 0.038 | 0.012 |
| T6 | 0.009 | 0.002 | T6 | 0.015 | 0.005 |
| T8 | 0.006 | 0.003 | T8 | 0.011 | 0.005 |
| T12 | 0.011 | 0.004 | T12 | 0.012 | 0.004 |
| T24 | 0.807 | 0.222 | T24 | 0.023 | 0.028 |
| POLY B = 100, HBV = 0 | | | POLY B = 100, HBV = 2 | | |
| T0 | 0.009 | 0.003 | T0 | 0.009 | 0.003 |
| T2 | 0.068 | 0.004 | T2 | 0.068 | 0.004 |
| T4 | 0.243 | 0.033 | T4 | 0.123 | 0.037 |
| T6 | 0.629 | 0.073 | T6 | 0.375 | 0.130 |
| T8 | 0.835 | 0.114 | T8 | 0.619 | 0.228 |
| T12 | 1.008 | 0.096 | T12 | 1.994 | 0.088 |
| T24 | 1.048 | 0.091 | T24 | 1.075 | 0.046 |
| POLY B = 100, HBV = 4 | | | POLY B = 100, HBV = 8 | | |
| T0 | 0.009 | 0.003 | T0 | 0.009 | 0.003 |
| T2 | 0.068 | 0.004 | T2 | 0.068 | 0.004 |
| T4 | 0.034 | 0.013 | T4 | 0.022 | 0.012 |
| T6 | 0.018 | 0.007 | T6 | 0.009 | 0.003 |
| T8 | 0.024 | 0.012 | T8 | 0.007 | 0.003 |
| T12 | 0.489 | 0.198 | T12 | 0.016 | 0.014 |
| T24 | 0.973 | 0.093 | T24 | 0.906 | 0.171 |
| POLY B = 100, HBV = 16 | | | | | |
| T0 | 0.009 | 0.003 | | | |
| T2 | 0.068 | 0.004 | | | |
| T4 | 0.042 | 0.012 | | | |
| T6 | 0.020 | 0.006 | | | |
| T8 | 0.015 | 0.005 | | | |
| T12 | 0.014 | 0.004 | | | |
| T24 | 0.106 | 0.232 | | | |

TABLE A-10

The results of equivalent doses of melittin and whole honeybee venom with and without kanamycin on *S. aureus*.

| TIME | MEAN $A_{660}$ | S.D. | TIME | MEAN $A_{660}$ | S.D. |
|---|---|---|---|---|---|
| KANA = 0, MEL = 0, HBV = 0 | | | KANA = 0, MEL = 0, HBV = 2 | | |
| T0 | 0.021 | 0.002 | T0 | 0.021 | 0.002 |
| T2 | 0.080 | 0.007 | T2 | 0.080 | 0.007 |
| T4 | 0.899 | 0.025 | T4 | 0.381 | 0.201 |
| T6 | 1.262 | 0.015 | T6 | 1.089 | 0.139 |
| T8 | 1.327 | 0.013 | T8 | 1.289 | 0.041 |
| T12 | 1.355 | 0.018 | T12 | 1.347 | 0.033 |
| T24 | 1.398 | 0.037 | T24 | 1.417 | 0.024 |
| KANA = 0, MEL = 1.6, HBV = 0 | | | KANA = 2.5, MEL = 0, HBV = 0 | | |
| T0 | 0.021 | 0.002 | T0 | 0.021 | 0.002 |
| T2 | 0.080 | 0.007 | T2 | 0.080 | 0.007 |
| T4 | 0.374 | 0.189 | T4 | 0.692 | 0.106 |
| T6 | 1.099 | 0.108 | T6 | 1.114 | 0.182 |
| T8 | 1.288 | 0.029 | T8 | 1.217 | 0.180 |
| T12 | 1.339 | 0.025 | T12 | 1.265 | 0.115 |
| T24 | 1.415 | 0.022 | T24 | 1.330 | 0.105 |
| KANA = 2.5, MEL = 0, HBV = 2 | | | KANA = 2.5, MEL = 0, HBV = 2 | | |
| T0 | 0.021 | 0.002 | T0 | 0.021 | 0.003 |
| T2 | 0.080 | 0.007 | T2 | 0.068 | 0.004 |
| T4 | 0.167 | 0.129 | T4 | 0.266 | 0.051 |

TABLE A-10-continued

The results of equivalent doses of melittin and whole honeybee venom with and without kanamycin on *S. aureus*.

| TIME | MEAN $A_{660}$ | S.D. | TIME | MEAN $A_{660}$ | S.D. |
|---|---|---|---|---|---|
| T6 | 0.259 | 0.250 | T6 | 0.640 | 0.120 |
| T8 | 0.428 | 0.370 | T8 | 0.826 | 0.110 |
| T12 | 1.100 | 0.080 | T12 | 0.976 | 0.095 |
| T24 | 1.290 | 0.053 | T24 | 0.962 | 0.074 |
| KANA = 2.5, MEL = 1.6, HBV = 0 | | | | | |
| T0 | 0.021 | 0.002 | | | |
| T2 | 0.080 | 0.007 | | | |
| T4 | 0.152 | 0.121 | | | |
| T6 | 0.219 | 0.218 | | | |
| T8 | 0.366 | 0.363 | | | |
| T12 | 0.030 | 0.124 | | | |
| T24 | 0.286 | 0.064 | | | |

BIBLIOGRAPHY

Benton, A. W. 1965. Bee venom, its collection, toxicity and proteins. Thesis, Dept. Entomology, Cornell University, Ithaca, N.Y.

Benton, A. W., R. A. Morse and F. V. Kosikowski 1963. Bioassay and standarization of venom of the honeybee. Nature 198: 295–296.

Brangi, G. P. and M. Pavan. 1954. Bactericidal properties of bee venom (Translated title, in Italian). Isectes sociaux 1: 209–217.

Brown, L. R., J. Lauterwein, and K. Wuthrich. 1980. High-resolution $^1$H-NMR studies of self-aggregation of melittin in aqueous solution. Biochim. Biophys. Acid 622: 231–244.

Carrizosa, J. and M. E. Levison. 1981. Minimal concentration of aminoglycoside that can synergize with penicillin in entrococcal endocarditis. Antimicrob. Agents Chemother. 20: 405–409.

Coulson, C. C. and R. L. Kincaid. 1985. Gram-preparative purification of calmodulin and S-100 protein using melittin-sepharose chromatography. 69th Annual Meeting of the Federation of American Society for Experimental Biology. Federation Proceedings 44: 1777.

Cynamon, M. H. and G. S. Palmer. 1983. In vitro activity of amoxicillin in combination with clavulanic acid against *Mycobacterium tuberculosis*. Antimicrob. Agents Chemother. 24: 429–431.

Fennel, J. F., W. H. Shipman and L. J. Cole. 1968. Anti-bacterial action of melittin, a polypeptide from bee venom. Proc Soc. Exp. Biol. Med. 127: 707–710.

Franklin, T. J. and G. A. Snow. 1981a. *Biochemistry of antimicrobial action*. Chapman and Hall, New York, N.Y. pp. 67–72.

Franklin, T. J. and G. A. Snow. 1981b. *Biochemistry of antimicrobial action*. Chapman and Hall, New York, N.Y. pp. 73–74.

Guralnick, M. W., L. M. Mulfinger and A. W. Benton. 1986. Collection and standardization of hymenoptera venoms. Folia Allergol. Immunol. Clin. 33: 9–18.

Haberman, E. 1972. Bee and wasp venoms: The biochemistry and pharmacology of their peptides and enzymes are reviewed. Sience 177: 314–322.

Haberman, E. and J. Jentsch. 1967. Sequenzanalyse des melittins aus den tryptischen und peptischen spaltstucken. Hoppe-Seyler's Z. Physiol. Chem. 348: 37–5

Hanke, W., C. Methfessel, H. U. Wilmsen, E. Katz, G. Jung, and G. Boheim. 1983. Melittin and a chemically modified trichotoxin form alamethicin-type multistate pores. Biochim. Biophys. Acta 727: 100–114.

Lauterwein, J., C. Bosch, L. R. Brown and K. Wuthrich. 1979. Physiochmemical studies of the protein-lipid interactions in melittin-containing micelles. Biochim. Biophys. Acta 556: 244–264.

Lauterwein, J., L. R. Brown and K. Wuthrich. 1980. High-resolution $^1$H-MNR studies of monomeric melittin in aqueous solution. Biochim. Biophys. Acta 622: 219–230.

Lowry, O. H., N. J. Rosenbrough, A. L. Farr and R. J. Randall. 1951. Protein measurement with the folin phenol reagent. J. Biol. Chem. 193: 265–275.

Moellering, R. C., C. Wennersten and A. N. Weinberg. 1971. Studies of antibiotic synergism against enterococci. J. Lab. Clin. Med. 77: 821–827.

Mollay, C. and G. Kreil. 1973. Fluorometric measurements on the interaction of melittin with lecithin. Biochim. Biophys. Acta 316: 196–203.

Mulfinger, L. M., A. W. Benton, M. W. Gunalnick and R. A. Wilson. 1986. A qualitative and quantitative analysis of proteins found in vespid venoms. J. Allergy Clin. Immunol. 77: 681–686.

Ortel, S. and F. Markwardt. 1955. Investigations on the bactericidal properties of bee venom (Translated title, in German). Pharmazie 10: 743–746. Abstracted in Chemical Abstracts. 1956. 50: 1229c.

Schmidt-Lange, W. 1941. The bactericidal action of bee venom (Translated title, in German). Munchemer Medizinische Wochenschrift 88: 935–936.

Sebek, O. K. 1980. *Antibiotics*: volume 1; *mechanism of action*. D. Gottlieb and P. D. Shaw (eds.). Springer-Verlag, New York. pp. 142–149.

Tu, A. T. 1977a. *Venoms: chemistry and molecular biology*. John Wiley and Sons, Inc., New York, London, Sydney, and Toronto. pp. 1–16.

Tu, A. T. 1977b. *Venoms; chemistry and molecular biology*. John Wiley and Sons, Inc., New York, London, Sydney, and Toronto, pp. 501–512.

Tu, A. T. 1977c. *Venoms: chemistry and molecular biology*. John Wiley and Sons, Inc., New York, London, Sydney, and Toronto. pp. 505–509.

Volk, W. A. 1978a. *Essentials of medical microbiology*. C. May and J. Frazier (eds.), J. P. Lippincott Company, Phila., New York, San Jose and Toronto. pp. 121–122.

Volk, W. A. 1978b. *Essentials of medical microbiology*. C. May and J. Frazier (eds.). J. P. Lippincott Company, Phila., New York, San Jose and Toronto. pp. 122–126.

Volk, W. A. 1978c. *Essentials of medical microbiology*. C. May and J. Frazier (eds.). J. P. Lippincott Company, Phila., New york, San Jose and Toronto. pp. 130–133.

Volk, W. A. 1978d. *Essentials of medical microbiology*. C. May and J. Frazier (eds.). J. P. Lippincott Company, Phila., New York, San Jose and Toronto. pp. 133–135.

Yunes, R. A. 1982. A circular dichroism study of the structure of *Apis melifera* melittin. Arch. Biochem. Biophys. 216(2): 559–565.

We claim:

1. A method for the treatment of an infection in a mammal which comprises:
   administering an effective dosage of a medicament comprising:
   an antibiotic agent having activity against said infection; and a second agent selected from the group consisting of
at least one Hymenoptera venom,
at least one active protein component of a Hymenoptera venom,
at least one polypeptide component of a Hymenoptera venom, and
mixtures thereof:
the proportions of said antibiotic agent and said second agent being such that said second agent enhances the activity of said antibiotic agent.

2. The method of claim 1 wherein the antibiotic agent comprises an antibiotic selected from a family of antibiotics represented by a member of the group consisting of
ampicillin,
kanamycin,
polymixin B, and
rifampicin.

3. The method of claim 2 wherein the second agent is selected from the group consisting of
honeybee venom,
bumblebee venom,
yellow jacket venom,
bald faced hornet venom,
active protein components of said venoms,
active polypeptide components of said venoms, and
mixtures thereof.

4. The method of claim 3 wherein the antibiotic agent comprises ampicillin and the second agent is honeybee venom.

5. The method of claim 3 wherein the antibiotic agent comprises ampicillin and the second agent is melittin.

6. The method of claim 3 wherein the antibiotic agent comprises kanamycin and the second agent is honeybee venom.

7. The method of claim 3 wherein the antibiotic agent comprises kanamycin and the second agent is melittin.

8. The method of claim 3 wherein the antibiotic agent comprises polymixin B and the second agent is honeybee venom.

9. The method of claim 3 wherein the antibiotic agent comprises polymixin B and the secondary agent is melittin.

10. The method of claim 3 wherein the antibiotic agent comprises rifampicin and the secondary agent is honeybee venom.

11. The method of claim 3 wherein the antibiotic agent comprises rifampicin and the secondary agent is melittin.

12. A dosage unit for the treatment of an infection in a mammal which comprises:
an effective dosage of a medicament comprising:
an antibiotic agent having activity against said infection; and
a second agent selected from the group consisting of
at least one Hymenoptera venom,
at least one active protein component of a Hymenoptera venom,
at least one polypeptide component of a Hymenoptera venom, and
mixtures thereof:
the proportions of said antibiotic agent and said second agent being such that said second agent enhances the activity of said antibiotic agent.

13. The dosage unit of claim 12 wherein the antibiotic agent comprises an antibiotic selected from a family of antibiotics represented by a member of the group consisting of
ampicillin,
kanamycin,
polymixin B, and
rifampicin.

14. The dosage unit of claim 13 wherein the second agent is selected from the group consisting of
honeybee venom,
bumblebee venom,
yellow jacket venom,
bald faced hornet venom,
active protein components of said venoms,
active polypeptide components of said venoms, and
mixtures thereof.

15. The dosage unit of claim 13 wherein the antibiotic agent comprises ampicillin and the second agent is honeybee venom.

16. The dosage unit of claim 13 wherein the antibiotic agent comprises ampicillin and the second agent is melittin.

17. The dosage unit of claim 13 wherein the antibiotic agent comprises kanamycin and the second agent is honeybee venom.

18. The dosage unit of claim 13 wherein the antibiotic agent comprises kanamycin and the second agent is melittin.

19. The dosage unit of claim 13 wherein the antibiotic agent comprises polymixin B and the second agent is honeybee venom.

20. The dosage unit of claim 13 wherein the antibiotic agent comprises polymixin B and the second agent is melittin.

21. The dosage unit of claim 13 wherein the antibiotic agent comprises rifampicin and the second agent is honeybee venom.

22. The dosage unit of claim 13 wherein the antibiotic agent comprises rifampicin and the second agent is melittin.

* * * * *